(12) United States Patent
Yen et al.

(10) Patent No.: US 12,031,186 B2
(45) Date of Patent: *Jul. 9, 2024

(54) HOMOLOGOUS RECOMBINATION REPAIR DEFICIENCY DETECTION

(71) Applicant: GUARDANT HEALTH, INC., Redwood City, CA (US)

(72) Inventors: Jennifer Yen, San Mateo, CA (US); Elena Helman, Redwood City, CA (US); Arielle Yablonovitch, Belmont, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/809,516

(22) Filed: Jun. 28, 2022

(65) Prior Publication Data

US 2023/0107807 A1 Apr. 6, 2023

Related U.S. Application Data

(63) Continuation of application No. 17/320,976, filed on May 14, 2021.

(Continued)

(51) Int. Cl.
*C12Q 1/6886* (2018.01)
*C12Q 1/6869* (2018.01)
(Continued)

(52) U.S. Cl.
CPC ........... *C12Q 1/6886* (2013.01); *G16B 20/20* (2019.02); *G16B 30/10* (2019.02); *G16B 30/20* (2019.02); *G16H 50/30* (2018.01); *C12Q 1/6869* (2013.01)

(58) Field of Classification Search
None
See application file for complete search history.

(56) References Cited

U.S. PATENT DOCUMENTS 5,912,148 A 6/1999 Eggerding
6,130,073 A 10/2000 Eggerding
(Continued)

FOREIGN PATENT DOCUMENTS

EP 2721181 B1 12/2019
WO 2014039556 A1 3/2014
(Continued)

OTHER PUBLICATIONS

Veneris et al. Choosing wisely: Selecting PARP inhibitor combinations to promote anti-tumor immune responses beyond BRCA mutations. Gynecologic Oncology 2020, 156, pp. 488-497, published online Oct. 17, 2019 (Year: 2019).*

(Continued)

*Primary Examiner* — Olivia M. Wise
*Assistant Examiner* — Noah Andrew Auger
(74) *Attorney, Agent, or Firm* — Stephen W. Chen

(57) ABSTRACT

Provided herein are methods of generating a homologous recombination repair deficiency (HRD) score, determining a reference HRD score, determining a HRD status of a test subject having one or more cancer types, and/or treating a disease based on HRD status. Additional methods as well as related systems, apparatuses, and computer readable media are also provided.

20 Claims, 17 Drawing Sheets

Related U.S. Application Data

(60) Provisional application No. 63/041,721, filed on Jun. 19, 2020, provisional application No. 63/025,126, filed on May 14, 2020.

(51) Int. Cl.
    *G16B 20/20*     (2019.01)
    *G16B 30/10*     (2019.01)
    *G16B 30/20*     (2019.01)
    *G16H 50/30*     (2018.01)

(56) References Cited

U.S. PATENT DOCUMENTS

| | | | |
|---|---|---|---|
| 6,210,891 B1 | 4/2001 | Nyren et al. |
| 6,258,568 B1 | 7/2001 | Nyren |
| 6,582,908 B2 | 6/2003 | Fodor et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,329,492 B2 | 2/2008 | Hardin et al. |
| 7,476,503 B2 | 1/2009 | Turner et al. |
| 7,482,120 B2 | 1/2009 | Buzby |
| 7,501,245 B2 | 3/2009 | Quake et al. |
| 7,537,898 B2 | 5/2009 | Bost et al. |
| 9,598,731 B2 | 3/2017 | Talasaz |
| 2001/0053519 A1 | 12/2001 | Fodor et al. |
| 2003/0152490 A1 | 8/2003 | Trulson et al. |
| 2011/0160078 A1 | 6/2011 | Fodor et al. |
| 2017/0283879 A1 | 10/2017 | Abkevich et al. |

FOREIGN PATENT DOCUMENTS

| | | |
|---|---|---|
| WO | 2014149134 A2 | 9/2014 |
| WO | 2015086473 A1 | 6/2015 |
| WO | 2016025958 A1 | 2/2016 |
| WO | 2018193433 A1 | 10/2018 |
| WO | 2020160414 A1 | 8/2020 |
| WO | 2020176775 A1 | 9/2020 |
| WO | 2021119311 A1 | 6/2021 |

OTHER PUBLICATIONS

Salvi et al. Cell-free DNA as a diagnostic marker for cancer: current insights. OncoTargets and Therapy 2016:9, 6549-6559 (Year: 2016).*
Abida et al., "Non-BRCA DNA Damage Repair Gene Alterations and Response to the PARP Inhibitor Rucaparib in Metastatic Castration-Resistant Prostate Cancer: Analysis From the Phase II TRITON2 Study," Clin Cancer Res Jun. 1, 2020 (26) (11) 2487-2496.
Abou-Alfa, et al., Pemigatinib for previously treated, locally advanced or metastatic cholangiocarcinoma: a multicentre, open-label, phase 2 study. Lancet Oncol May 2020;21(5):671-684.
Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.
Athie et al., "Targeting DNA Repair Defects for Precision Medicine in Prostate Cancer" Curr Oncol Rep, 21(5):42 (2019).
Audeh et al., "Oral poly(ADP-ribose) polymerase inhibitor olaparib in patients with BRCA1 or BRCA2 mutations and recurrent ovarian cancer: a proof-of-concept trial," Lancet, (2010) 376:245-51.
Barbacioru, C. et al. "Abstract 435: Cell-free circulating tumor DNA (ctDNA) detects somatic copy number loss in homologous recombination repair genes" Clinical Research (Excluding Clinical Trials) (2019) p. 435, XP055701312.
De Bono et al., "Olaparib for Metastatic Castration-Resistant Prostate Cancer," N Engl J Med., (2020) 382(22):2091-2102.
Dhawan et al., "DNA Repair Deficiency Is Common in Advanced Prostate Cancer: New Therapeutic Opportunities," Oncologist, 21(8):940-5 (2016).
Fong et al., "Poly(ADP)-ribose polymerase inhibition: frequent durable responses in BRCA carrier ovarian cancer correlating with platinum-free interval," J Clin Oncol, (2010) 28:2512-9.
Helman et al., "Cell-Free DNA Next-Generation Sequencing Prediction of Response and Resistance to Third-Generation EGFR Inhibitor," Clin Lung Cancer, 19(6):518-530 (2018).
Helsten, et al. "The FGFR Landscape in Cancer: Analysis of 4,853 Tumors by Next-Generation Sequencing" Clin Cancer Res Jan. 1, 2016 (22) (1) 259-267.
Hoeijmakers "Genome maintenance mechanisms for preventing cancer," Nature, (2001) 411:366-74.
International search report and written opinion dated Aug. 13, 2021 for PCT/US2021/032539.
Jonsson, P. et al. "Tumour lineage shapes BRCA-mediated phenotypes" Nature 571(7766):576-579.
Levy, S.E. et al. "Advancements in Next-Generation Sequencing" Ann Rev Genomics & Hum Genetics (2016) 17:95-115.
Liu, L. et al. "Comparison of Next-Generation Sequencing Systems" J Biomed & Biotech (2012) Article ID251364:1-11.
Lupo et al., "Inhibition of poly(ADP-ribosyl)ation in cancer: old and new paradigms revisited," Biochim Biophys Acta, (2014) 1846:201-15.
MacLean, D. et al. "Application of 'next-generation' sequencing technologies to microbial genetics" Nature Rev Microbiol (2009) 7:287-296.
Mateo et al., "Olaparib in patients with metastatic castration-resistant prostate cancer with DNA repair gene aberrations (TOPARP-B): a multicentre, open-label, randomised, phase 2 trial," Lancet Oncol., 21(1):162-174 (2020).
Moschetta et al., "BRCA somatic mutations and epigenetic BRCA modifications in serous ovarian cancer," Ann Oncol. (2016) 27:1449-55.
Peng et al. Exploiting the homologous recombination DNA repair network for targeted cancer therapy. World J Clin Oncol 2011; 2(2): 73-79.
Razavi, P. et al. "High-intensity sequencing reveals the sources of plasma circulating cell-free DNA variants" Nature Med (2019) 25(12):1928-1937.
Robinson, D. et al. "Integrative clinical genomics of advanced prostate cancer" Cell (2015) 161:1215-1228.
Ross et al., "Predictors of prostate cancer tissue acquisition by an undirected core bone marrow biopsy in metastatic castration-resistant prostate cancer—a Cancer and Leukemia Group B study," Clin Cancer Res, 11(22):8109-13 (2005).
Sailer et al., "Bone biopsy protocol for advanced prostate cancer in the era of precision medicine," Cancer, 124(5):1008-1015 (2018).
Siegel et al., "Cancer statistics, 2020," CA Cancer J Clin, (2020) 70(1):7-30.
Solinas et al., "BRCA gene mutations do not shape the extent and organization of tumor infiltrating lymphocytes in triple negative breast cancer," Cancer Lett, (2019) 450:88-97.
Spritzer et al., "Bone marrow biopsy: RNA isolation with expression profiling in men with metastatic castration-resistant prostate cancer-factors affecting diagnostic success," Radiology, 269(3):816-23 (2013).
Swisher, E.M. et al. "Rucaparib in relapsed, platinum-sensitive high-grade ovarian carcinoma (ARIEL2 Part 1): an International, multicentre, open-label, phase 2 trial" Lancet (2016) with Supplemental Information; http://dx.doi.org/10.1016/S1470-2045(16)30559-9.
Tate, J.G. et al. "COSMIC: the Catalogue of Somatic Mutations in Cancer." Nucleic Acids Res. (Jan. 8, 2019) 47(D1): D941-D947.
Telli, M.L. et al. "Homologous Recombination Deficiency (HRD) Score Predicts Response to Platinum-Containing Neoadjuvant Chemotherapy in Patients with Triple-Negative Breast Cancer" Clinical Cancer Research (2016) 22(15):3764-3773.

(56) References Cited

OTHER PUBLICATIONS

Timms, K.M. et al. "Association of BRCA1/2 defects with genomic scores predictive of DNA damage repair deficiency among breast cancer subtypes" Breast Cancer Research (2014) 16:475-483.
Voelkerding, K.V. et al. "Next-generation sequencing: from basic research to diagnostics" Clin Chem (2009) 55:641-658.
Wang et al., "PARP-1 and Ku compete for repair of DNA double strand breaks by distinct NHEJ pathways," Nucleic Acids Res, (2006) 34:6170-82.
Yablonovitch et al., "Identification of FGFR2/3 fusions from clinical cfDNA NGS using a de novo fusion caller," May 2020. ASCO Poster.
Jannetti, S.A. "Poly(ADP-Ribose)Polymerase (PARP) Inhibitors and Radiation Therapy" Frontiers in Pharmacology (2020) 11:170 (14 pages).
Office Action for U.S. Appl. No. 17/320,976, dated Feb. 29, 2024.
Wang, R. et al. "Cell-free circulating tumor DNA analysis for breast cancer and its clinical utilization as a biomarker" Oncotarget (2017) 8(43):75742-75755.
Weigelt, B. et al. "Diverse BRCA1 and BRCA2 Reversion Mutation in Circulating Cell-Free DNA or Therapy-Resistant Breast or Ovarian Cancer" Clinical Cancer Research (2017) 23(21):6708-6720.

\* cited by examiner

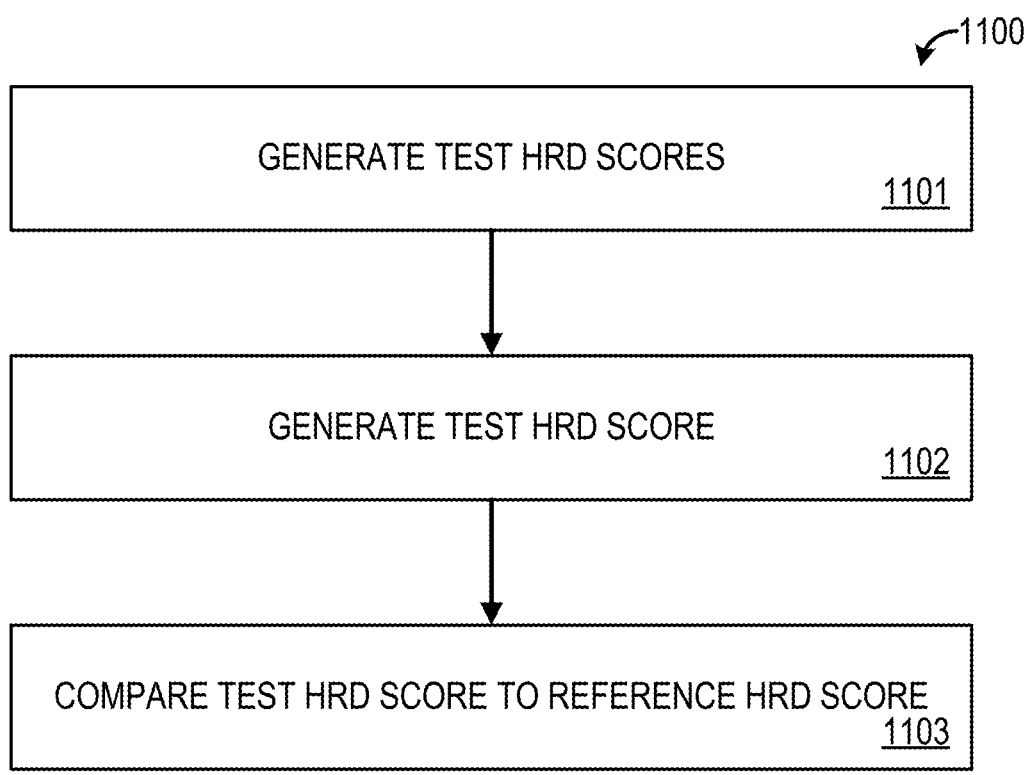

DETERMINE AT LEAST ONE HRD VARIANT USING:
(I) A FIRST PROBABILITY THAT THE SEQUENCE INFORMATION COMPRISES A FIRST STATE AND A SECOND PROBABILITY THAT THE SEQUENCE INFORMATION COMPRISES A SECOND STATE IN WHICH THE FIRST OR SECOND STATE COMPRISES AT LEAST A FIRST HRD NUCLEIC ACID VARIANT; AND/OR
(II) ONE OR MORE ALIGNED CONTIGUOUS SEQUENCES (CONTIGS) GENERATED FROM THE SEQUENCE INFORMATION IN WHICH THE ALIGNED CONTIGS COMPRISE AT LEAST A SECOND HRD NUCLEIC ACID VARIANT, TO THEREBY DETECT HRD.

ADMINISTER ONE OR MORE THERAPIES TO A SUBJECT HAVING A DISEASE AND A HOMOLOGOUS RECOMBINATION DNA REPAIR DEFICIENCY (HRD) ASSOCIATED WITH THE DISEASE, WHICH
  HRD IS DETECTED BY DETERMINING A PRESENCE OF AT LEAST ONE HRD NUCLEIC ACID VARIANT IN SEQUENCE INFORMATION DERIVED FROM CELL-FREE NUCLEIC ACIDS (CFNAS) OBTAINED FROM THE SUBJECT USING:
  (I) A FIRST PROBABILITY THAT THE SEQUENCE INFORMATION COMPRISES A FIRST STATE AND A SECOND PROBABILITY THAT THE SEQUENCE INFORMATION COMPRISES A SECOND STATE IN WHICH THE FIRST OR SECOND STATE COMPRISES AT LEAST A FIRST HRD NUCLEIC ACID VARIANT; AND/OR
  (II) ONE OR MORE ALIGNED CONTIGUOUS SEQUENCES (CONTIGS) GENERATED FROM THE SEQUENCE INFORMATION IN WHICH THE ALIGNED CONTIGS COMPRISE AT LEAST A SECOND HRD NUCLEIC ACID VARIANT, TO THEREBY DETECT THE HRD IN THE SUBJECT

1301

FIG. 15
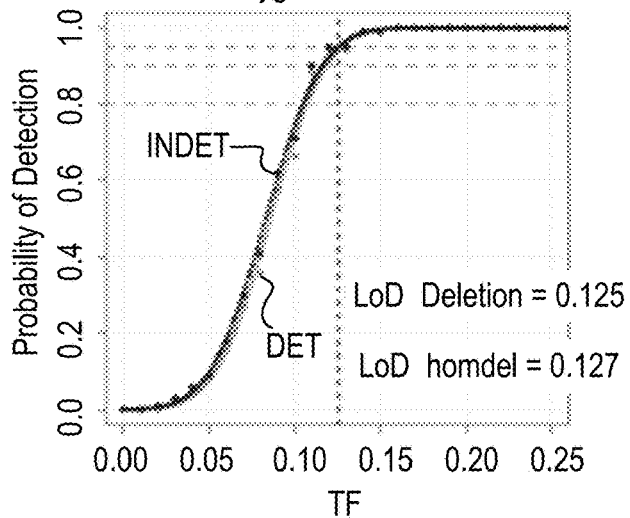
A
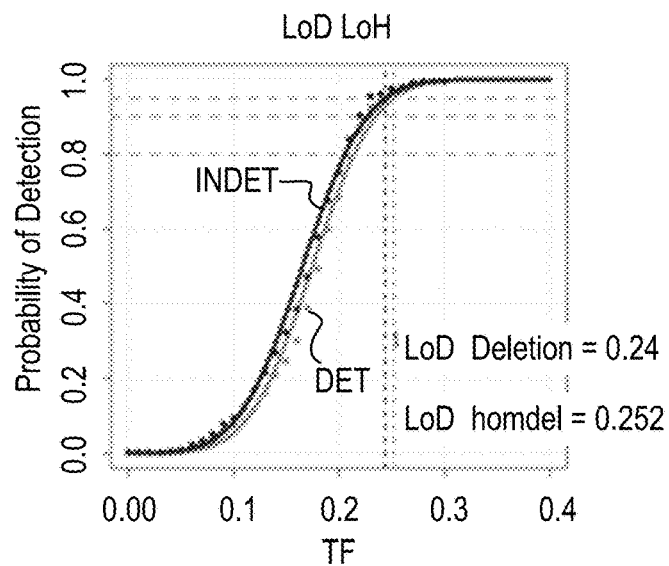
B
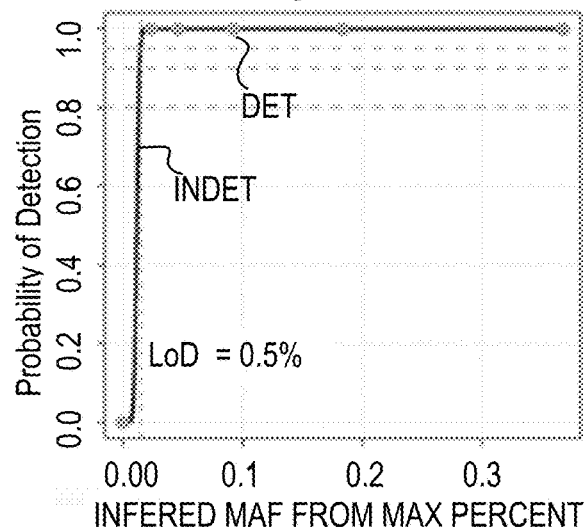
C

FIG. 17
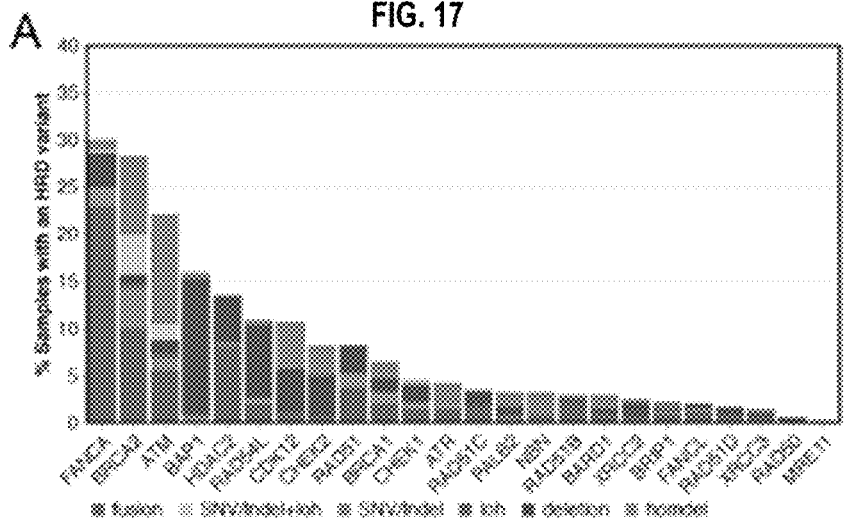
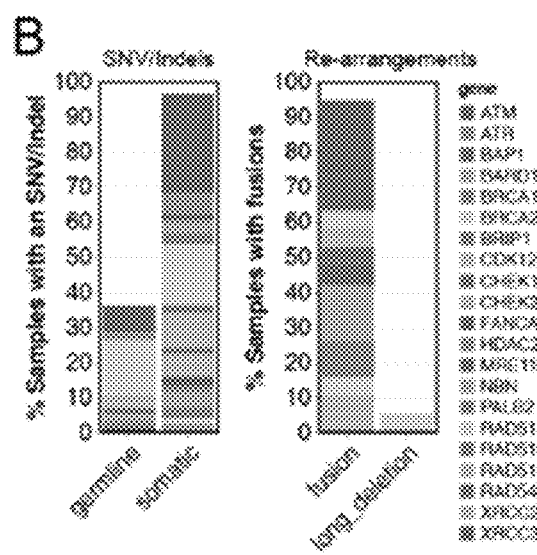
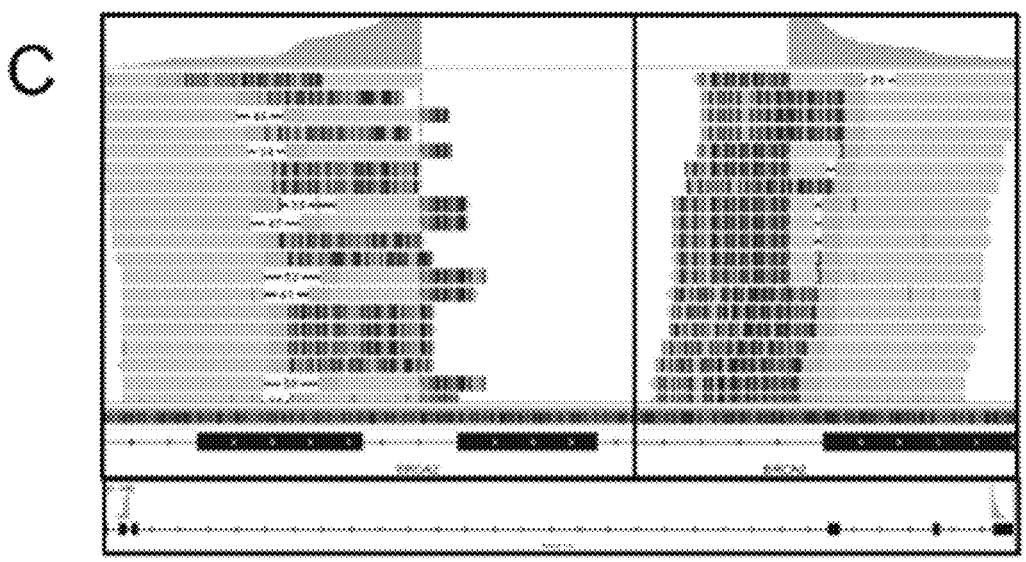

HOMOLOGOUS RECOMBINATION REPAIR DEFICIENCY DETECTION

CROSS REFERENCE TO RELATED PATENT APPLICATIONS

This application is a continuation of U.S. application Ser. No. 17/320,976 filed May 14, 2021, which claims priority to U.S. Provisional Application No. 63/041,721 filed Jun. 19, 2020, and U.S. Provisional Application No. 63/025,126 filed May 14, 2020, herein incorporated by reference in their entireties.

BACKGROUND

There is a complex network of molecular pathways that functions to repair DNA damage in order to maintain genomic stability. For example, homologous recombination DNA repair homologous recombination repair (HRR) operates during the S and G2 phases of the cell cycle as a pathway to correct double-stranded breaks in DNA [Lupo et al., "Inhibition of poly(ADP-ribosyl)ation in cancer: old and new paradigms revisited," Biochim Biophys Acta, 1846: 201-15 (2014); Moschetta et al., "BRCA somatic mutations and epigenetic BRCA modifications in serous ovarian cancer," Ann Oncol., 27:1449-55 (2016)]. The impairment of the HRR pathway, termed HRR deficiency (HRD), results in loss or duplication of chromosomal regions, known as genomic loss of heterozygosity (LOH), and is thought to increase the number of tumor mutations and the neo-antigen rate [Solinas et al., "BRCA gene mutations do not shape the extent and organization of tumor infiltrating lymphocytes in triple negative breast cancer," Cancer Lett, 450:88-97 (2019)]. When cells have a HRD, other repair pathways, such as nonhomologous end-joining (NHEJ) may be used to repair damaged DNA [Wang et al., "PARP-1 and Ku compete for repair of DNA double strand breaks by distinct NHEJ pathways," Nucleic Acids Res, 34:6170-82 (2006)]. NHEJ is more error-prone than HRR and frequently results in the accumulation of additional mutations and chromosomal instability, which increases the likelihood of tumorigenesis [Hoeijmakers, "Genome maintenance mechanisms for preventing cancer," Nature, 411:366-74 (2001)]. Patients with germline or somatic HRD may be candidates for targeted therapies, including DNA damage response (DDR) inhibitors, such as poly (ADP-ribose) polymerase (PARP) inhibitors (PARPi) [Fong et al., "Poly(ADP)-ribose polymerase inhibition: frequent durable responses in BRCA carrier ovarian cancer correlating with platinum-free interval," J Clin Oncol, 28:2512-9 (2010); Audeh et al., "Oral poly(ADP-ribose) polymerase inhibitor olaparib in patients with BRCA1 or BRCA2 mutations and recurrent ovarian cancer: a proof-of-concept trial," Lancet, 376:245-51 (2010)].

Accordingly, there is a need to detect HRD in, or to classify the HRD status of, patients to diagnose and/or guide the treatment of diseases, such as cancer, especially from cell-free nucleic acid (cfDNA) samples.

SUMMARY

The present disclosure provides methods of generating a homologous recombination repair deficiency (HRD) score and determining a HRD status of a test subject having a condition (e.g., cancer). The methods disclosed improve the sensitivity and specificity of cancer detection assays and improve the sensitivity and specificity of identifying patients who may benefit from poly (ADP-ribose) polymerase (PARP) therapy. The methods disclosed may be used to guide treatment strategies. Additional methods as well as related systems and computer readable media are also provided.

In an embodiment, provided is a method of generating a homologous recombination repair deficiency (HRD) score at least partially using a computer, the method comprising generating, by the computer, a reference HRD score for one or more genes in a set of homologous recombination repair (HRR) genes from sequence information derived from cell-free nucleic acids (cfDNA) obtained from one or more reference subjects that have one or more cancer types to produce a set of reference HRD scores, wherein a given reference HRD score comprises a prevalence of a given HRD nucleic acid variant and generating a reference HRD score from the set of reference HRD scores.

In an embodiment, provided is a method of determining a homologous recombination repair deficiency (HRD) status of a test subject having one or more cancer types at least partially using a computer, the method comprising generating a test HRD score for one or more genes in a set of homologous recombination repair (HRR) genes from sequence information derived from cell-free nucleic acids (cfDNA) obtained from the test subject to produce a set of test HRD scores, wherein a given test HRD score comprises a prevalence of a given HRD nucleic acid variant, generating a test HRD score from the set of test HRD scores, and comparing the test HRD score to a reference HRD score, wherein test HRD scores that are above the reference HRD score indicate that those test HRD scores are from test subjects having a HRD, and wherein test HRD scores that are at or below the reference HRD score indicate that those test HRD scores are from test subjects lacking a HRD, thereby determining the HRD status of the test subject having the one or more cancer types.

In an embodiment, provided is a method of detecting a presence or absence of homologous recombination repair deficiency (HRD) in a subject at least partially using a computer, the method comprising determining, by the computer, a presence or absence of at least one HRD nucleic acid variant in sequence information associated with one or more genes in a set of homologous recombination repair (HRR) genes derived from cell-free nucleic acids (cfDNA) obtained from the subject using (i) a first probability that the sequence information comprises a first state and a second probability that the sequence information comprises a second state, wherein the first or second state comprises at least a first HRD nucleic acid variant and/or (ii) one or more aligned contiguous sequences (contigs) generated from the sequence information, wherein the aligned contigs comprise at least a second HRD nucleic acid variant, thereby detecting the HRD in the subject.

In an embodiment, provided is a method of treating a disease, the method comprising administering one or more therapies to a subject having the disease and a homologous recombination repair deficiency (HRD) associated with the disease, which HRD is detected by determining a presence or absence of at least one HRD nucleic acid variant in sequence information associated with one or more genes in a set of homologous recombination repair (HRR) genes derived from cell-free nucleic acids (cfDNA) obtained from the subject using (i) a first probability that the sequence information comprises a first state and a second probability that the sequence information comprises a second state, wherein the first or second state comprises at least a first HRD nucleic acid variant and/or (ii) one or more aligned contiguous sequences (contigs) generated from the sequence information, wherein the aligned contigs comprise at least a second HRD nucleic acid variant, thereby treating the disease.

In an embodiment, provided is a method comprising determining sequence data for a biological sample. The biological sample may comprise cell free DNA (cfDNA). The method may comprise determining, based on the sequence data, coverage data. The method may comprise determining, based on the coverage data, one or more breakpoints associated with one or more fusion events. The method may comprise determining, based on the coverage data, one or more deletions associated with one or more genes. The method may comprise determining, based on the one or more breakpoints and the one or more deletions, a homologous recombination deficiency (HRD) score. The method may comprise classifying, based on the HRD score, the biological sample as HRD positive.

In an embodiment, provided is a method comprising determining sequence data for a biological sample. The biological sample may comprise cell free DNA (cfDNA). The method may comprise determining, based on the sequence data, coverage data. The method may comprise determining, based on the coverage data, one or more breakpoints associated with one or more fusion events. The method may comprise determining, based on the coverage data, one or more deletions associated with one or more genes. The method may comprise determining, based on the one or more breakpoints and the one or more deletions, a homologous recombination deficiency (HRD) score. The method may comprise classifying, based on the HRD score, the biological sample as HRD negative.

In some embodiments, a subject having HRD as determined by any of the methods disclosed may be administered a targeted therapy. The targeted therapy may comprise a PARP inhibitor. Examples of PARP inhibitors that may be administered include one or more of: VELIPARIB, OLAPARIB, TALAZOPARIB, RUCAPARIB, NIRAPARIB, PAMIPARIB, CEP 9722 (Cephalon), E7016 (Eisai), E7449 (Eisai, a PARP ½ and tankyrase ½ inhibitor), or 3-Aminobenzamide. In some embodiments, the targeted therapy may comprise at least one base excision repair (BER) inhibitor. For example, OLAPARIB may inhibit BER. In certain embodiments, the targeted therapy may comprise combination of a PARP inhibitor and radiotherapy. In an embodiment, the combination of a PARP inhibitor and radiotherapy would permit the PARP inhibitor to lead to formation of double strand breaks from the single-strand breaks generated by the radiotherapy in tumor tissue (e.g., tissue with BRCA1/BRCA2 mutations). This combination can provide more powerful therapy per radiation dose.

In some embodiments, the results of the systems and methods disclosed herein are used as an input to generate a report. The report may be in a paper or electronic format. For example, the determination of whether or not a subject has HRD according to an HRD score, as determined by the methods and systems disclosed herein, can be displayed directly in such a report.

The various steps of the methods disclosed herein, or steps carried out by the systems disclosed herein, may be carried out at the same or different times, in the same or different geographical locations, e.g., countries, and/or by the same or different people.

BRIEF DESCRIPTION OF THE FIGURES

The accompanying drawings, which are incorporated in and constitute a part of this specification, illustrate certain embodiments, and together with the written description, serve to explain certain principles of the methods, computer readable media, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 11 is a flow chart that schematically depicts exemplary method steps of determining a homologous recombination DNA repair deficiency (HRD) status of a test subject having a given cancer type according to some embodiments.

FIG. 12 is a flow chart that schematically depicts exemplary method steps of detecting a homologous recombination DNA repair deficiency (HRD) in a subject according to some embodiments.

FIG. 13 is a flow chart that schematically depicts exemplary method steps of treating a disease in a subject according to some embodiments.

FIG. 15 (panels A-C) are plots of data showing the GuardantOMNI® RUO limit of detection (LoD) for HRR deletions and fusions. Panel A shows the LoD for homozygous BRCA2 deletions, panel B shows the LoD for LOH, and panel C shows the LoD for long BRCA1 deletions in which the y-axes plot the probability of detection and the x-axes plot of tumor fraction (TF).

FIG. 17 (panels A-C) are plots of the prevalence of HRR mutations by variant classes detected in the prostate cohort.

DEFINITIONS

Figure 1:
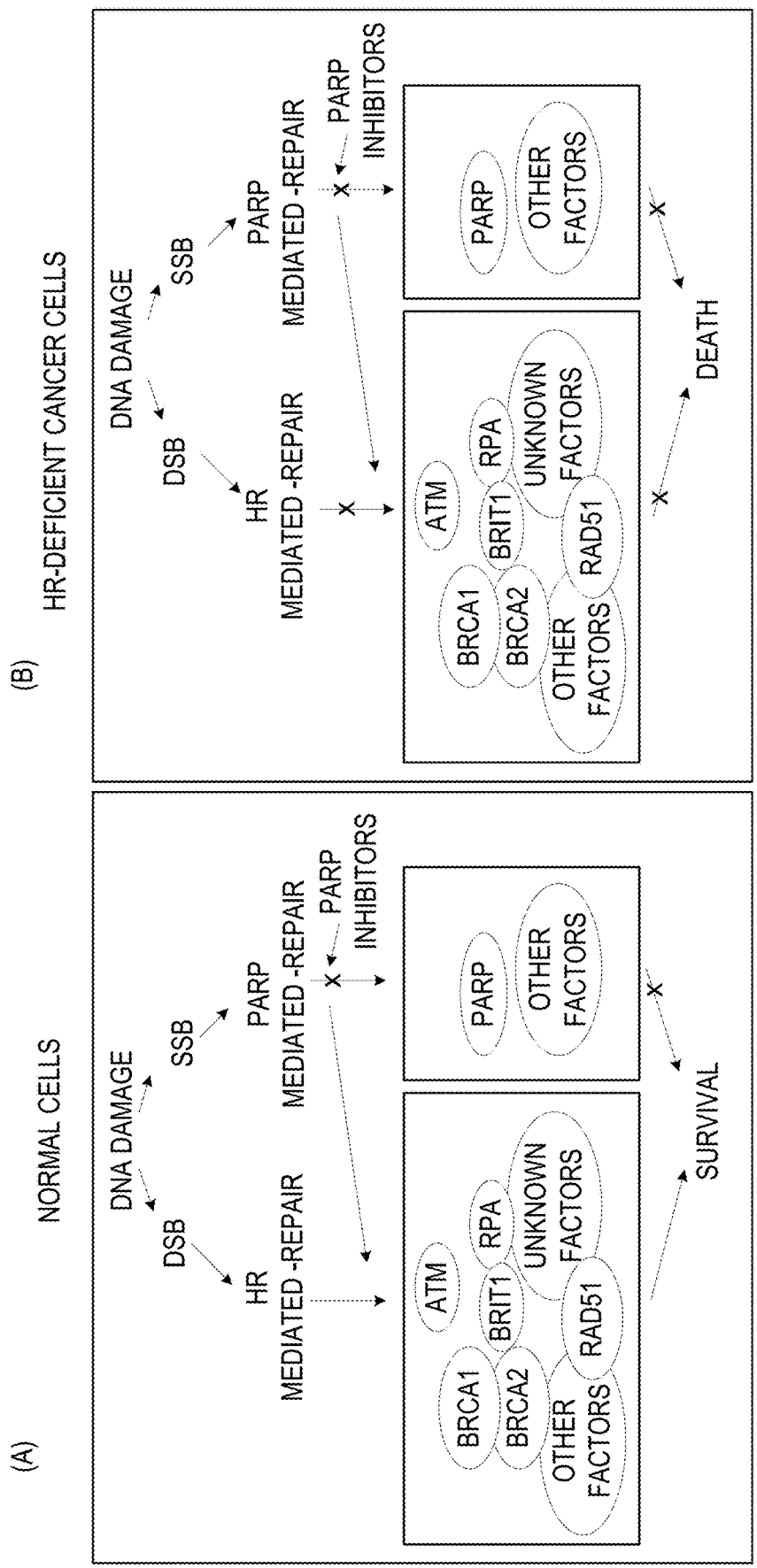
FIG. 1 (panels A and B) are diagrams (modified from Peng et al. Exploiting the homologous recombination DNA repair network for targeted cancer therapy. *World J Clin Oncol* 2011; 2(2): 73-79 [PMID: 21603316]) that schematically show that cells having a deficiency in a homologous recombination repair (HRR) pathway are vulnerable to increased DNA damage and have an increased sensitivity to DNA damage repair inhibitors (e.g., PARP inhibitors, etc.) and/or other therapies.

In order for the present disclosure to be more readily understood, certain terms are first defined below. Additional definitions for the following terms and other terms may be set forth through the specification. If a definition of a term set forth below is inconsistent with a definition in a patent application or issued patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons of ordinary skill in the art upon reading this disclosure and so forth. It will also be appreciated that there is an implied "about" prior to the temperatures, concentrations, times, number of bases or base pairs, coverage, etc. discussed in the present disclosure, such that slight and insubstantial equivalents are within the scope of the present disclosure. In this application, the use of the singular includes the plural unless specifically stated otherwise. Also, the use of "comprise", "comprises", "comprising", "contain", "contains", "containing", "include", "includes", and "including" are not intended to be limiting.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, computer readable media, and systems, the following terminology, and grammatical variants thereof, will be used in accordance with the definitions set forth below.

About: As used herein, "about" or "approximately" as applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Adapter: As used herein, "adapter" refers to short nucleic acids (e.g., less than about 500, less than about 100 or less than about 50 nucleotides in length) that are typically at least partially double-stranded and used to link to either or both ends of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next generation sequencing (NGS) applications. Adapters can also include binding sites for capture probes, such as an oligonucleotide attached to a flow cell support or the like. Adapters can also include a nucleic acid tag as described herein. Nucleic acid tags are typically positioned relative to amplification primer and sequencing primer binding sites, such that a nucleic acid tag is included in amplicons and sequencing reads of a given nucleic acid molecule. Adapters of the same or different sequence can be linked to the respective ends of a nucleic acid molecule. In certain embodiments, the same adapter is linked to the respective ends of the nucleic acid molecule except that the nucleic acid tag differs in its sequence. In some embodiments, the adapter is a Y-shaped adapter in which one end is blunt ended or tailed as described herein, for joining to a nucleic acid molecule, which is also blunt ended or tailed with one or more complementary nucleotides. In still other exemplary embodiments, an adapter is a bell-shaped adapter that includes a blunt or tailed end for joining to a nucleic acid molecule to be analyzed. Other exemplary adapters include T-tailed and C-tailed adapters.

Administer: As used herein, "administer" or "administering" a therapeutic agent (e.g., an immunological therapeutic agent, a DNA damage response (DDR) inhibitor (e.g., a poly (ADP-ribose) polymerase (PARP) inhibitor (PARPi)), etc.) to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Align: As used herein, "align," alignment," and "aligning" in the context of nucleic acids refers to arranging sequences of DNA or RNA to identify regions of similarity. Similarity may be related to functional, structural, and/or evolutionary relationships between the sequences. Alignment of DNA sequences involves alignment of genomic DNA of one sequence to genomic DNA of at least one other sequence. Such alignment may exclude non-genomic DNA, such as a molecular barcode, padding bases, and the like. For example, genomic DNA of a sequence read may be aligned to genomic DNA of a reference DNA sequence, excluding any molecular tag that may be attached to the sequence read.

Allele: As used herein, "allele" or "allelic variant" refers to a specific genetic variant at defined genomic location or locus. An allelic variant is usually presented at a frequency of 50% (0.5) or 100%, depending on whether the allele is heterozygous or homozygous. For example, germline variants are inherited and usually have a frequency of 0.5 or 1. Somatic variants; however, are acquired variants and usually have a frequency of <0.5. Major and minor alleles of a genetic locus refer to nucleic acids harboring the locus in which the locus is occupied by a nucleotide of a reference sequence, and a variant nucleotide different than the reference sequence respectively. Measurements at a locus can take the form of allelic fractions (AFs), which measure the frequency with which an allele is observed in a sample.

Amplify: As used herein, "amplify" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes.

Barcode: As used herein, "barcode" in the context of nucleic acids refers to a nucleic acid molecule having a sequence that can serve as a molecular identifier. For example, individual "barcode" sequences are typically added to DNA fragments during next-generation sequencing (NGS) library preparation so that each read can be identified and sorted before the final data analysis.

Base Excision Repair Inhibitor: As used herein, "base excision repair inhibitor" or "BER inhibitor" refers to a therapeutic agent that inhibits a base excision repair (BER) pathway, mechanism, or process.

Breakpoint: As used herein, "breakpoint" in the context of a nucleic acid fusion molecule or a corresponding sequencing read refers to a terminal nucleotide position at a junction between fused sub-sequences of the nucleic acid fusion or represented in the corresponding sequencing read. For example, a given split sequence read may include a first sub-sequence that is contiguous with, and 5' to, a second sub-sequence in that split sequence read in which the first sub-sequence maps to a first locus in a reference sequence that is non-contiguous with a second locus in that reference sequence to which the second sub-sequence maps. In this example, the first sub-sequence of the split sequence read includes a breakpoint at its 3' terminal nucleotide, while the second subsequence of the split sequence read includes a breakpoint at its 5' terminal nucleotide. In certain applications, breakpoints such as these are referred to as a "breakpoint pair."

Cancer Type: As used herein, "cancer," "cancer type" or "tumor type" refers to a type or subtype of cancer defined, e.g., by histopathology. Cancer type can be defined by any conventional criterion, such as on the basis of occurrence in a given tissue (e.g., blood cancers, central nervous system (CNS), brain cancers, lung cancers (small cell and non-small cell), skin cancers, nose cancers, throat cancers, liver cancers, bone cancers, lymphomas, pancreatic cancers, bowel cancers, rectal cancers, thyroid cancers, bladder cancers, kidney cancers, mouth cancers, stomach cancers, breast cancers, prostate cancers, ovarian cancers, lung cancers, intestinal cancers, soft tissue cancers, neuroendocrine cancers, gastroesophageal cancers, head and neck cancers, gynecological cancers, colorectal cancers, urothelial cancers, solid state cancers, heterogeneous cancers, homogenous cancers), unknown primary origin and the like, and/or of the same cell lineage (e.g., carcinoma, sarcoma, lymphoma, cholangiocarcinoma, leukemia, mesothelioma, melanoma, or glioblastoma) and/or cancers exhibiting cancer markers, such as Her2, CA15-3, CA19-9, CA-125, CEA, AFP, PSA, HCG, KRAS, BRAF, NRAS, hormone receptor and NMP-22. Cancers can also be classified by stage (e.g., stage 1, 2, 3, or 4) and whether of primary or secondary origin.

Cell-Free Nucleic Acid: As used herein, "cell-free nucleic acid" refers to nucleic acids not contained within or otherwise bound to a cell. In some embodiments, "cell-free nucleic acid" refers to nucleic acids which are not contained within or otherwise bound to a cell at the point of isolation from the subject. Cell-free nucleic acids can include, for example, all non-encapsulated nucleic acids sourced from a bodily fluid (e.g., blood, plasma, serum, urine, cerebrospinal fluid (CSF), etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), and/or fragments of any of these. Cell-free nucleic acids can be double-stranded, single-stranded, or a hybrid thereof. A cell-free nucleic acid can be released into bodily fluid through secretion or cell death processes, e.g., cellular necrosis, apoptosis, or the like. Some cell-free nucleic acids are released into bodily fluid from cancer cells, e.g., circulating tumor DNA (ctDNA). Others are released from healthy cells. CtDNA can be non-encapsulated tumor-derived fragmented DNA. Another example of cell-free nucleic acids is fetal DNA circulating freely in the maternal blood stream, also called cell-free fetal DNA (cffDNA). A cell-free nucleic acid can have one or more epigenetic modifications, for example, a cell-free nucleic acid can be acetylated, 5-methylated, ubiquitylated, phosphorylated, sumoylated, ribosylated, and/or citrullinated.

Classifier: As used herein, "classifier" generally refers to algorithm computer code that receives, as input, test data and produces, as output, a classification of the input data as belonging to one or another class (e.g., having a DNA damage repair deficiency (DDRD) or not having DDRD, tumor DNA or non-tumor DNA).

Contiguous Sequence: As used herein, "contiguous sequence" or "contig" refers to a set of overlapping nucleic acid segments that together represent a consensus region of a nucleic acid.

Copy Number Variant: As used herein, "copy number variant," "CNV," or "copy number variation" refers to a phenomenon in which sections of the genome are repeated and the number of repeats in the genome varies between individuals in the population under consideration.

Coverage: As used herein, "coverage" refers to the number of nucleic acid molecules that represent a particular base position.

De Novo Fusion Caller: As used herein, "de novo fusion caller," "fusion caller," or "de novo method" refers to the fusion caller, either DNA or RNA fusion caller, that identifies fusion events de novo, that is, without prior knowledge such as can be obtained from a database of previously known gene fusion events.

Deoxyribonucleic Acid or Ribonucleic Acid: As used herein, "deoxyribonucleic acid" or "DNA" refers a natural or modified nucleotide which has a hydrogen group at the 2'-position of the sugar moiety. DNA typically includes a chain of nucleotides comprising deoxyribonucleosides that comprise one of four types of nucleobases, namely, adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA typically includes a chain of nucleotides comprising ribonucleosides that comprise one of four types of nucleobases, namely, A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "sequence information," "nucleic acid sequence," "nucleotide sequence", "genomic sequence," "genetic sequence," or "fragment sequence," or "nucleic acid sequencing read" denotes any information or data that is indicative of the order and identity of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

Detect: As used herein, "detect," "detecting," or "detection" refers to an act of determining the existence or presence of one or more target nucleic acids (e.g., nucleic acids having targeted mutations or other markers) in a sample.

DNA Damage Repair: As used herein, "DNA damage repair" or "DDR" refers to a biochemical pathway, mechanism, or process that repairs DNA damage during the cell cycle. Direct reversal DNA damage repair mechanisms do not involve a template, as the underlying damage does not involve the breakage of a phosphodiester backbone in the affected DNA. Other DNA damage repair pathways, mechanisms, or processes do involve a template. These include single-strand damage repair mechanisms, such as base excision repair (BER), nucleotide excision repair (NER), and mismatch repair (MMR), which act to repair DNA when only one of the two strands of a given double helix has damage. Template-directed DNA repair processes also include double-strand damage repair mechanisms, such as homologous recombination (HR), microhomology-mediated end joining (MMEJ), and non-homologous end joining (NHEJ), which act to repair DNA when both strands of a given double helix are damaged (e.g., severed).

DNA Damage Repair Deficiency: As used herein, "DNA damage repair deficiency" or "DDRD" refers to a mutation or set of mutations that partially or completely disrupts a DNA damage repair pathway, mechanism, or process.

DNA Damage Repair Gene: As used herein, "DNA damage repair gene" or "DDR gene" refers to a gene that encodes a polypeptide that is involved in a DNA damage repair pathway, mechanism, or process.

Fusion Event: As used herein, "fusion event" refers to a fusion between at least two separate genes at a particular location. Example causes of a fusion event include a translocation, interstitial deletion, or chromosomal inversion event.

Gene: As used herein, "gene" refers to any segment of DNA associated with a biological function. Thus, genes include coding sequences and optionally, the regulatory sequences required for their expression. Genes also optionally include non-expressed DNA segments that, for example, form recognition sequences for other proteins.

Homologous Recombination Repair Deficiency Score: As used herein, "homologous recombination repair deficiency score" or "HRD score" refers to a value that reflects a number or other measure of mutations or sets of mutations associated with DNA Damage Repair Deficiency (DDRD) such as Homologous Recombination Repair Deficiency (HRD) observed or otherwise known to be present in one or more genomic regions of a given subject or in one or more genomic regions in a given population of subjects.

Germline Mutation: As used herein, "germline mutation" means a mutation in a germ cell and accordingly, that can be passed on to progeny.

Homologous Recombination Repair: As used herein, "homologous recombination repair" or "HRR" refers to template-directed DNA repair process that occurs during DNA replication. Typically, a region of homology on a sister chromatid functions as a template as part of the process to repair a damaged DNA strand.

Homologous Recombination Repair Deficiency: As used herein, "homologous recombination repair deficiency" or "HRD" refers to a mutation or set of mutations that partially or completely disrupts a homologous recombination repair pathway, mechanism, or process.

Homologous Recombination Repair Gene: As used herein, "homologous recombination repair gene" or "HRR gene" refers to a gene that encodes a polypeptide that is involved in a homologous recombination repair pathway, mechanism, or process.

Homozygous Deletion: As used herein, "homozygous deletion" or "biallelic inactivation" refers to a mutation or nucleic acid variant that results in the loss of both alleles of a given gene.

Hemizygous Deletion: As used herein, "hemizygous deletion" or "monoallelic inactivation" refers to a mutation or nucleic acid variant that results in the loss of one of two alleles of a given gene. A "heterozygous deletion" is a hemizygous deletion in which the original or initial two alleles of a given gene were different from one another.

Indel: As used herein, "indel" refers to mutation that involves the insertion or deletion of nucleotide positions in the genome of a subject.

Loss-Of-Function: As used herein, "loss-of-function" or "LoF" in the context of biochemical pathways, mechanisms, or processes refers to a mutation or a set of mutations (e.g., in a given sample) that renders a biochemical pathway, mechanism, or process non-functional. For example, loss-of-function (LoF) DNA damage repair deficiency (DDRD) is a mutation or a set of mutations that renders a given DNA damage repair (DDR) pathway, mechanism, or process non-functional (e.g., a base excision repair (BER) pathway, mechanism, or process, a nucleotide excision repair (NER) pathway, mechanism, or process, a mismatch repair (MMR) pathway, mechanism, or process, homologous recombination repair (HRR) pathway, mechanism, or process, a non-homologous end joining (NHEJ) pathway, mechanism, or process, and/or the like).

Loss-Of-Heterozygosity: As used herein, "loss-of-heterozygosity" or "LOH" refers to mutational event that results in the loss of one parent's contribution to a given cell or a given clonal group of cells (e.g., an entire gene and surrounding chromosomal region). LOH can be caused by, for example, gene conversion, direct deletion, mitotic recombination, deletion due to unbalanced rearrangements, or loss of a chromosome (monosomy).

Minor Allele Frequency: As used herein, "minor allele frequency" refers to the frequency at which minor alleles (e.g., not the most common allele) occurs in a given population of nucleic acids, such as a sample obtained from a subject. Genetic variants at a low minor allele frequency typically have a relatively low frequency of presence in a sample.

Mutant Allele Fraction: As used herein, "mutant allele fraction," or "MAF" refers to the fraction of nucleic acid molecules harboring an allelic alteration or mutation with respect to a reference at a given genomic position in a given sample. MAF is generally expressed as a fraction or percentage. For example, MAF is typically less than about 0.5, 0.1, 0.05, or 0.01 (i.e., less than about 50%, 10%, 5%, or 1%) of all somatic variants or alleles present at a given locus.

Maximum Mutant Allele Fraction: As used herein, "maximum mutant allele fraction," "maximum MAF," or "MAX MAF" refers to the maximum or largest MAF of all somatic variants present or observed in a given sample.

Mutation: As used herein, "mutation," "nucleic acid variant," "variant," or "genetic aberration" refers to a variation from a known reference sequence and includes mutations such as, for example, single nucleotide variants (SNVs), copy number variants or variations (CNVs)/aberrations, insertions or deletions (indels), truncation, gene fusions, transversions, translocations, frame shifts, duplications, repeat expansions, and epigenetic variants. A mutation can be a germline or somatic mutation. In some embodiments, a reference sequence for purposes of comparison is a wildtype genomic sequence of the species of the subject providing a test sample, typically the human genome. In certain cases, a mutation or variant is a "tumor-related genetic variant" that causes or at least contributes to oncogenesis.

Next Generation Sequencing: As used herein, "next generation sequencing" or "NGS" refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

Nucleic Acid Tag: As used herein, "nucleic acid tag" refers to a short nucleic acid (e.g., less than about 500, about 100, about 50 or about 10 nucleotides in length), used to label nucleic acid molecules to distinguish nucleic acids from different samples (e.g., representing a sample index), or different nucleic acid molecules in the same sample (e.g., representing a molecular tag), of different types, or which have undergone different processing. Nucleic acid tags can be single stranded, double stranded or at least partially double stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or both ends of the other nucleic acids (e.g., sample nucleic acids to be amplified and/or sequenced). Nucleic acid tags can be decoded to reveal information such as the sample of origin, form or processing of a given nucleic acid. Nucleic acid tags can also be used to enable pooling and/or parallel processing of multiple samples comprising nucleic acids bearing different nucleic acid tags and/or sample indexes in which the nucleic acids are subsequently being deconvoluted by reading the nucleic acid tags. Nucleic acid tags can also be referred to as molecular identifiers or tags, sample identifiers, index tags, and/or barcodes. Additionally or alternatively, nucleic acid tags can be used to distinguish different molecules in the same sample. This includes, for example, uniquely tagging different nucleic acid molecules in a given sample, or non-uniquely tagging such molecules. In the case of non-unique tagging applications, tags with a limited number of different sequences may be used to tag nucleic acid molecules such that different molecules can be distinguished based on, for example, start and/or stop positions where they map to a selected reference genome in combination with at least one nucleic acid tag. Typically, a sufficient number of different nucleic acid tags are used such that there is a low probability (e.g., less than about a 10%, less than about a 5%, less than about a 1%, or less than about a 0.1% chance) that any two molecules will have the same start/stop positions and also have the same nucleic acid tag. Some nucleic acid tags include multiple molecular identifiers to label samples, forms of nucleic acid molecules within a sample, and nucleic acid molecules within a form having the same start and stop positions. Such nucleic acid tags can be referenced using the exemplary form "Ali" in which the uppercase letter indicates a sample type, the Arabic numeral indicates a form of molecule within a sample, and the lowercase Roman numeral indicates a molecule within a form.

Poly ADP Ribose Polymerase Inhibitor: As used herein, "poly ADP ribose polymerase inhibitor," "PARP inhibitor," or "PARPi" refers to a therapeutic agent that inhibits the action of the enzyme poly ADP ribose polymerase (PARP).

Polynucleotide: As used herein, "polynucleotide", "nucleic acid", "nucleic acid molecule", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that in the case of DNA, "A" denotes deoxyadenosine, "C" denotes deoxycytidine, "G" denotes deoxyguanosine, and "T" denotes deoxythymidine, unless otherwise noted. The letters A, C, G, and T may be used to refer to the bases themselves, to nucleosides, or to nucleotides comprising the bases, as is standard in the art.

Prevalence: As used herein, "prevalence" in the context of nucleic acid variants refers to the degree, pervasiveness, or frequency with which a given nucleic acid variant is or was observed in a given sample (e.g., a given bodily fluid sample, a given non-bodily fluid sample, etc.) or other population (e.g., a given population of bodily fluid samples, a given population of non-bodily fluid samples, etc.).

Reference Sample: As used herein, "reference sample" or "reference cfDNA sample" refers a sample of known composition and/or having or known to have or lack specific properties (e.g., known nucleic acid variant(s), known cellular origin, known tumor fraction, known coverage, and/or the like) that is analyzed along with or compared to test samples in order to evaluate the accuracy of an analytical procedure. A reference sample dataset typically includes from at least about 25 to at least about 30,000 or more reference samples. In some embodiments, the reference sample dataset includes about 50, 75, 100, 150, 200, 300, 400, 500, 600, 700, 800, 900, 1,000, 2,500, 5,000, 7,500, 10,000, 15,000, 20,000, 25,000, 50,000, 100,000, 1,000,000, or more reference samples.

Reference Sequence: As used herein, "reference sequence" or "reference genome" refers to a known sequence used for purposes of comparison with experimentally determined sequences. For example, a known sequence can be an entire genome, a chromosome, or any segment thereof. A reference sequence typically includes at least about 20, at least about 50, at least about 100, at least about 200, at least about 250, at least about 300, at least about 350, at least about 400, at least about 450, at least about 500, at least about 1000, at least about 10,000, at least about 100,000, at least about 1,000,000, at least about 10,000,000, at least about 100,000,000, at least about 1,000,000,000, or more nucleotides. A reference sequence can align with a single contiguous sequence of a genome or chromosome or can include non-contiguous segments that align with different regions of a genome or chromosome. Exemplary reference sequences, include, for example, human genomes, such as, hG19 and hG38.

Sample: As used herein, "sample" means any biological sample capable of being analyzed by the methods and/or systems disclosed herein. In certain aspects of the present disclosure, samples are bodily fluid samples, for example, whole blood or fractions thereof, lymphatic fluid, urine, and/or cerebrospinal fluid, among other bodily fluid types from which cell-free (circulating, not contained within or otherwise bound to a cell) nucleic acids are sourced. In certain implementations, bodily fluid samples are plasma samples, which are the fluid portions of whole blood exclusive of cells, such as red and white blood cells. In some implementations, bodily fluid samples are serum samples, that is, plasma lacking fibrinogen. In some aspects of the present disclosure, samples are "non-bodily fluid samples" or "non-plasma samples," that is, biological samples other than "bodily fluid samples" such as, as cellular and/or tissue samples, from which nucleic acids other than cell-free nucleic acids are sourced.

Sensitivity: As used herein, "sensitivity" in the context of a given assay or method refers to the ability of the assay or method to detect and distinguish between targeted (e.g., nucleic acid variants) and non-targeted analytes.

Sequencing: As used herein, "sequencing" refers to any of a number of technologies used to determine the sequence (e.g., the identity and order of monomer units) of a biomolecule, e.g., a nucleic acid such as DNA or RNA. Exemplary sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performer by a gene analyzer such as, for example, gene analyzers commercially available from Illumina, Inc., Pacific Biosciences, Inc., or Applied Biosystems/Thermo Fisher Scientific, among many others.

Sequence Information: As used herein, "sequence information" in the context of a nucleic acid polymer means the order and/or identity of monomer units (e.g., nucleotides, etc.) in that polymer.

Single Nucleotide Variant: As used herein, "single nucleotide variant" or "SNV" means a mutation or variation in a single nucleotide that occurs at a specific position in the genome.

Somatic Mutation: As used herein, "somatic mutation" means a mutation in a given genome that occurs after conception. Somatic mutations can occur in any cell of the body except germ cells and accordingly, are not passed on to progeny.

Specificity: As used herein, "specificity" in the context of a diagnostic analysis or assay refers to the extent to which the analysis or assay detects an intended target analyte to the exclusion of other components of a given sample.

Status: As used herein, "status" in the context of subjects refers to one or more states of a given subject, such as whether or not the subject has DNA damage repair deficiency (DDRD) (e.g., a homologous recombination repair deficiency (HRD) and/or the like).

Subject: As used herein, "subject" or "test subject" refers to an animal, such as a mammalian species (e.g., human) or avian (e.g., bird) species, or other organism, such as a plant. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject." In some embodiments, the subject is a human who has, or is suspected of having cancer. For example, a subject can be an individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed with or suspected of having a disease, e.g., a cancer, an auto-immune disease. A "reference subject" refers to a subject known to have or lack specific properties (e.g., known DDRD or HRD status, known nucleic acid variant(s), known cellular origin, known tumor fraction, known coverage, and/or the like).

Threshold: As used herein, "threshold" refers to a separately determined value used to characterize or classify experimentally determined values. In certain embodiments, for example, "threshold value" refers to a selected value to which a quantitative value is compared in order to determine that a given target nucleic acid variant is absent at a given genetic locus.

Tumor Fraction: As used herein, "tumor fraction" refers to the estimate of the fraction of nucleic acid molecules derived from tumor in a given sample. For example, the tumor fraction of a sample can be a measure derived from the maximum mutant allele frequency (MAX MAF) of the sample or coverage of the sample, or length, epigenetic state, or other properties of the cfDNA fragments in the sample or any other selected feature of the sample. The term "MAX MAF" refers to the maximum or largest MAF of all somatic variants present in a given sample. In some embodiments, the tumor fraction of a sample is equal to the MAX MAF of the sample.

Value: As used herein, "value" or "score" generally refers to an entry in a dataset can be anything that characterizes the feature to which the value refers. This includes, without limitation, numbers, words or phrases, symbols (e.g., + or −) or degrees.

DETAILED DESCRIPTION

Introduction

DNA damage repair (DDR) is a cellular process that functions to maintain genomic integrity or stability. Defects or deficiencies in a given DDR mechanism can lead to tumorigenesis or other diseases and can be used to identify test subjects or patients that may benefit from a given targeted therapy. For example, homologous recombination repair deficiency (HRD) is a cellular phenotype that may make patients candidates for the administration of therapeutic agents, such as PARP inhibitors. To illustrate, FIG. 1 (panels A and B) are diagrams that schematically show that cells having a deficiency in a homologous recombination repair (HRR) pathway are vulnerable to increased DNA damage and have an increased sensitivity to DNA damage repair inhibitors (e.g., PARP inhibitors, etc.) and/or other therapies. As shown, normal cells (panel A) having DNA damage will often survive, even if a PARP inhibitor is administered to the patient, because the PARP inhibitor only inhibits PARP-mediated repair of single-stranded breaks (SSB). During DNA replication, these SSBs may result in double-stranded breaks (DSBs) when the DNA helix unwinds. In these normal cells, this DNA damage may be repaired via a homologous recombination (HR)-mediated repair pathway that repairs DSBs, such that the normal cells will survive. By contrast, in HR-deficient cancer cells (panel B), for example, the HR-mediated repair pathway is non-functional and accordingly, the administered PARP inhibitor will inhibit the remaining PARP-mediated repair pathway, which leads to the death of the cancer cells.

There are various classes of inactivating HRD alterations or mutations. Some of these include SNVs and/or indels in HRR genes, homozygous deletions, gene-specific LOH, copy number neutral LOH, genome-wide LOH, truncating re-arrangements, and multi-exon (long) deletions, among other alterations. In certain embodiments disclosed herein, SNVs and indels are identified using pathogenic annotation techniques, homozygous deletions, gene-specific LOH, copy number neutral LOH, and genome-wide LOH are identified using homozygous deletion/LOH CNV callers, and truncating rearrangements, and multi-exon deletions are identified using rearrangement or de novo fusion callers.

In some embodiments, the methods and related aspects disclosed herein are used to identify deficiencies in HRR pathways to guide PARP inhibitor treatment in ovarian, prostate, breast, or other cancer patients. In certain of these embodiments, the HRD workflow provides information about copy number loss, rearrangements, and pathogenic SNV and Indels in HRR genes to identify samples with HRD and thus, candidates for targeted therapies, including PARP inhibitors. In some of these embodiments, this is achieved through system modules, such as SNV/indel, fusion, and CNV callers. In some embodiments, reports generated as output of these processes identify values for the variant types that indicate loss-of-function (LoF) of relevant HRR genes.

Essentially any DDR (e.g., HRR) gene or biomarker may be evaluated in a given sample for an associated mutation, which may render a corresponding DDR (e.g., HRR) pathway defective or non-functional. This information can be used as selection criteria for the administration of targeted therapies (e.g., PARP inhibitors, BER inhibitors, etc.) to patients. In certain embodiments, the targeted therapies may comprise a PARP inhibitor. Examples of PARP inhibitors that may be administered include one or more of: VELI-PARIB, OLAPARIB, TALAZOPARIB, RUCAPARIB, NIRAPARIB, PAMIPARIB, CEP 9722 (Cephalon), E7016 (Eisai), E7449 (Eisai, a PARP ½ and tankyrase ½ inhibitor), or 3-Aminobenzamide. In some embodiments, the targeted therapies may comprise at least one base excision repair (BER) inhibitor. For example, OLAPARIB may inhibit BIR. In certain embodiments, the targeted therapies may comprise combination of a PARP inhibitor and radiotherapy. In an embodiment, the combination of a PARP inhibitor and radiotherapy would permit the PARP inhibitor to lead to formation of double strand breaks from the single-strand breaks generated by the radiotherapy in tumor tissue (e.g., tissue with BRCA1/BRCA2 mutations). This combination can provide more powerful therapy per radiation dose. Essentially any number of genes is optionally evaluated using the methods and related aspects of the present disclosure. In some embodiments, for example, sets of DDR genes (e.g., HRR genes) targeted for analysis, as described herein, include at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 100, 1,000, 10,000, or more genes. A non-exhaustive list of HRR genes, one or more of which are optionally selected for evaluation using the methods and related aspects disclosed herein is provided in Table 1.

TABLE 1

| ATM | ATR | BARD1 | BRCA1 | BRCA2 |
|---|---|---|---|---|
| BRIP1 | CDK12 | CHEK1 | CHEK2 | FANCA |
| FANCL | NBN | PALB2 | RAD51 | RAD51B |
| RAD51C | RAD51D | RAD54L | HDAC2 | MRE11 |
| PPP2R2A | XRCC5 | WRN | MLH1 | FANCC |
| BAP1 | XRCC2 | XRCC3 | RAD50 | |

Exemplary sets of HRR genes that may be evaluated as described herein to identify patients that are candidates for specific targeted therapies are listed in Table 2.

TABLE 2

| Targeted Therapy | HRR Genes |
|---|---|
| OLAPARIB (Merck & Co.) | ATM, BRCA1, BRCA2, CDK12, BARD1, BRIP1, CHEK1, CHEK2, FANCL, PALB2, RAD51B, RAD51C, RAD51D, RAD54L, and PPP2R2A |
| RUCAPARIB (Clovis Oncology) | ATM, BRCA1, BRCA2, CDK12, BARD1, BRIP1, CHEK2, FANCA, NBN, PALB2, RAD51, RAD51B, RAD51C, RAD51D, and RAD54L |
| TALAZOPARIB (Pfizer Inc.) | ATM, BRCA1, BRCA2, CDK12, and PALB2 |
| NIRAPARIB (GSK) | ATM, BRCA1, BRCA2, BRIP1, CHEK2, FANCA, HDAC2, and PALB2 |
| RUCAPARIB (Bristol-Myers Squibb Company) | ATM, BRCA1, BRCA2, CDK12, CHEK2, and PALB2 |
| NIRAPARIB (Janssen Pharmaceutical Companies) | ATM, BRCA1, BRCA2, ATR, BRIP1, CHEK2, FANCA, HDAC2, and PALB2 |

Exemplary Systems and Methods

Figure 2:
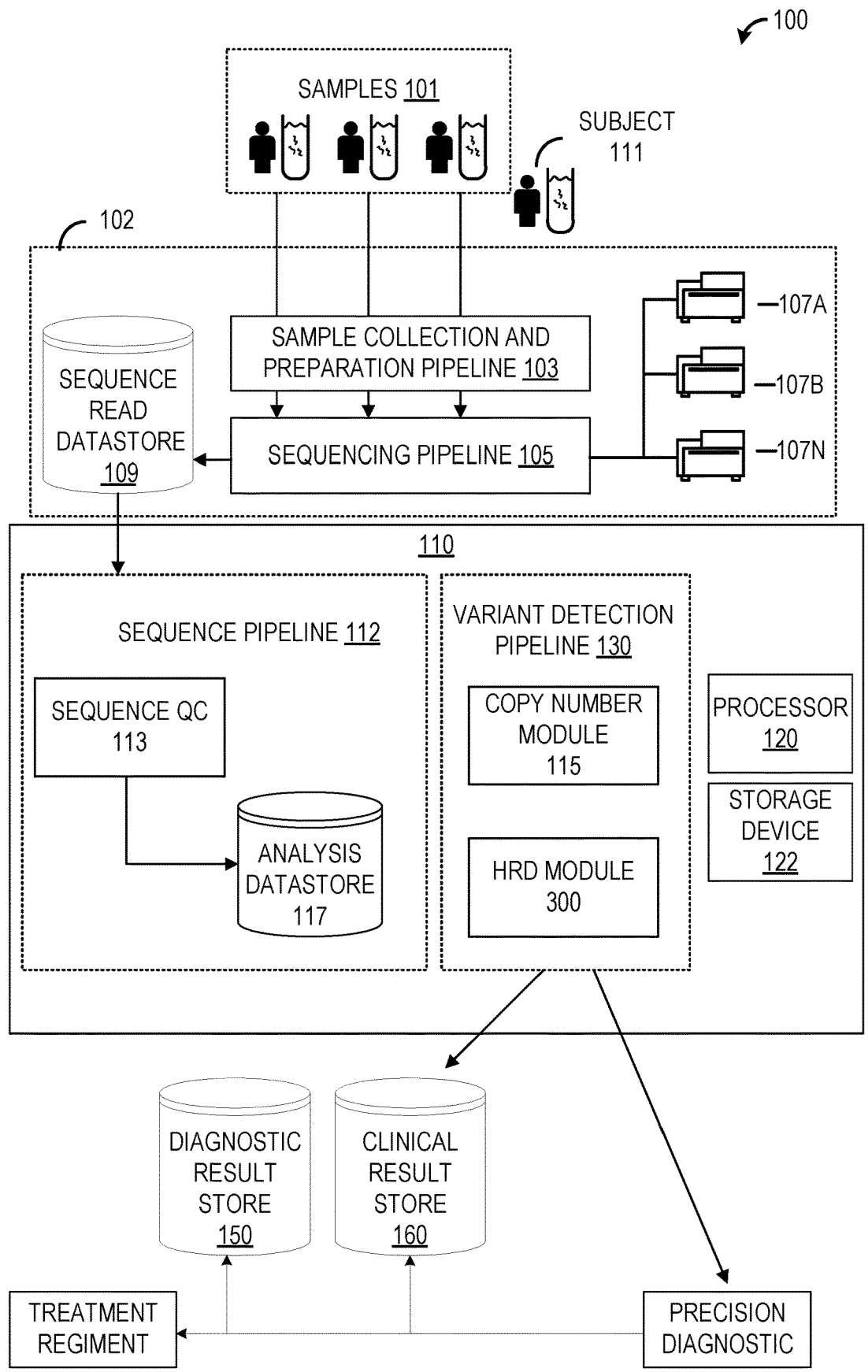
FIG. 2 illustrates an example of a system that includes a HRD scoring module according to an embodiment of the present disclosure.

FIG. 2 illustrates an example of a system 100 for determining a DNA damage repair deficiency (DDRD) status (e.g., a HRD status or the like) of a test subject 111, according to an embodiment of the present disclosure. The system 100 may process one or more samples 101 from the subject 111 to generate sequence reads for variant detection and DDRD status determination. The system 100 may include a laboratory system 102, a computer system 110, and/or other components. It should be noted that the laboratory system 102 and the computer system 110 may be remote from one another, and connected to one another through a computer network (not illustrated). The laboratory system 102 may include a sample collection and preparation pipeline 103, a sequencing pipeline 105, a sequence read datastore 109, and/or other components. The sequencing pipeline 105 may include one or more sequencing devices 107 (illustrated in FIG. 2 as sequencing devices 107a . . . n).

The methods of this disclosure may have a wide variety of uses in the manipulation, preparation, identification, quantification, and/or analysis of cell-free nucleic acids. As shown in FIG. 2, the sample collection and preparation pipeline 103 may include obtaining cfDNA reference samples 101 from one or more reference subjects and a cfDNA test sample 111 from a test subject. As described herein, a polynucleotide can comprise any type of nucleic acid, such as DNA and/or RNA. For example, if a polynucleotide is DNA, it can be genomic DNA, complementary DNA (cDNA), or any other deoxyribonucleic acid. A polynucleotide can also be a cell-free nucleic acid such as cell-free DNA (cfDNA). For example, the polynucleotide can be circulating cfDNA. Circulating cfDNA may comprise DNA shed from bodily cells via apoptosis or necrosis. cfDNA shed via apoptosis or necrosis may originate from normal (e.g. healthy) bodily cells. Where there is abnormal tissue growth, such as for cancer, tumor DNA may be shed. The circulating cfDNA can comprise circulating tumor DNA (ctDNA).

i. Samples

Isolation and extraction of cell free polynucleotides may be performed through collection of samples using a variety of techniques. A sample can be any biological sample isolated from a subject. Samples can include body tissues, whole blood, platelets, serum, plasma, stool, red blood cells, white blood cells or leucocytes, endothelial cells, tissue biopsies (e.g., biopsies from known or suspected solid tumors), cerebrospinal fluid, synovial fluid, lymphatic fluid, ascites fluid, interstitial or extracellular fluid (e.g., fluid from intercellular spaces), gingival fluid, crevicular fluid, bone marrow, pleural effusions, cerebrospinal fluid, saliva, mucous, sputum, semen, sweat, urine. Samples are preferably body fluids, particularly blood and fractions thereof, and urine. Such samples include nucleic acids shed from tumors. The nucleic acids can include DNA and RNA and can be in double and single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid sample for analysis is plasma or serum containing cell-free nucleic acids, e.g., cell-free DNA (cfDNA).

In some embodiments, the sample volume of body fluid taken from a subject depends on the desired read depth for sequenced regions. Exemplary volumes are about 0.4-40 ml, about 5-20 ml, about 10-20 ml. For example, the volume can be about 0.5 ml, about 1 ml, about 5 ml, about 10 ml, about 20 ml, about 30 ml, about 40 ml, or more milliliters. A volume of sampled plasma is typically between about 5 ml to about 20 ml.

The sample can comprise various amounts of nucleic acid. Typically, the amount of nucleic acid in a given sample is equated with multiple genome equivalents. For example, a sample of about 30 ng DNA can contain about 10,000 (104) haploid human genome equivalents and, in the case of cfDNA, about 200 billion (2×1011) individual polynucleotide molecules. Similarly, a sample of about 100 ng of DNA can contain about 30,000 haploid human genome equivalents and, in the case of cfDNA, about 600 billion individual molecules.

In some embodiments, a sample comprises nucleic acids from different sources, e.g., from cells and from cell-free sources (e.g., blood samples, etc.). Typically, a sample includes nucleic acids carrying mutations. For example, a sample optionally comprises DNA carrying germline mutations and/or somatic mutations. Typically, a sample comprises DNA carrying cancer-associated mutations (e.g., cancer-associated somatic mutations). In some embodiments of the present disclosure, cell free nucleic acids in a subject may derive from a tumor. For example cell-free DNA isolated from a subject can comprise ctDNA.

Exemplary amounts of cell-free nucleic acids in a sample before amplification typically range from about 1 femtogram (fg) to about 1 microgram (μg), e.g., about 1 picogram (pg) to about 200 nanogram (ng), about 1 ng to about 100 ng, about 10 ng to about 1000 ng. In some embodiments, a sample includes up to about 600 ng, up to about 500 ng, up to about 400 ng, up to about 300 ng, up to about 200 ng, up to about 100 ng, up to about 50 ng, or up to about 20 ng of cell-free nucleic acid molecules. Optionally, the amount is at least about 1 fg, at least about 10 fg, at least about 100 fg, at least about 1 pg, at least about 10 pg, at least about 100 pg, at least about 1 ng, at least about 10 ng, at least about 100 ng, at least about 150 ng, or at least about 200 ng of cell-free nucleic acid molecules. In certain embodiments, the amount is up to about 1 fg, about 10 fg, about 100 fg, about 1 pg, about 10 pg, about 100 pg, about 1 ng, about 10 ng, about 100 ng, about 150 ng, or about 200 ng of cell-free nucleic acid molecules. In some embodiments, methods include obtaining between about 1 fg to about 200 ng cell-free nucleic acid molecules from samples.

Cell-free nucleic acids typically have a size distribution of between about 100 nucleotides in length and about 500 nucleotides in length, with molecules of about 110 nucleotides in length to about 230 nucleotides in length representing about 90% of molecules in the sample, with a mode of about 168 nucleotides length and a second minor peak in a range between about 240 to about 440 nucleotides in length. In certain embodiments, cell-free nucleic acids are from about 160 to about 180 nucleotides in length, or from about 320 to about 360 nucleotides in length, or from about 440 to about 480 nucleotides in length.

In some embodiments, cell-free nucleic acids are isolated from bodily fluids through a partitioning step in which cell-free nucleic acids, as found in solution, are separated from intact cells and other non-soluble components of the bodily fluid. In some of these embodiments, partitioning includes techniques such as centrifugation or filtration. Alternatively, cells in bodily fluids are lysed, and cell-free and cellular nucleic acids processed together. Generally, after addition of buffers and wash steps, cell-free nucleic acids are precipitated with, for example, an alcohol. In certain embodiments, additional clean up steps are used, such as silica-based columns to remove contaminants or salts. Non-specific bulk carrier nucleic acids, for example, are optionally added throughout the reaction to optimize certain aspects of the exemplary procedure, such as yield. After such processing, samples typically include various forms of nucleic acids including double-stranded DNA, single-stranded DNA and/or single-stranded RNA. Optionally, single stranded DNA and/or single stranded RNA are converted to double stranded forms so that they are included in subsequent processing and analysis steps. Additional details regarding cfDNA partitioning and related analysis of epigenetic modifications that are optionally adapted for use in performing the methods disclosed herein are described in, for example, WO 2018/119452, filed Dec. 22, 2017, which is incorporated by reference.

ii. Nucleic Acid Tags

In certain embodiments, tags providing molecular identifiers or barcodes are incorporated into or otherwise joined to adapters by chemical synthesis, ligation, or overlap extension PCR, among other methods as part of the sample collection and preparation pipeline 103. In some embodiments, the assignment of unique or non-unique identifiers, or molecular barcodes in reactions follows methods and utilizes systems described in, for example, US patent applications 20010053519, 20030152490, 20110160078, and U.S. Pat. Nos. 6,582,908, 7,537,898, and 9,598,731, which are each incorporated by reference.

Tags are linked to sample nucleic acids randomly or non-randomly. In some embodiments, tags are introduced at an expected ratio of identifiers (e.g., a combination of unique and/or non-unique barcodes) to microwells. For example, the identifiers may be loaded so that more than about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 identifiers are loaded per genome sample. In some embodiments, the identifiers are loaded so that less than about 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 identifiers are loaded per genome sample. In certain embodiments, the average number of identifiers loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 identifiers per genome sample. The identifiers are generally unique and/or non-unique.

One exemplary format uses from about 2 to about 1,000,000 different tags, or from about 5 to about 150 different tags, or from about 20 to about 50 different tags, ligated to both ends of a target nucleic acid molecule. For 20-50×20-50 tags, a total of 400-2500 tags are created. Such numbers of tags are typically sufficient for different molecules having the same start and stop points to have a high probability (e.g., at least 94%, 99.5%, 99.99%, 99.999%) of receiving different combinations of tags.

In some embodiments, identifiers are predetermined, random, or semi-random sequence oligonucleotides. In other embodiments, a plurality of barcodes may be used such that barcodes are not necessarily unique to one another in the plurality. In these embodiments, barcodes are generally attached (e.g., by ligation or PCR amplification) to individual molecules such that the combination of the barcode and the sequence it may be attached to creates a unique sequence that may be individually tracked. As described herein, detection of non-uniquely tagged barcodes in combination with sequence data of beginning (start) and end (stop) portions of sequence reads typically allows for the assignment of a unique identity to a particular molecule. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

iii. Nucleic Acid Amplification

Sample nucleic acids flanked by adapters are typically amplified by PCR and other amplification methods using nucleic acid primers binding to primer binding sites in adapters flanking a DNA molecule to be amplified as part of the sample collection and preparation pipeline 103. In some embodiments, amplification methods involve cycles of extension, denaturation and annealing resulting from thermocycling, or can be isothermal as, for example, in transcription mediated amplification. Other exemplary amplification methods that are optionally utilized, include the ligase chain reaction, strand displacement amplification, nucleic acid sequence-based amplification, and self-sustained sequence-based replication, among other approaches.

One or more rounds of amplification cycles are generally applied to introduce molecular tags and/or sample indexes/tags to a nucleic acid molecule using conventional nucleic acid amplification methods. The amplifications are typically conducted in one or more reaction mixtures. Molecular tags and sample indexes/tags are optionally introduced simultaneously, or in any sequential order. In some embodiments, molecular tags and sample indexes/tags are introduced prior to and/or after sequence capturing steps are performed. In some embodiments, only the molecular tags are introduced prior to probe capturing and the sample indexes/tags are introduced after sequence capturing steps are performed. In certain embodiments, both the molecular tags and the sample indexes/tags are introduced prior to performing probe-based capturing steps. In some embodiments, the sample indexes/tags are introduced after sequence capturing steps are performed. Typically, sequence capturing protocols involve introducing a single-stranded nucleic acid molecule complementary to a targeted nucleic acid sequence, e.g., a coding sequence of a genomic region and mutation of such region associated with a cancer type. Typically, the amplification reactions generate a plurality of non-uniquely or uniquely tagged nucleic acid amplicons with molecular tags and sample indexes/tags at size ranging from about 200 nucleotides (nt) to about 700 nt, from 250 nt to about 350 nt, or from about 320 nt to about 550 nt. In some embodiments, the amplicons have a size of about 300 nt. In some embodiments, the amplicons have a size of about 500 nt.

iv. Nucleic Acid Enrichment

In some embodiments, sequences are enriched prior to sequencing the nucleic acids as part of the sample collection and preparation pipeline 103. Enrichment is optionally performed for specific target regions or nonspecifically ("target sequences"). In some embodiments, targeted regions of interest may be enriched with nucleic acid capture probes ("baits") selected for one or more bait set panels using a differential tiling and capture scheme. A differential tiling and capture scheme generally uses bait sets of different relative concentrations to differentially tile (e.g., at different "resolutions") across genomic sections associated with the baits, subject to a set of constraints (e.g., sequencer constraints such as sequencing load, utility of each bait, etc.), and capture the targeted nucleic acids at a desired level for downstream sequencing. These targeted genomic sections of interest optionally include natural or synthetic nucleotide sequences of the nucleic acid construct. In some embodiments, biotin-labeled beads with probes to one or more sections of interest can be used to capture target sequences, and optionally followed by amplification of those sections, to enrich for the regions of interest.

Sequence capture typically involves the use of oligonucleotide probes that hybridize to the target nucleic acid sequence. In certain embodiments, a probe set strategy involves tiling the probes across a section of interest. Such probes can be, for example, from about 60 to about 120 nucleotides in length. The set can have a depth of about 2×, 3×, 4×, 5×, 6×, 8×, 9×, 10×, 15×, 20×, 50× or more. The effectiveness of sequence capture generally depends, in part, on the length of the sequence in the target molecule that is complementary (or nearly complementary) to the sequence of the probe.

b. Nucleic Acid Sequencing

As shown in FIG. 2, after extraction and isolation of cfDNA from samples via the sample collection and preparation pipeline 103, the cfDNA may be sequenced via the sequencing pipeline 105 including one or more sequencing devices 107. Sample nucleic acids, optionally flanked by adapters, with or without prior amplification are generally subject to sequencing. Sequencing methods or commercially available formats that are optionally utilized include, for example, Sanger sequencing, high-throughput sequencing, bisulfite sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

The sequencing reactions can be performed on one more nucleic acid fragment types or sections known to contain markers of cancer or of other diseases. The sequencing reactions can also be performed on any nucleic acid fragment present in the sample. The sequence reactions may provide for sequence coverage of the genome of at least about 5%, 10%, 15%, 20%, 25%, 30%, 40%, 50%, 60%, 70%, 80%, 90%, 95%, 99%, 99.9% or 100% of the genome. In other cases, sequence coverage of the genome may be less than about 5%, 10%, 15%, 20%, 25%, 30%, 40%, 50%, 60%, 70%, 80%, 90%, 95%, 99%, 99.9% or 100% of the genome.

Simultaneous sequencing reactions may be performed using multiplex sequencing techniques. In some embodiments, cell-free polynucleotides are sequenced with at least about 1000, 2000, 3000, 4000, 5000, 6000, 7000, 8000, 9000, 10000, 50000, or 100,000 sequencing reactions. In other embodiments, cell-free polynucleotides are sequenced with less than about 1000, 2000, 3000, 4000, 5000, 6000, 7000, 8000, 9000, 10000, 50000, or 100,000 sequencing reactions. Sequencing reactions are typically performed sequentially or simultaneously. Subsequent data analysis is generally performed on all or part of the sequencing reactions. In some embodiments, data analysis is performed on at least about 1000, 2000, 3000, 4000, 5000, 6000, 7000, 8000, 9000, 10000, 50000, or 100,000 sequencing reactions. In other embodiments, data analysis may be performed on less than about 1000, 2000, 3000, 4000, 5000, 6000, 7000, 8000, 9000, 10000, 50000, or 100,000 sequencing reactions. An exemplary read depth is from about 1000 to about 50000 reads per locus (base position).

In some embodiments, a nucleic acid population is prepared for sequencing by enzymatically forming blunt-ends on double-stranded nucleic acids with single-stranded overhangs at one or both ends. In these embodiments, the population is typically treated with an enzyme having a 5'-3' DNA polymerase activity and a 3'-5' exonuclease activity in the presence of the nucleotides (e.g., A, C, G and T or U). Exemplary enzymes or catalytic fragments thereof that are optionally used include Klenow large fragment and T4 polymerase. At 5' overhangs, the enzyme typically extends the recessed 3' end on the opposing strand until it is flush with the 5' end to produce a blunt end. At 3' overhangs, the enzyme generally digests from the 3' end up to and sometimes beyond the 5' end of the opposing strand. If this digestion proceeds beyond the 5' end of the opposing strand, the gap can be filled in by an enzyme having the same polymerase activity that is used for 5' overhangs. The formation of blunt-ends on double-stranded nucleic acids facilitates, for example, the attachment of adapters and subsequent amplification.

In some embodiments, nucleic acid populations are subject to additional processing, such as the conversion of single-stranded nucleic acids to double-stranded and/or conversion of RNA to DNA. These forms of nucleic acid are also optionally linked to adapters and amplified.

With or without prior amplification, nucleic acids subject to the process of forming blunt-ends described above, and optionally other nucleic acids in a sample, can be sequenced to produce sequenced nucleic acids. A sequenced nucleic acid can refer either to the sequence of a nucleic acid (i.e., sequence information) or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some embodiments, double-stranded nucleic acids with single-stranded overhangs in a sample after blunt-end formation are linked at both ends to adapters including barcodes, and the sequencing determines nucleic acid sequences as well as in-line barcodes introduced by the adapters. The blunt-end DNA molecules are optionally ligated to a blunt end of an at least partially double-stranded adapter (e.g., a Y shaped or bell-shaped adapter). Alternatively, blunt ends of sample nucleic acids and adapters can be tailed with complementary nucleotides to facilitate ligation (e.g., sticky end ligation).

The nucleic acid sample is typically contacted with a sufficient number of adapters such that there is a low probability (e.g., <1 or 0.1%) that any two copies of the same nucleic acid receive the same combination of adapter barcodes from the adapters linked at both ends. The use of adapters in this manner permits identification of families of nucleic acid sequences with the same start and stop points on a reference nucleic acid and linked to the same combination of barcodes. Such a family represents sequences of amplification products of a nucleic acid in the sample before amplification. The sequences of family members can be compiled to derive consensus nucleotide(s) or a complete consensus sequence for a nucleic acid molecule in the original sample, as modified by blunt end formation and adapter attachment. In other words, the nucleotide occupying a specified position of a nucleic acid in the sample is determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand are converted to their complement for purposes of compiling all sequences to derive consensus nucleotide(s) or sequences. Some families include only a single member sequence. In this case, this sequence can be taken as the sequence of a nucleic acid in the sample before amplification. Alternatively, families with only a single member sequence can be eliminated from subsequent analysis.

Additional details regarding nucleic acid sequencing, including the formats and applications described herein are also provided in, for example, Levy et al., Annual Review of Genomics and Human Genetics, 17: 95-115 (2016), Liu et al., J. of Biomedicine and Biotechnology, Volume 2012, Article ID 251364:1-11 (2012), Voelkerding et al., Clinical Chem., 55: 641-658 (2009), MacLean et al., Nature Rev. Microbiol., 7: 287-296 (2009), Astier et al., J Am Chem Soc., 128(5):1705-10 (2006), U.S. Pat. Nos. 6,210,891, 6,258,568, 6,833,246, 7,115,400, 6,969,488, 5,912,148, 6,130,073, 7,169,560, 7,282,337, 7,482,120, 7,501,245, 6,818,395, 6,911,345, 7,501,245, 7,329,492, 7,170,050, 7,302,146, 7,313,308, and 7,476,503, which are each incorporated by reference in their entirety.

i. Sequencing Panel

To improve the likelihood of detecting genomic regions of interest and optionally, tumor indicating mutations, the sections of DNA sequenced may comprise a panel of genes or genomic sections that comprise known genomic regions. Selection of a limited section for sequencing (e.g., a limited panel) can reduce the total sequencing needed (e.g., a total amount of nucleotides sequenced). A sequencing panel can target a plurality of different genes or regions, for example, to detect a single cancer, a set of cancers, or all cancers. Alternatively, DNA may be sequenced by whole genome sequencing (WGS) or other unbiased sequencing method without the use of a sequencing panel. Examples of suitable panel and targets for use in panels can be found in the epigenetic targets described in International Application WO2020160414, filed Jan. 31, 2020, which is incorporated by reference in its entirety.

In some aspects, a panel that targets a plurality of different genes or genomic regions (e.g., transcriptional factor binding regions, distal regulatory elements (DREs), repetitive elements, intron-exon junctions, transcriptional start sites (TSSs), and/or the like) is selected such that a determined proportion of subjects having a cancer exhibits a genetic variant or tumor marker in one or more different genes in the panel. The panel may be selected to limit a region for sequencing to a fixed number of base pairs. The panel may be selected to sequence a desired amount of DNA. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity, and/or a theoretical accuracy for detecting one or more genetic variants in a sample.

HRR genes included in this panel may comprise one or more of: ATM, ATR, BAP1, BARD1, BRCA1, BRCA2, BRIP1, CDK12, CHEK1, CHEK2, FANCA, FANCL, HDAC2, MRE11, NBN, PALB2, RAD50, RAD51, RAD51B, RAD51C, RAD51D, RAD54L, XRCC2, XRCC3.

Probes for detecting the panel of regions can include those for detecting genomic regions of interest (hotspot regions) as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models. The panel can comprise a plurality of subpanels, including subpanels for identifying tissue of origin (e.g., use of published literature to define 50-100 baits representing genes with most diverse transcription profile across tissues (not necessarily promoters)), whole genome scaffold (e.g., for identifying ultra-conservative genomic content and tiling sparsely across chromosomes with handful of probes for copy number base lining purposes), transcription start site (TSS)/CpG islands (e.g., for capturing differential methylated regions (e.g., Differentially Methylated Regions (DMRs)) in for example in promoters of tumor suppressor genes (e.g., SEPT9/VIM in colorectal cancer)). In some embodiments, markers for a tissue of origin are tissue-specific epigenetic markers.

In some embodiments, the one or more regions in the panel comprise one or more loci from one or a plurality of genes for detecting residual cancer after surgery. This detection can be earlier than is possible for existing methods of cancer detection. In some embodiments, the one or more genomic locations in the panel comprise one or more loci from one or a plurality of genes for detecting cancer in a high-risk patient population. For example, smokers have much higher rates of lung cancer than the general population. Moreover, smokers can develop other lung conditions that make cancer detection more difficult, such as the development of irregular nodules in the lungs. In some embodiments, the methods described herein detect cancer in high risk patients earlier than is possible for existing methods of cancer detection.

A genomic location may be selected for inclusion in a sequencing panel based on a number of subjects with a cancer that have a tumor marker in that gene or region. A genomic location may be selected for inclusion in a sequencing panel based on prevalence of subjects with a cancer and a tumor marker present in that gene. Presence of a tumor marker in a region may be indicative of a subject having cancer.

In some instances, the panel may be selected using information from one or more databases. The information regarding a cancer may be derived from cancer tumor biopsies or cfDNA assays. A database may comprise information describing a population of sequenced tumor samples. A database may comprise information about mRNA expression in tumor samples. A databased may comprise information about regulatory elements or genomic regions in tumor samples. The information relating to the sequenced tumor samples may include the frequency various genetic variants and describe the genes or regions in which the genetic variants occur. The genetic variants may be tumor markers. A non-limiting example of such a database is COSMIC. COSMIC is a catalogue of somatic mutations found in various cancers. For a particular cancer, COSMIC ranks genes based on frequency of mutation. A gene may be selected for inclusion in a panel by having a high frequency of mutation within a given gene. For instance, COSMIC indicates that 33% of a population of sequenced breast cancer samples have a mutation in TP53 and 22% of a population of sampled breast cancers have a mutation in KRAS. Other ranked genes, including APC, have mutations found only in about 4% of a population of sequenced breast cancer samples. TP53 and KRAS may be included in a sequencing panel based on having relatively high frequency among sampled breast cancers (compared to APC, for example, which occurs at a frequency of about 4%). COSMIC is provided as a non-limiting example, however, any database or set of information may be used that associates a cancer with tumor marker located in a gene or genetic region. In another example, as provided by COSMIC, of 1156 biliary tract cancer samples, 380 samples (33%) carried mutations in TP53. Several other genes, such as APC, have mutations in 4-8% of all samples. Thus, TP53 may be selected for inclusion in the panel based on a relatively high frequency in a population of biliary tract cancer samples.

A gene or genomic section may be selected for a panel where the frequency of a tumor marker is significantly greater in sampled tumor tissue or circulating tumor DNA than found in a given background population. A combination of genomic locations may be selected for inclusion of a panel such that at least a majority of subjects having a cancer may have a tumor marker or genomic region present in at least one of the genomic location or genes in the panel. The combination of genomic location may be selected based on data indicating that, for a particular cancer or set of cancers, a majority of subjects have one or more tumor markers in one or more of the selected regions. For example, to detect cancer 1, a panel comprising regions A, B, C, and/or D may be selected based on data indicating that 90% of subjects with cancer 1 have a tumor marker in regions A, B, C, and/or D of the panel. Alternately, tumor markers may be shown to occur independently in two or more regions in subjects having a cancer such that, combined, a tumor marker in the two or more regions is present in a majority of a population of subjects having a cancer. For example, to detect cancer 2, a panel comprising regions X, Y, and Z may be selected based on data indicating that 90% of subjects have a tumor marker in one or more regions, and in 30% of such subjects a tumor marker is detected only in region X, while tumor markers are detected only in regions Y and/or Z for the remainder of the subjects for whom a tumor marker was detected. Tumor markers present in one or more genomic locations previously shown to be associated with one or more cancers may be indicative of or predictive of a subject having cancer if a tumor marker is detected in one or more of those regions 50% or more of the time. Computational approaches such as models employing conditional probabilities of detecting cancer given a cancer frequency for a set of tumor markers within one or more regions may be used to predict which regions, alone or in combination, may be predictive of cancer. Other approaches for panel selection involve the use of databases describing information from studies employing comprehensive genomic profiling of tumors with large panels and/or whole genome sequencing (WGS, RNA-seq, Chip-seq, bisulfate sequencing, ATAC-seq, and others). Information gleaned from literature may also describe pathways commonly affected and mutated in certain cancers. Panel selection may be further informed by the use of ontologies describing genetic information.

Genes included in the panel for sequencing can include the fully transcribed region, the promoter region, enhancer regions, regulatory elements, and/or downstream sequence. To further increase the likelihood of detecting tumor indicating mutations only exons may be included in the panel. The panel can comprise all exons of a selected gene, or only one or more of the exons of a selected gene. The panel may comprise of exons from each of a plurality of different genes. The panel may comprise at least one exon from each of the plurality of different genes.

In some aspects, a panel of exons from each of a plurality of different genes is selected such that a determined proportion of subjects having a cancer exhibit a genetic variant in at least one exon in the panel of exons.

At least one full exon from each different gene in a panel of genes may be sequenced. The sequenced panel may comprise exons from a plurality of genes. The panel may comprise exons from 2 to 100 different genes, from 2 to 70 genes, from 2 to 50 genes, from 2 to 30 genes, from 2 to 15 genes, or from 2 to 10 genes.

A selected panel may comprise a varying number of exons. The panel may comprise from 2 to 3000 exons. The panel may comprise from 2 to 1000 exons. The panel may comprise from 2 to 500 exons. The panel may comprise from 2 to 100 exons. The panel may comprise from 2 to 50 exons. The panel may comprise no more than 300 exons. The panel may comprise no more than 200 exons. The panel may comprise no more than 100 exons. The panel may comprise no more than 50 exons. The panel may comprise no more than 40 exons. The panel may comprise no more than 30 exons. The panel may comprise no more than 25 exons. The panel may comprise no more than 20 exons. The panel may comprise no more than 15 exons. The panel may comprise no more than 10 exons. The panel may comprise no more than 9 exons. The panel may comprise no more than 8 exons. The panel may comprise no more than 7 exons.

The panel may comprise one or more exons from a plurality of different genes. The panel may comprise one or more exons from each of a proportion of the plurality of different genes. The panel may comprise at least two exons from each of at least 25%, 50%, 75% or 90% of the different genes. The panel may comprise at least three exons from each of at least 25%, 50%, 75% or 90% of the different genes. The panel may comprise at least four exons from each of at least 25%, 50%, 75% or 90% of the different genes.

The sizes of the sequencing panel may vary. A sequencing panel may be made larger or smaller (in terms of nucleotide size) depending on several factors including, for example, the total amount of nucleotides sequenced or a number of unique molecules sequenced for a particular region in the panel. The sequencing panel can be sized 5 kb to 50 kb. The sequencing panel can be 10 kb to 30 kb in size. The sequencing panel can be 12 kb to 20 kb in size. The sequencing panel can be 12 kb to 60 kb in size. The sequencing panel can be at least 10 kb, 12 kb, 15 kb, 20 kb, 25 kb, 30 kb, 35 kb, 40 kb, 45 kb, 50 kb, 60 kb, 70 kb, 80 kb, 90 kb, 100 kb, 110 kb, 120 kb, 130 kb, 140 kb, or 150 kb in size. The sequencing panel may be less than 100 kb, 90 kb, 80 kb, 70 kb, 60 kb, or 50 kb in size.

The panel selected for sequencing can comprise at least 1, 5, 10, 15, 20, 25, 30, 40, 50, 60, 80, or 100 genomic locations (e.g., that each include genomic regions of interest). In some cases, the genomic locations in the panel are selected that the size of the locations are relatively small. In some cases, the regions in the panel have a size of about 10 kb or less, about 8 kb or less, about 6 kb or less, about 5 kb or less, about 4 kb or less, about 3 kb or less, about 2.5 kb or less, about 2 kb or less, about 1.5 kb or less, or about 1 kb or less or less. In some cases, the genomic locations in the panel have a size from about 0.5 kb to about 10 kb, from about 0.5 kb to about 6 kb, from about 1 kb to about 11 kb, from about 1 kb to about 15 kb, from about 1 kb to about 20 kb, from about 0.1 kb to about 10 kb, or from about 0.2 kb to about 1 kb. For example, the regions in the panel can have a size from about 0.1 kb to about 5 kb.

The panel selected herein can allow for deep sequencing that is sufficient to detect low-frequency genetic variants (e.g., in cell-free nucleic acid molecules obtained from a sample). An amount of genetic variants in a sample may be referred to in terms of the minor allele frequency for a given genetic variant. The minor allele frequency may refer to the frequency at which minor alleles (e.g., not the most common allele) occurs in a given population of nucleic acids, such as a sample. Genetic variants at a low minor allele frequency may have a relatively low frequency of presence in a sample. In some cases, the panel allows for detection of genetic variants at a minor allele frequency of at least 0.0001%, 0.001%, 0.005%, 0.01%, 0.05%, 0.1%, or 0.5%. The panel can allow for detection of genetic variants at a minor allele frequency of 0.001% or greater. The panel can allow for detection of genetic variants at a minor allele frequency of 0.01% or greater. The panel can allow for detection of genetic variant present in a sample at a frequency of as low as 0.0001%, 0.001%, 0.005%, 0.01%, 0.025%, 0.05%, 0.075%, 0.1%, 0.25%, 0.5%, 0.75%, or 1.0%. The panel can allow for detection of tumor markers present in a sample at a frequency of at least 0.0001%, 0.001%, 0.005%, 0.01%, 0.025%, 0.05%, 0.075%, 0.1%, 0.25%, 0.5%, 0.75%, or 1.0%. The panel can allow for detection of tumor markers at a frequency in a sample as low as 1.0%. The panel can allow for detection of tumor markers at a frequency in a sample as low as 0.75%. The panel can allow for detection of tumor markers at a frequency in a sample as low as 0.5%. The panel can allow for detection of tumor markers at a frequency in a sample as low as 0.25%. The panel can allow for detection of tumor markers at a frequency in a sample as low as 0.1%. The panel can allow for detection of tumor markers at a frequency in a sample as low as 0.075%. The panel can allow for detection of tumor markers at a frequency in a sample as low as 0.05%. The panel can allow for detection of tumor markers at a frequency in a sample as low as 0.025%. The panel can allow for detection of tumor markers at a frequency in a sample as low as 0.01%. The panel can allow for detection of tumor markers at a frequency in a sample as low as 0.005%. The panel can allow for detection of tumor markers at a frequency in a sample as low as 0.001%. The panel can allow for detection of tumor markers at a frequency in a sample as low as 0.0001%. The panel can allow for detection of tumor markers in sequenced cfDNA at a frequency in a sample as low as 1.0% to 0.0001%. The panel can allow for detection of tumor markers in sequenced cfDNA at a frequency in a sample as low as 0.01% to 0.0001%.

A genetic variant can be exhibited in a percentage of a population of subjects who have a disease (e.g., cancer). In some cases, at least 1%, 2%, 3%, 5%, 10%, 20%, 30%, 40%, 50%, 60%, 70%, 80%, 90%, 95%, or 99% of a population having the cancer exhibit one or more genetic variants in at least one of the regions in the panel. For example, at least 80% of a population having the cancer may exhibit one or more genetic variants in at least one of the genomic positions in the panel.

The panel can comprise one or more locations comprising genomic regions of interest from each of one or more genes. In some cases, the panel can comprise one or more locations comprising genomic regions of interest from each of at least 1, 2, 3, 4, 5, 6, 7, 8, 9, 10, 15, 20, 25, 30, 40, 50, or 80 genes. In some cases, the panel can comprise one or more locations comprising genomic regions of interest from each of at most 1, 2, 3, 4, 5, 6, 7, 8, 9, 10, 15, 20, 25, 30, 40, 50, or 80 genes. In some cases, the panel can comprise one or more locations comprising genomic regions of interest from each of from about 1 to about 80, from 1 to about 50, from about 3 to about 40, from 5 to about 30, from 10 to about 20 different genes.

The locations comprising genomic regions in the panel can be selected so that one or more epigenetically modified regions are detected. The one or more epigenetically modified regions can be acetylated, methylated, ubiquitylated, phosphorylated, sumoylated, ribosylated, and/or citrullinated. For example, the regions in the panel can be selected so that one or more methylated regions are detected.

The regions in the panel can be selected so that they comprise sequences differentially transcribed across one or more tissues. In some cases, the locations comprising genomic regions can comprise sequences transcribed in certain tissues at a higher level compared to other tissues. For example, the locations comprising genomic regions can comprise sequences transcribed in certain tissues but not in other tissues.

The genomic locations in the panel can comprise coding and/or non-coding sequences. For example, the genomic locations in the panel can comprise one or more sequences in exons, introns, promoters, 3' untranslated regions, 5' untranslated regions, regulatory elements, transcription start sites, and/or splice sites. In some cases, the regions in the panel can comprise other non-coding sequences, including pseudogenes, repeat sequences, transposons, viral elements, and telomeres. In some cases, the genomic locations in the panel can comprise sequences in non-coding RNA, e.g., ribosomal RNA, transfer RNA, Piwi-interacting RNA, and microRNA.

The genomic locations in the panel can be selected to detect (diagnose) a cancer with a desired level of sensitivity (e.g., through the detection of one or more genetic variants). For example, the regions in the panel can be selected to detect the cancer (e.g., through the detection of one or more genetic variants) with a sensitivity of at least 50%, 55%, 60%, 65%, 70%, 75%, 80%, 85%, 90%, 95%, 96%, 97%, 98%, 99%, 99.5%, or 99.9%. The genomic locations in the panel can be selected to detect the cancer with a sensitivity of 100%.

The genomic locations in the panel can be selected to detect (diagnose) a cancer with a desired level of specificity (e.g., through the detection of one or more genetic variants). For example, the genomic locations in the panel can be selected to detect cancer (e.g., through the detection of one or more genetic variants) with a specificity of at least 50%, 55%, 60%, 65%, 70%, 75%, 80%, 85%, 90%, 95%, 96%, 97%, 98%, 99%, 99.5%, or 99.9%. The genomic locations in the panel can be selected to detect the one or more genetic variant with a specificity of 100%.

The genomic locations in the panel can be selected to detect (diagnose) a cancer with a desired positive predictive value. Positive predictive value can be increased by increasing sensitivity (e.g., chance of an actual positive being detected) and/or specificity (e.g., chance of not mistaking an actual negative for a positive). As a non-limiting example, genomic locations in the panel can be selected to detect the one or more genetic variant with a positive predictive value of at least 50%, 55%, 60%, 65%, 70%, 75%, 80%, 85%, 90%, 95%, 96%, 97%, 98%, 99%, 99.5%, or 99.9%. The regions in the panel can be selected to detect the one or more genetic variant with a positive predictive value of 100%.

The genomic locations in the panel can be selected to detect (diagnose) a cancer with a desired accuracy. As used herein, the term "accuracy" may refer to the ability of a test to discriminate between a disease condition (e.g., cancer) and healthy condition. Accuracy may be can be quantified using measures such as sensitivity and specificity, predictive values, likelihood ratios, the area under the ROC curve, Youden's index and/or diagnostic odds ratio.

Accuracy may presented as a percentage, which refers to a ratio between the number of tests giving a correct result and the total number of tests performed. The regions in the panel can be selected to detect cancer with an accuracy of at least 50%, 55%, 60%, 65%, 70%, 75%, 80%, 85%, 90%, 95%, 96%, 97%, 98%, 99%, 99.5%, or 99.9%. The genomic locations in the panel can be selected to detect cancer with an accuracy of 100%.

A panel may be selected to be highly sensitive and detect low frequency genetic variants. For instance, a panel may be selected such that a genetic variant or tumor marker present in a sample at a frequency as low as 0.01%, 0.05%, or 0.001% may be detected at a sensitivity of at least 50%, 55%, 60%, 65%, 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with a sensitivity of 70% or greater. A panel may be selected to detect a tumor marker at a frequency in a sample as low as 0.1% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.01% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.001% with a sensitivity of at least 50%, 55%, 60%, 65%, 70%, 75%, 80%, 85%, 90%, 95%, 96%, 97%, 98%, 99%, 99.5%, or 99.9%.

A panel may be selected to be highly specific and detect low frequency genetic variants. For instance, a panel may be selected such that a genetic variant or tumor marker present in a sample at a frequency as low as 0.01%, 0.05%, or 0.001% may be detected at a specificity of at least 50%, 55%, 60%, 65%, 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with a specificity of 70% or greater. A panel may be selected to detect a tumor marker at a frequency in a sample as low as 0.1% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with a specificity of at least 70%, 75%, 80%, 85%, 90%, 95%, 96%, 97%, 98%, 99%, 99.5%, or 99.9%.

A panel may be selected to be highly accurate and detect low frequency genetic variants. A panel may be selected such that a genetic variant or tumor marker present in a sample at a frequency as low as 0.01%, 0.05%, or 0.001% may be detected at an accuracy of at least 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with an accuracy of 70% or greater. A panel may be selected to detect a tumor marker at a frequency in a sample as low as 0.1% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with an accuracy of at least 70%, 75%, 80%, 85%, 90%, 95%, 96%, 97%, 98%, 99%, 99.5%, or 99.9%.

A panel may be selected to be highly predictive and detect low frequency genetic variants. A panel may be selected such that a genetic variant or tumor marker present in a sample at a frequency as low as 0.01%, 0.05%, or 0.001% may have a positive predictive value of at least 70%, 75%, 80%, 85%, 90%, 95%, 96%, 97%, 98%, 99%, 99.5%, or 99.9%.

The concentration of probes or baits used in the panel may be increased (2 to 6 ng/µL) to capture more nucleic acid molecule within a sample. The concentration of probes or baits used in the panel may be at least 2 ng/µL, 3 ng/µL, 4 ng/µL, 5 ng/µL, 6 ng/µL, or greater. The concentration of probes may be about 2 ng/µL to about 3 ng/µL, about 2 ng/µL to about 4 ng/µL, about 2 ng/µL to about 5 ng/µL, about 2 ng/µL to about 6 ng/µL. The concentration of probes or baits used in the panel may be 2 ng/µL or more to 6 ng/µL or less. In some instances this may allow for more molecules within a biological to be analyzed thereby enabling lower frequency alleles to be detected.

In an embodiment, after sequencing, sequence reads may be stored in the sequence read datastore 109. The sequence reads can be stored in any format. The sequence read datastore 109 may be local and/or remote to a location where sequencing is performed.

As shown in FIG. 2, the stored sequence reads may be subjected to a sequence analysis pipeline 112. The sequence analysis pipeline 112 may include a sequence quality control (QC) component 113 that may filter sequence reads from the laboratory system 102. The sequence quality control (QC) component 113 may assign a quality score to one or more sequence reads. A quality score may be a representation of sequence reads that indicates whether those sequence reads may be useful in subsequent analysis based on a threshold. In some cases, some sequence reads are not of sufficient quality or length to perform a subsequent mapping step. Sequence reads with a quality score at least 90%, 95%, 99%, 99.9%, 99.99% or 99.999% may be filtered out of a data set of sequence reads. In other cases, sequence reads assigned a quality scored at least 90%, 95%, 99%, 99.9%, 99.99% or 99.999% may be filtered out of the data set.

Sequence reads that meet a specified quality score threshold may be mapped to a reference genome by a copy number module 115. After mapping alignment, sequence reads may be assigned a mapping score. A mapping score may be a representation of sequence reads mapped back to the reference sequence indicating whether each position is or is not uniquely mappable. Sequence reads with a mapping score at least 90%, 95%, 99%, 99.9%, 99.99% or 99.999% may be filtered out of the data set. In other cases, sequencing reads assigned a mapping scored less than 90%, 95%, 99%, 99.9%, 99.99% or 99.999% may be filtered out of the data set. After filtering, the plurality of sequence reads generates a chromosomal region of coverage. The copy number module 115 may divide the chromosomal regions into variable length windows or bins. A window or bin may be at least 5 kb, 10, kb, 25 kb, 30 kb, 35, kb, 40 kb, 50 kb, 60 kb, 75 kb, 100 kb, 150 kb, 200 kb, 500 kb, or 1000 kb. A window or bin may also have bases up to 5 kb, 10, kb, 25 kb, 30 kb, 35, kb, 40 kb, 50 kb, 60 kb, 75 kb, 100 kb, 150 kb, 200 kb, 500 kb, or 1000 kb. A window or bin may also be about 5 kb, 10, kb, 25 kb, 30 kb, 35, kb, 40 kb, 50 kb, 60 kb, 75 kb, 100 kb, 150 kb, 200 kb, 500 kb, or 1000 kb.

The copy number module 115 may normalize coverage by causing the window or bin to contain about the same number of mappable bases. In some cases, each window or bin in a chromosomal region may contain the exact number of mappable bases. In other cases, each window or bin may contain a different number of mappable bases. Additionally, each window or bin may be non-overlapping with an adjacent window or bin. In other cases, a window or bin may overlap with another adjacent window or bin. In some cases a window or bin may overlap by at least 1 bp, 2, bp, 3 bp, 4 bp, 5, bp, 10 bp, 20 bp, 25 bp, 50 bp, 100 bp, 200 bp, 250 bp, 500 bp, or 1000 bp. In other cases, a window or bin may overlap by up to 1 bp, 2, bp, 3 bp, 4 bp, 5, bp, 10 bp, 20 bp, 25 bp, 50 bp, 100 bp, 200 bp, 250 bp, 500. bp, or 1000 bp. In some cases a window or bin may overlap by about 1 bp, 2, bp, 3 bp, 4 bp, 5, bp, 10 bp, 20 bp, 25 bp, 50 bp, 100 bp, 200 bp, 250 bp, 500 bp, or 1000 bp.

In some cases, each of the window regions may be sized so they contain about the same number of uniquely mappable bases. The mappability of each base that comprise a window region is determined and used to generate a mappability file which contains a representation of reads from the references that are mapped back to the reference for each file. The mappability file contains one row per every position, indicating whether each position is or is not uniquely mappable.

Additionally, predefined windows, known throughout the genome to be hard to sequence, or contain a substantially high GC bias, may be filtered from the data set. For example, regions known to fall near the centromere of chromosomes (i.e., centromeric DNA) are known to contain highly repetitive sequences that may produce false positive results. These regions may be filtered out. Other regions of the genome, such as regions that contain an unusually high concentration of other highly repetitive sequences such as microsatellite DNA, may be filtered from the data set.

The number of windows analyzed may also vary. In some cases, at least 10, 20, 30, 40, 50, 100, 200, 500, 1000, 2000, 5,000, 10,000, 20,000, 50,000 or 100,000 windows are analyzed. In other cases, the number of widows analyzed is up to 10, 20, 30, 40, 50, 100, 200, 500, 1000, 2000, 5,000, 10,000, 20,000, 50,000 or 100,000 windows are analyzed.

The copy number module 115 may determine the read coverage for each window/bin region. This may be performed using either reads with barcodes, or without barcodes. In cases without barcodes, the previous mapping steps will provide coverage of different base positions. Sequence reads that have sufficient mapping and quality scores and fall within chromosome windows that are not filtered, may be counted. The number of coverage reads may be assigned a score per each mappable position.

In an embodiment, a quantitative measure related to sequencing read coverage is a measure indicative of the number of reads derived from a DNA molecule corresponding to a genetic locus (e.g., a particular position, base, region, gene or chromosome from a reference genome). In order to associate reads to a genetic locus, the reads can be mapped or aligned to the reference. Software to perform mapping or aligning (e.g., Bowtie, BWA, mrsFAST, BLAST, BLAT) can associate a sequencing read with a genetic locus. During the mapping process, particular parameters can be optimized. Non-limiting examples of optimization of the mapping processing can include masking repetitive regions; employing mapping quality (e.g., MAPQ) score cut-offs; using different seed lengths to generate alignments; and limiting the edit distance between positions of the genome.

Quantitative measures associated with sequencing read coverage can include counts of reads associated with a genetic locus. In some cases, the counts are transformed into new metrics to mitigate the effects of differing sequencing depth, library complexity, or size of the genetic locus. Exemplary metrics are Read Per Kilobase per Million (RPKM), Fragments Per Kilobase per Million (FPKM), Trimmed Mean of M values (TMM), variance stabilized raw counts, and log transformed raw counts. Other transformations are also known to those of skill in the art that may be used for particular applications.

Quantitative measures can be determined using numbers of read families or collapsed reads, wherein each read family or collapsed read corresponds to an initial template DNA molecule. Methods to collapse and quantify read families are found in PCT/US2013/058061 and PCT/US2014/000048, each of which is herein incorporated by reference in its entirety. In particular, quantifying read families and/or collapsing methods can be employed that use barcodes and sequence information from the sequencing read to sort reads into families, such that each family shares barcode sequences and at least a portion of the sequencing read sequence and/or the same genomic coordinates when mapped to a reference sequence. Each family is then, for the majority of the families, derived from a single initial template DNA molecule. Counts derived from mapping sequences from families can be referred to as "unique molecular counts" (UMCs). In some cases, determining a quantitative measure related to sequencing read coverage comprises normalizing UMCs by a metric related to library size to provide normalized UMCs ("normalized UMCs"). Exemplary methods are dividing the UMC of a genetic locus by the sum of all UMCs; dividing the UMC of a genetic locus by the sum of all autosomal UMCs. When comparing multiple sequencing read data sets, UMCs can, for example, be normalized by the median UMCs of the genetic loci of the two sequencing read data sets. In some cases, the quantitative measure related to sequencing read coverage can be normalized UMCs that are further normalized as follows: (i) normalized UMCs are determined for corresponding genetic loci from sequencing reads derived from training samples; (ii) for each genetic locus, normalized UMCs of the sample are normalized by the median of the normalized UMCs of the training samples at the corresponding loci, thereby providing Relative Abundances (RAs) of genetic loci.

Consensus sequences can identified based on their sequences, for example by collapsing sequencing reads based on identical sequences within the first 5, 10, 15, 20, or 25 bases. In some cases, collapsing allows for 1 difference, 2 differences, 3 differences, 4 differences, or 5 differences in the reads that are otherwise identical. In some cases, collapsing uses the mapping position of the read, for example the mapping position of the initial base of the sequencing read. In some cases, collapsing uses barcodes, and sequencing reads that share barcode sequences are collapsed into a consensus sequence. In some cases, collapsing uses both barcodes and the sequence of the initial template molecules. For example, all reads that share a barcode and map to the same position in the reference genome can be collapsed. In another example, all reads that share a barcode and a sequence of the initial template molecule (or a percentage identity to a sequence of the initial template molecule) can be collapsed.

In some cases, quantitative measures of sequencing read coverage are determined for specific sub-regions of a genome. Regions can be bins, genes of interest, exons, regions corresponding to sequence probes, regions corresponding to primer amplification products, or regions corresponding to primer binding sites. In some cases, sub-regions of the genome are regions corresponding to sequence capture probes. A read can map to a region corresponding to the sequence capture probe if at least a portion of the read maps at least a portion of the region corresponding to the sequence capture probe. A read can map to a region corresponding to the sequence capture probe if at least a portion of the read maps to the majority of the region corresponding to the sequence capture probe. A read can map to a region corresponding to the sequence capture probe if at least a portion of the read maps across the center point of the region corresponding to the sequence capture probe.

In another embodiment involving barcodes, all sequences with the same barcode, physical properties or combination of the two may be collapsed into one read, as they are all derived from the sample parent molecule to reduce biases which may have been introduced during amplification. For example, if one molecule is amplified 10 times but another is amplified 1000 times, each molecule is only represented once after collapse thereby negating the effect of uneven amplification. Only reads with unique barcodes may be counted for each mappable position and influence the assigned score.

Consensus sequences can be generated from families of sequence reads by any method known in the art. Such methods include, for example, linear or non-linear methods of building consensus sequences (such as voting, averaging, statistical, maximum a posteriori or maximum likelihood detection, dynamic programming, Bayesian, hidden Markov or support vector machine methods, etc.) derived from digital communication theory, information theory, or bioinformatics.

After the sequence read coverage has been determined, a stochastic modeling algorithm may be applied to convert the normalized nucleic acid sequence read coverage for each window/bin region to the discrete copy number states. In some cases, this algorithm may comprise one or more of the following: Hidden Markov Model, dynamic programming, support vector machine, Bayesian network, trellis decoding, Viterbi decoding, expectation maximization, Kalman filtering methodologies and neural networks. The discrete copy number states of each window region can be utilized to identify copy number variation in the chromosomal regions. In some cases, all adjacent window/bin regions with the same copy number can be merged into a segment to report the presence or absence of copy number variation state. In some cases, various windows/bins can be filtered before they are merged with other segments.

Data analyzed and/or output by the sequence analysis pipeline 112 may be stored in an analysis datastore 117.

The variant detection pipeline 130 may retrieve/receive data from the analysis datastore 117. For example, the variant detection pipeline 130 may retrieve/receive data representing a plurality of sequence reads. The plurality of sequence reads may be analyzed to determine one or more variants by the copy number module 115 and/or the HRD module 300. Variants may include, for example, single nucleotide variants (SNVs), indels, fusions, and copy number variation. Any known technique for variant calling may be used. In an embodiment, nucleotide variations in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, the length of a given cfDNA fragment based upon where its endpoints (i.e., it 5' and 3' terminal nucleotides) map to the reference sequence, the offset of a midpoint of a given cfDNA fragment from a midpoint of a genomic region in the cfDNA fragment, and optionally which if any, include a reference nucleotide (i.e., same as in the reference sequence). If the number of sequenced nucleic acids in the subset including a nucleotide variant exceeding a selected threshold, then a variant nucleotide can be called at the designated position. The threshold can be a simple number, such as at least 1, 2, 3, 4, 5, 6, 7, 9, or 10 sequenced nucleic acids within the subset including the nucleotide variant or it can be a ratio, such as a least 0.5, 1, 2, 3, 4, 5, 10, 15, or 20 of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

Generally speaking, the processor 120 may implement (be programmed by) various components of the variant detection pipeline 130, such as the copy number module 115, the HRD module 300, and/or other components. Alternatively, it should be noted that these components of the variant detection pipeline 130 may include a hardware module. Although illustrated separately for convenience, one or more of the various components or instructions, such as the copy number module 115 and the HRD module 300 may be integrated with one another. In any event, the variant detection pipeline 130 may cause the computer system 110 to identify variants, diseases from the variants (precision diagnostics), HRD, and/or treatment regimens. The precision diagnostic and treatment regimen may be stored in a repository such as clinical result store 160 or diagnostic result store 150.

The HRD module 300 may be configured to analyze output from the sequence analysis pipeline 112. The HRD module 300 may be configured to produce one or more of: de novo fusion rearrangement calls, deletion calls, SNV/ Indel pathogenic annotation, and/or an HRD score. The HRD module 300 may comprise an HRD aggregator configured to generate a summary of sample level HRD status.

Figure 3:
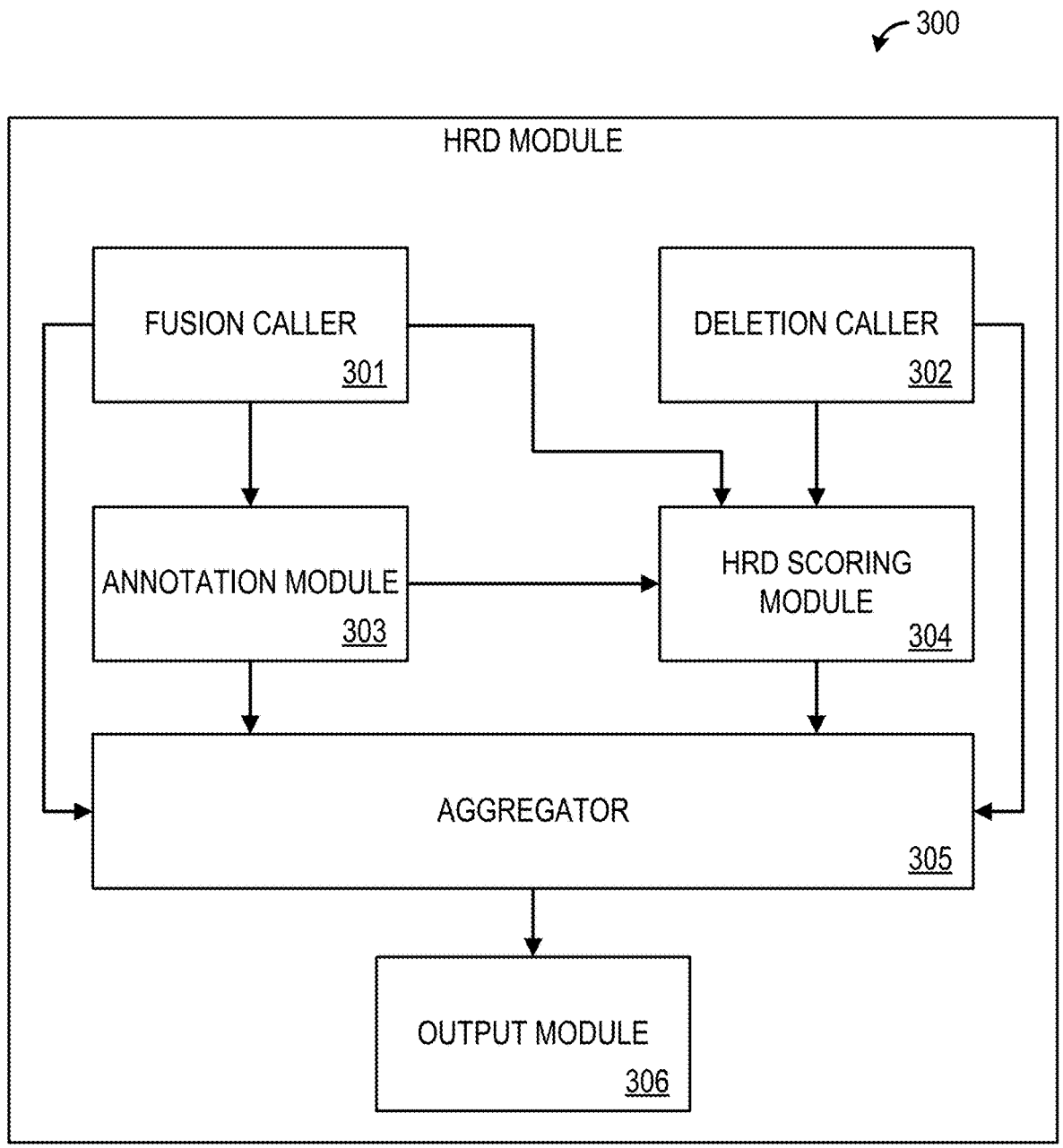
FIG. 3 illustrates a schematic diagram of a HRD scoring module according to an embodiment of the present disclosure.

As shown in FIG. 3, the HRD module 300 may be configured to execute one or more of, a fusion caller 301, a deletion caller 302, an annotation module 303, an HRD scoring module 304, an aggregator 305, and/or an output module 306.

The fusion caller 301 may be configured to generate one or more candidate fusion calls by analyzing data received from the sequence analysis pipeline 112. The fusion caller 301 may be configured to assemble candidate fusion reads in de Bruijn graphs, call candidate fusion events, filter the candidate fusion calls, and remove technical false positives. The fusion caller 301 may be configured to select fusion candidate reads, cluster the fusion candidate reads into packets, and assemble the clustered fusion candidate reads into de Bruijn graph assemblies. The fusion caller 301 may be configured to flatten the de Bruijn graph assemblies into fusion candidate contigs, align the fusion candidate contigs to a reference with decoy, and generate candidate fusion calls.

In an embodiment, the fusion caller 301 may be configured to select candidate fusion reads, build an undirected graph G of reads by joining reads with consistent breakpoints, and save the output as a packets info file. The fusion caller 301 may be configured to hybridize the reads and assemble them into a de Bruijn graph assembly. The fusion caller 301 may be configured to flatten the assemblies into linear contigs. The fusion caller 301 be configured to align contigs on a reference with decoy and call putative fusions.

The fusion caller 301 may be configured to filter the candidate fusion calls based on one or more criteria. The one or more criteria may comprise filtering a candidate fusion, if none of its breakpoints is 350 bases or less away from one of the probes in the probes set. The one or more criteria may comprise filtering a candidate fusion, if none of its breakpoints belongs to one of the genes in the gene list. The one or more criteria may comprise filtering a candidate fusion, if it consists of two deletions (96 bases or less), which are 48 bases or less away from each other. The one or more criteria may comprise filtering a candidate fusion, if it is a deletion of strictly less than 60 bases. The one or more criteria may comprise filtering a candidate fusion, if it does not have at least one double stranded molecule support, and its average family size is <1/0.9 (~1.10). Average family size may be defined as the number of supporting reads divided by the number of supporting molecules. The one or more criteria may comprise filtering a candidate fusion, if the alignment between the 120 bases segment of reference centered at the first breakpoint, and the 120 bases segment of reference centered at the second breakpoint has an alignment score of 50 or more. The one or more criteria may comprise filtering a candidate fusion if the alignment of the segment of length 36 away from the first breakpoint, against the segment of length 36 away from the second breakpoint, has an alignment score of 20 or more. The one or more criteria may comprise filtering a candidate fusion if it does not have robust support. A molecule may be considered robust if the molecule has a family size of 2 or more (wherein family size refers to the number of reads supporting that molecule).

If a candidate fusion is reciprocal to one, and only one, other candidate fusion, and if the other candidate fusion has not been filtered out by any other criteria, the fusion caller 301 may be configured to upgrade the candidate fusion to passing. The fusion caller 301 may be configured to tag a candidate fusion if one or more of the candidate fusions breakpoints lie in an amplified region.

The fusion caller 301 may be configured to output fusion data comprising the filtered fusion calls. The fusion data may comprise ancillary data for in depth analysis of fusion events. Data output by the fusion caller 301 may be read by the annotation module 303 and/or the aggregator 305.

Figure 4:
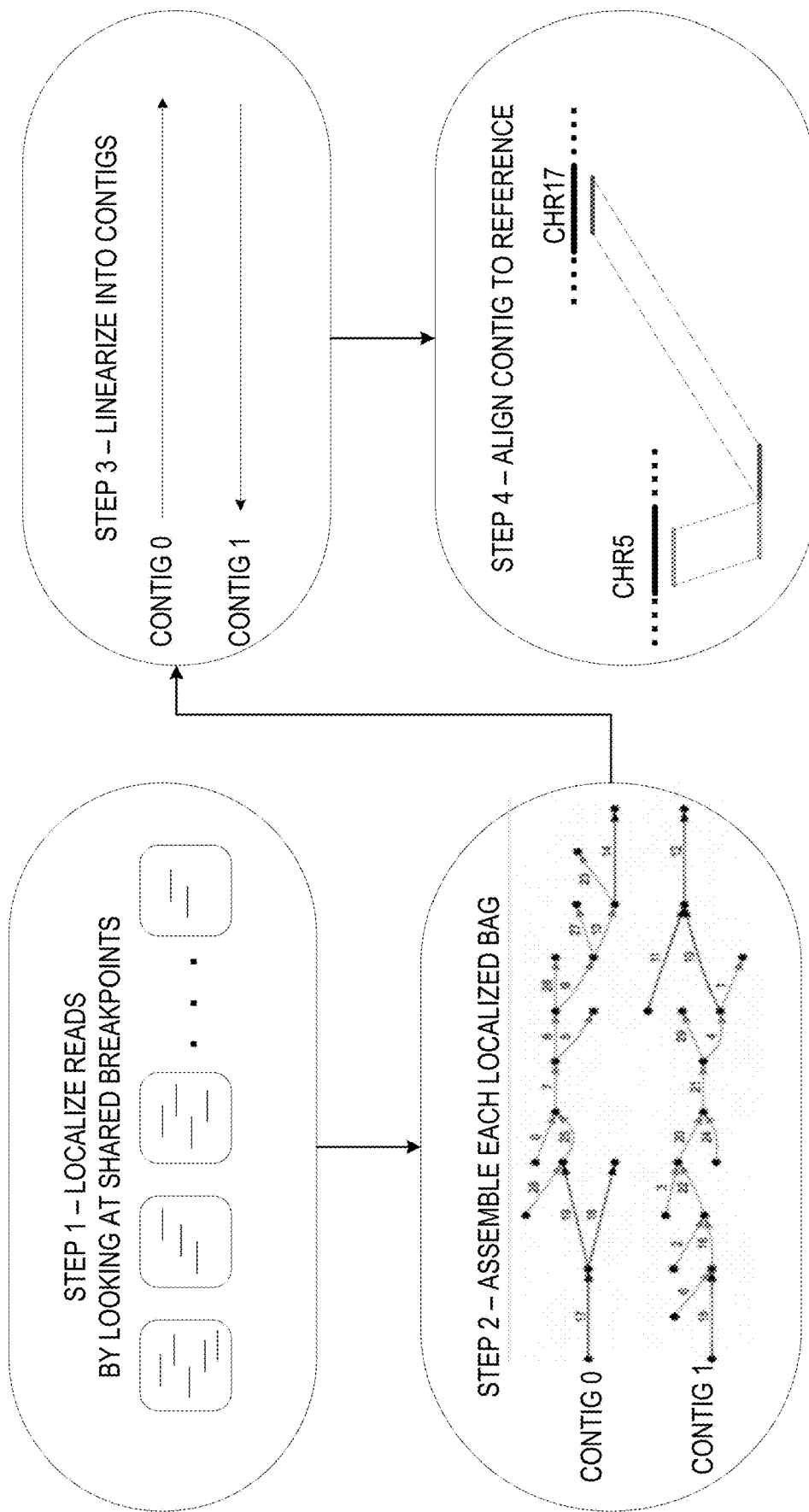
FIG. 4 illustrates a schematic diagram of a fusion caller according to an embodiment of the present disclosure.

FIG. 4 illustrates a schematic diagram of a de novo fusion caller (e.g., the fusion (rearrangement) caller 301 referenced in FIG. 3) according to an embodiment of the present disclosure. In the embodiment shown, the fusion caller localizes reads by looking at shared breakpoints (step 1), assembling localized bags (step 2), linearizing the localized bags into contigs (step 3), and aligning the contigs to a reference sequence (step 4) to determine whether a given sample includes an HRD nucleic acid variant. In some embodiments, de novo fusion callers include instructions configured for aligning a plurality of sequence reads to a reference sequence, determining breakpoints in an alignment of at least one sequence read of the plurality of sequence reads to the reference sequence, identifying any sequence reads associated with the breakpoints in the alignment as candidate fusion sequence reads, and determining candidate fusion sequence reads associated with common breakpoints of one or more breakpoints. These embodiments also typically include grouping the candidate fusion sequence reads based on one or more common breakpoints. In an embodiment, the reads may be grouped (e.g., clustered) based on having breakpoints within a threshold window of nucleotides. The instructions may be further configured for assembling the candidate fusion sequence reads in the groups into one or more contigs, aligning the contigs from the groups to the reference sequence, determining, based on the alignments of the contigs from the groups, one or more candidate fusion events, applying one or more criteria to the one or more candidate fusion events, and determining, based on applying the one or more criteria to the one or more candidate fusion events, one or more fusion events that comprise the second LoF HRD nucleic acid variant. In certain embodiments, the criteria includes filtering criteria, such as the absence of a breakpoint near a probe, the absence of a breakpoint in a reportable gene, the rejection of small indels and intronic events, the running of a "pc_molecules" test (pc_molecules=n_molecules/n_reads) and discarding fusions with an average family size that is less than 1.7 in some embodiments, the addressing stitch-related known artifacts, the rejection of events if they could be a "template switch," the application of a minimum robust molecules test, and/or the like. Additional details regarding de novo fusion callers that are optionally adapted for use in performing the methods and related aspects of the present disclosure are described in, for example, U.S. patent application Ser. No. 16/803,680, filed Feb. 27, 2020, which is incorporated by reference in its entirety.

Returning to FIG. 3, the deletion caller 302 may be configured to determine homozygous deletions and loss-of-heterozygosity (LOH) on a gene and genome-wide level by analyzing data (e.g., copy number data) received from the sequence analysis pipeline 112. The deletion caller 302 may be configured to detect a deletion by comparing coverage of the region of interest against a reference profile generated from cancer samples that have no deletions.

Figure 5:
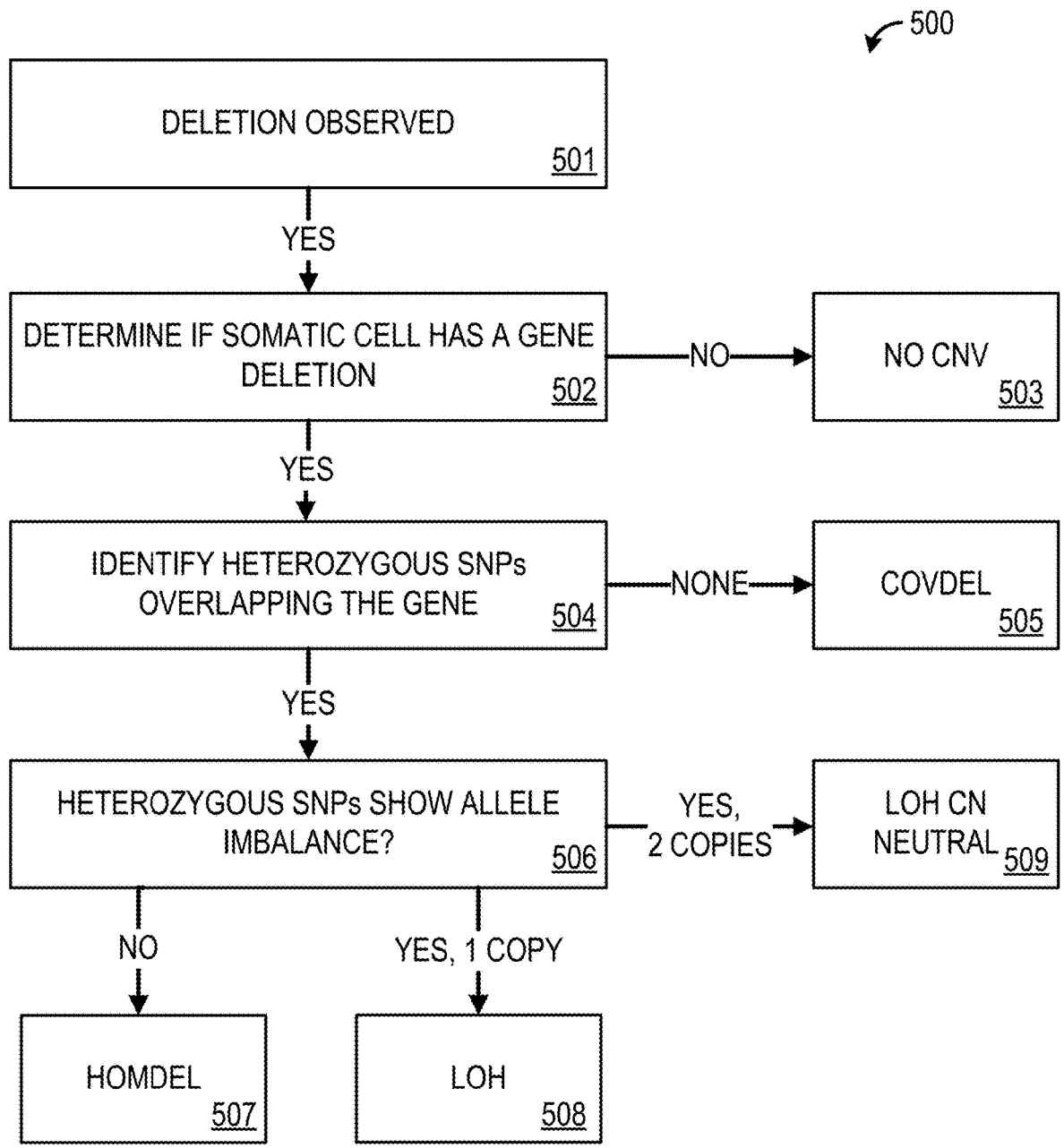
FIG. 5 illustrates a schematic diagram of a deletion caller according to an embodiment of the present disclosure.

In an embodiment of a system 500, shown in FIG. 5, the deletion caller 302 may generate a deletion call by determining if a deletion is observed based on comparing coverage of the region of interest against a reference profile generated from cancer samples that have no deletions at 501. If a deletion is observed at 501, gene coverage and z-scores adjusted by a baseline MAF may be analyzed to determine if somatic cells have a gene deletion at 502. If no deletion is reported at 502, the resulting call may be no deletion or amplification, "no cnv" at 503. If a deletion is reported at 502, heterozygous SNPs overlapping the gene may be identified at 504. If no heterozygous SNP overlapping the gene is observed at 504, the gene may be called as no heterozygous SNPs to make the differentation even though there is deletion, "cov_del" at 505. If a heterozygous SNP overlapping the gene is observed at 504, heterozygous SNPs showing allele imbalance may be determined at 506. If at 506, no heterozygous SNPs showing allele imbalance are determined, the gene may be called as a homozygous deletion, "homdel" at 507. If at 506, heterozygous SNPs showing allele imbalance are determined with 1 copy, the gene may be called as a Loss of Heterozygosity, "LOH" at 508. If at 506, heterozygous SNPs showing allele imbalance are determined with 2 copies, the gene may be called as a copy number neutral Loss of Heterozygosity, "LOH CN NEUTRAL" at 509.

Once a deletion is detected, the deletion caller 302 may be configured to label the deletion. For example, the deletion caller 302 may be configured to label the deletion as "cov_del," "loh," "loh_cn_neutral," or "homdel." The deletion caller 302 may utilize mutant allele fractions (MAFs) of a predefined list of germline SNPs to determine if cancer cells have a single copy of the region of interest (label as "LOH") or if both copies are deleted (label as "homdel"). The discriminator of the two cases resides in the observation that a single copy in tumor cells produces an allelic imbalance of the heterozygous SNPs MAFs. The decision rule may be based on a likelihood ratio test, where the likelihood ratio of the two models representing the two types of deletions is compared to a threshold estimated from a training set of "target not detected" (TND) samples. The likelihood models may be based on trained MAF distributions of heterozygous SNPs for all 3 possible SNP genotypes. For deletion cases when no heterozygous SNPs are observed, the output label used may be "cov_del" and represents the third label representing predicted deletions.

In an embodiment, shown in FIG. 5, the deletion caller 302 may generate a deletion call by determining if a deletion is observed based on comparing coverage of the region of interest against a reference profile generated from cancer samples that have no deletions at 501. If a deletion is observed at 501, gene coverage and z-scores adjusted by a baseline MAF may be analyzed to determine if somatic cells have a gene deletion at 502. If no deletion is reported at 502, the resulting call may be no deletion or amplification, "no cnv" at 503. If a deletion is reported at 502, heterozygous SNPs overlapping the gene may be identified at 504. If no heterozygous SNP overlapping the gene is observed at 504, the gene may be called as no heterozygous SNPs to make the differentation even though there is deletion, "cov_del" at 505. If a heterozygous SNP overlapping the gene is observed at 504, heterozygous SNPs showing allele imbalance may be determined at 506. If at 506, no heterozygous SNPs showing allele imbalance are determined, the gene may be called as a homozygous deletion, "homdel" at 507. If at 506, heterozygous SNPs showing allele imbalance are determined with 1 copy, the gene may be called as a Loss of Heterozygosity, "LOH" at 508. If at 506, heterozygous SNPs showing allele imbalance are determined with 2 copies, the gene may be called as a copy number neutral Loss of Heterozygosity, "LOH CN NEUTRAL" at 509.

The deletion caller 302 may be configured to determine reportable genes and/or valid genes. Valid genes may be included in a final deletion call output table. A valid gene may be a gene that meets the following criteria: number of good probes is >30 and 95% limit of detection (LoD) for LOH is <0.3 (exception to meeting this threshold possible for biologically important genes). A reportable LOH or homozygous deletion gene may be a gene that are associated with a probability of detecting a heterozygous SNP>50%. If the probability of detecting a heterozygous SNP is less than or equal to 50%, the gene may be reported as a coverage-based deletion ("cov_del").

In certain embodiments, homozygous deletion/LOH fusion (CNV) callers (e.g., the deletion caller 302) detect gene-level LOH, detect homozygous deletions, and/or estimate genome-wide level of LOH in a given sample. In some of these implementations, the homozygous deletion/LOH fusion (CNV) callers typically achieve about a 5% limit of detection (LOD) and greater than 99% specificity for detecting deletion of HRR genes. In some embodiments, CNV callers are molecule coverage-based and use SNP information to distinguish between LOH (allelic imbalance) and homozygous deletions (50% MAF for SNPs). In certain embodiments, CNV callers are fragment size information-based. These implementations involve the use of fragment size distributions, which can improve the sensitivity/specificity of detecting genes or genomic regions, and related deletions.

To further illustrate, in some embodiments, CNV callers involve the use of a first probability that the sequence information under consideration includes a first state and a second probability that the sequence information includes a second state in which the first or second state includes a LoF HRD nucleic acid variant. Typically, these embodiments include generating the first probability that the sequence information includes the first state, generating the second probability that the sequence information includes the second state, comparing the first probability and the second probability, and generating a prediction of whether the sequence information includes the first state or the second state based on the comparing step. In some of these embodiments, CNV callers include generating via a first probabilistic distribution, a first model of allelic counts based on one or more germline single nucleotide polymorphism (SNP) positions associated with at least one genetic locus in the sequence information. The first model typically represents at least one somatic homozygous deletion. These embodiments also include generating via a second probabilistic distribution, a second model of allelic counts based on the one or more germline SNP positions associated with the genetic locus in the sequence information. The second model generally represents at least one somatic heterozygous deletion. These implementations also include comparing a first output of the first model and a second output of the second model, and generating a prediction that the somatic homozygous deletion for the genetic locus exists in the sequence information based on the comparison. In certain embodiments, CNV callers generate a first probability that the sequence information under consideration includes a somatic homozygous deletion and a second probability that the sequence information includes a somatic heterozygous deletion, compare the first probability and the second probability, and generate a prediction of whether the sequence information includes the somatic homozygous deletion or the somatic heterozygous deletion based on the comparison. Additional details regarding CNV callers that are optionally adapted for use in performing the methods and related aspects of the present disclosure are described in, for example, U.S. Non-Provisional patent application Ser. No. 16/803,680, filed Feb. 27, 2020, which is incorporated by reference in its entirety.

The deletion caller 302 may be configured to output deletion call data. The deletion call data may indicate, for example, a label (e.g., no_cnv, cov_del, loh, loh_cn_neutral, homdel, no call, and the like). The deletion call data may indicate, for example, genes with a loh/homdel reported, and when the prediction is based on a single heterozygous SNP. The deletion call data may indicate, for example, when multiple genes on different chromosomes have are labeled as "homdel" (e.g., potential baseline MAF error, not limited to reportable genes). The deletion call data may indicate, for example, genes with a somatic SNV/indel and are labeled as "homdel" (e.g. potential label error). The deletion call data may comprise all CNV calls (amplification, focal, deletion, aneuploidy etc) for all genes on panel. The deletion call data may comprise all genes on panel with one of the following conditions: Homozygous Deletion, LOH, coverage-based deletion, copy number neutral LOH or no call. The deletion call data may comprise all reportable genes with one of the following conditions: Homozygous Deletion, LOH, coverage-based deletion, copy number neutral LOH or no call. The deletion caller 302 may be configured to determine and output one or more plots for the summarizing gene-level LOH or deletions, including the coverage and the SNPs. The plots may comprise genome-wide (all regions concatenated) and chromosome level CNV plots, with probes highlighted by HRR genes and whether the HRR genes are called a coy del, homdel, loh deletion. The deletion call data may comprise a percent of segments that have LOH or deletion. The deletion call data may comprise segments used for deletion calling. Data output by the deletion caller 302 may be read by the HRD scoring module 304 and/or the aggregator 305.

Returning to FIG. 3, the annotation module 303 may be configured to provide data indicative of clinical significance, such as the relationships among variants and phenotypes (e.g., ClinVar data). The annotation module 303 may be configured to provide functional impact annotations for some or all SNV/Indels. The annotation module 303 may be configured to indicate a somatic call (e.g., somatic or germline) and/or a functional impact (e.g., considered deleterious by GH or a reversion) for called fusions.

Figure 6:
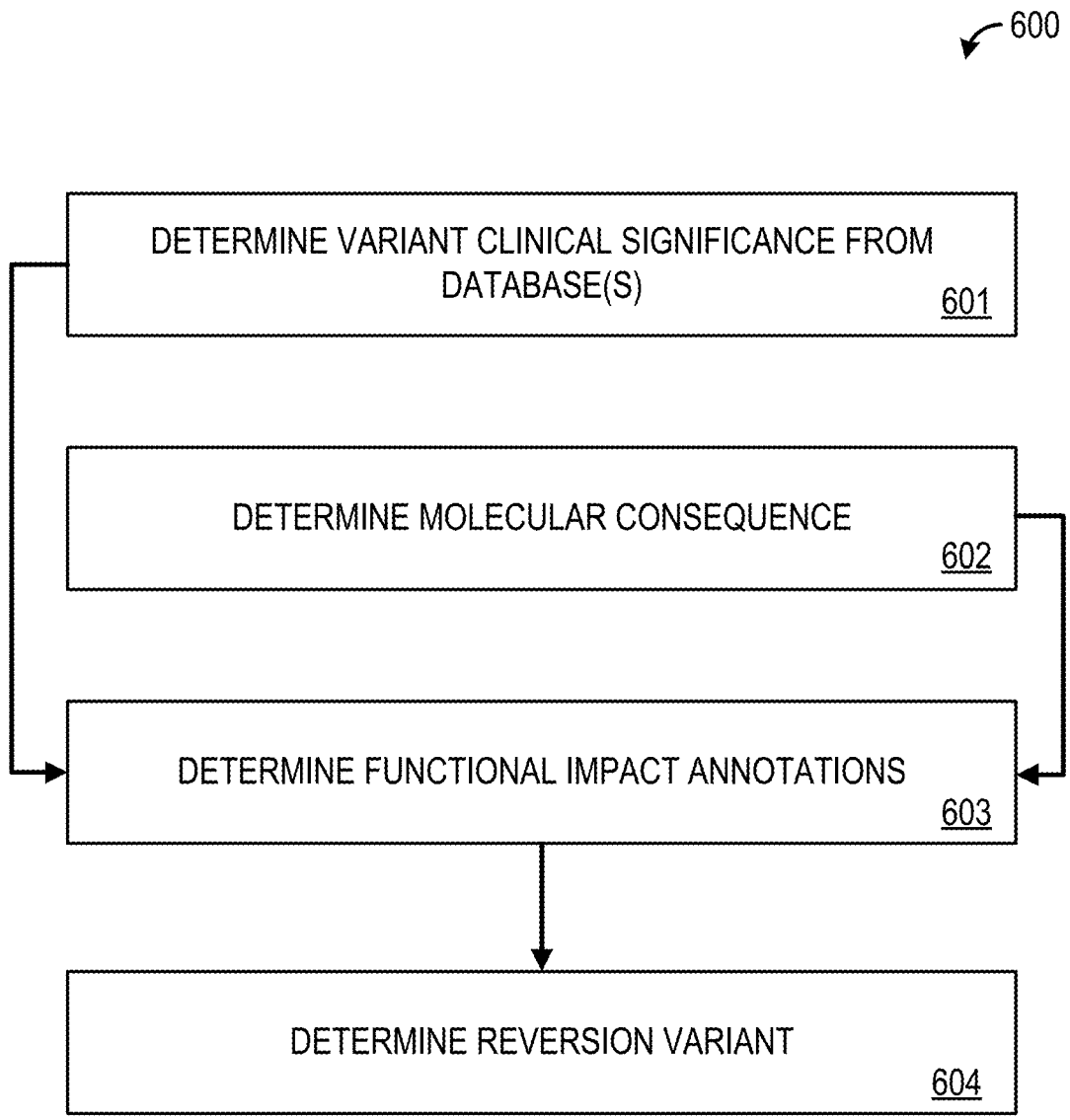
FIG. 6 illustrates a schematic diagram of an annotation module according to an embodiment of the present disclosure.

The annotation module 303 may analyze data received from the sequence analysis pipeline 112 and/or fusion data received from the fusion caller 301. The annotation module 303 may execute an annotation method 600, shown in FIG. 6.

The annotation module 303 may determine data indicative of clinical significance at 601. The annotation module 303 may determine data indicative of clinical significance by retrieving data associated with variants in a sample from a data source. For example, the data indicative of clinical significance may be ClinVar data retrieved from a remote or local data source. For example, data from a "CLNSIG" field for that variant in a ClinVar VCF file may be determined by matching on chromosome ("chrom"), position ("pos"), mutant nucleotides ("mut_nt"), and gene name ("gene"). The data indicative of clinical significance may be associated with the variant. The data indicative of clinical significance may be, for example, Benign, Likely benign, Uncertain significance, Likely pathogenic, Pathogenic, drug response, association, risk factor, protective, affects, conflicting data from submitters, other, and/or not provided. The data indicative of clinical significance may relate to review status indicative of the veracity of the data and may be, for example, no assertion, no assertion criteria provided, no assertion for the individual variant, criteria provided (single submitter), criteria provided (conflicting interpretations), criteria provided (multiple submitters, no conflicts), reviewed by expert panel, and/or practice guideline.

The annotation module 303 may be configured to determine a molecular consequence for some or all SNV/Indels at 602. Some or all variants in a sample may be assigned a molecular consequence based on application of a set of rules. If no rules apply, the molecular consequence may be "NULL". These rules may be applied by order of precedence, i.e., start from the top, and if one rule applies then the remaining rules may be ignored. The molecular consequence may be, for example, nonsense, frameshift, stop lost, start lost, inframe insertion, inframe deletion, inframe duplication, missense, splice acceptor, splice donor, synonymous, non coding, utr, promoter, splice region, splice event, and the like.

The annotation module 303 may be configured to determine functional impact annotations for some or all SNV/Indels at 603. Variants (SNV/Indel) in a sample may be annotated as "deleterious" or "NULL". By way of example, SNVs/Indels in any gene associated with data indicative of clinical significance that indicates that the mutation may be causative or strongly associated with disease (e.g., "Pathogenic" or "Likely pathogenic") and/or with response to therapy (e.g., "drug response"). SNVs/Indels in known HRR genes or in known tumor suppressor genes that are any of the following: nonsense, frameshift, splice acceptor, splice donor and are not common (e.g., <0.001 population allele frequency) and are not in BRCA2 with codon number larger than 3326—may be annotated as deleterious. Any remaining variants may be annotated as "NULL".

The annotation module 303 may be configured to determine reversion variants (e.g., small variants) at 604. Reversion variants may restore the function of a gene disrupted by a pathogenic allele. Generally, a reversion variant is determined if any of the following criteria are met:

SNVs that are in the same codon as a deleterious SNV and revert the codon to be non-deleterious In-frame indels that span the entire position of a deleterious SNV/Indel Indels that are within distance threshold with a frameshift indel and bring the protein back into frame Indels that are farther away from a frameshift indel and bring the protein back into frame if they are confirmed cis or deleterious trans Long deletions that are somatic and span another deleterious SNV or Indel in the same gene.

Figure 7:
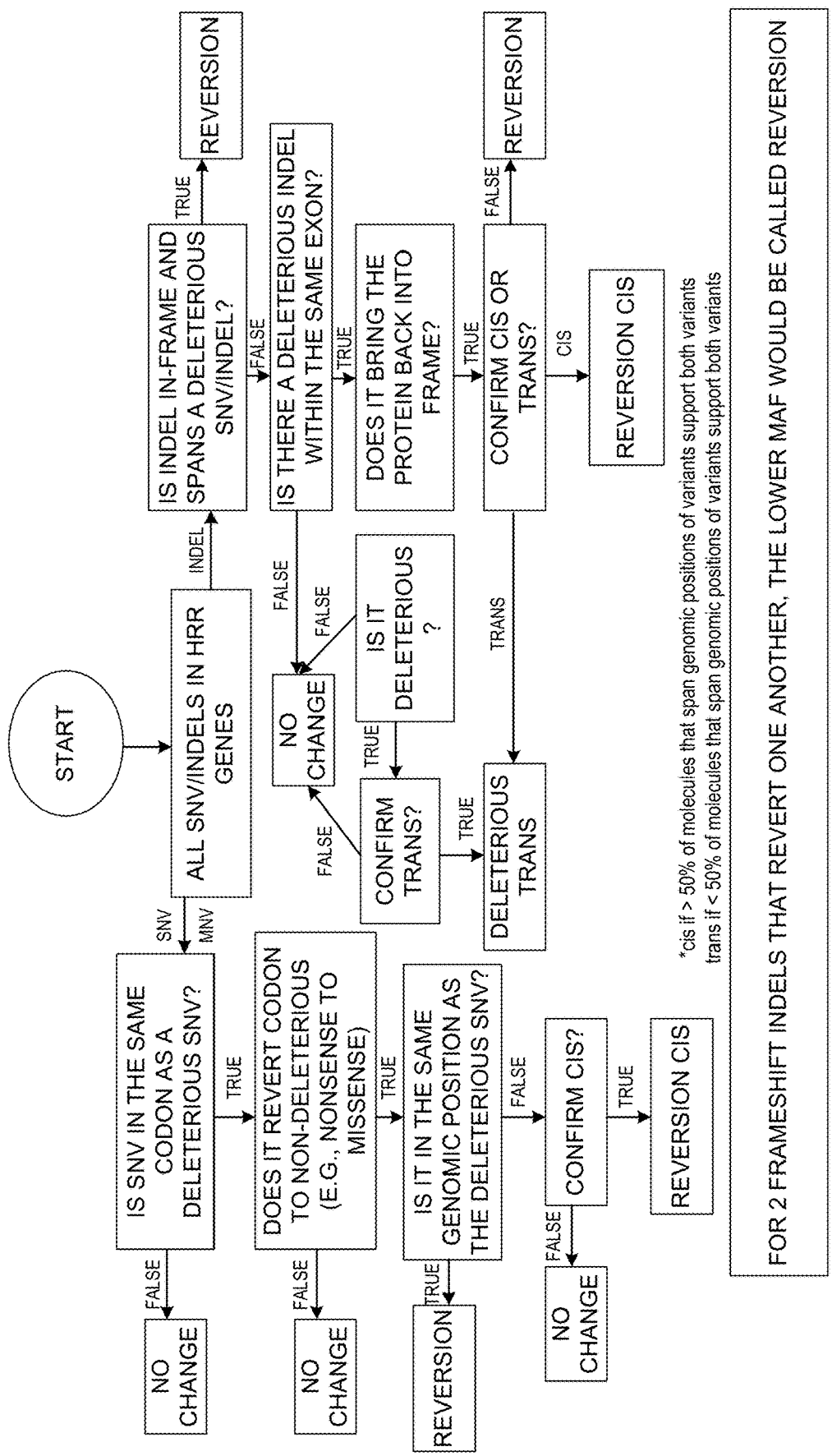
FIG. 7 illustrates a schematic diagram of a method for determining a reversion according to an embodiment of the present disclosure.

FIG. 7 shows an example method 700 for determining a reversion variant. For SNV and small indels that are classified as germline but meet the requirements of a reversion according to the method 700, the variant may be flagged for manual review.

Indels that are upstream or downstream from another frameshift indel and bring the protein back into frame (inserted or deleted nucleotides sum to a multiple of 3) are called "reversion_cis" if the indel can be confirmed in cis (sharing the same molecule) with the second frameshift indel. If the variants are confirmed to be in trans (on different molecules), the annotation is called "deleterious_trans". If the supporting molecules do not span both indels to determine cis/trans annotation and the protein is brought back into frame the annotation is simply "reversion".

SNVs that are in the same codon as a deleterious SNV (e.g., nonsense, pathogenic missense), and revert the codon to be non-deleterious (e.g., nonsense to missense, pathogenic missense to synonymous) may be labeled as reversions. A determination of whether the SNV is in the same genomic position as the deleterious SNV may be made and, if the SNV is in the same genomic position as the deleterious SNV and is of a non-deleterious consequence (e.g. "synonymous"), the SNV may be labeled as a reversion.

Indels that are in frame and span another deleterious SNV or Indel may be labeled as a reversion.

The annotation module 303 may also be configured to determine reversion variants (e.g., long deletions variants) at 604. Fusions and long deletions from the fusion data received from the fusion caller 301 may be used to annotate somatic call and functional impact. Long deletions may be defined as large genomic rearrangements resulting in the loss of DNA sequence within the same gene. Somatic classification for long deletions may be performed by the annotation module 303. Fusions and long deletions may be annotated as somatic if the variant percentage is below a configurable threshold (e.g. <15%), and as germline if the variant percentage is above a configurable threshold. Long deletions that meet the requirements of a reversion may have a somatic call of "somatic" regardless of the variant percentage. Long deletions may have a functional impact of "reversion" if the long deletion is somatic and spans another deleterious SNV or Indel in the same gene.

Long deletions with a variant percentage above a configurable threshold (e.g. >=15%) that meet the requirements of a reversion may have a functional impact of "reversion" and a somatic call of "somatic." This somatic status overwrites the original germline call determined by the configurable threshold. In an embodiment, all long deletions may have a "deleterious" functional impact annotation unless the long deletion is considered a reversion. In an embodiment, all fusions occurring between at least two different genes may have a "deleterious" functional impact annotation.

The annotation module 303 may be configured to output annotation data. The annotation data may comprise, for example, a fusion table indicating somatic call and functional impact. The annotation data may comprise, for example, SNV call data comprising some or all SNV results and/or some or all Indel results from the copy number module 115 with clinical significance data, deleterious annotations, and/or reversion annotations. The annotation data may comprise, for example, data associated with SNV/Indel calls with clinical significance annotation, molecular consequence, and/or functional impact. Data output by the annotation module 303 may be read by the HRD scoring module 304 and/or the aggregator 305.

Returning to FIG. 3, the HRD scoring module 304 may be configured to analyze and/or summarize data from the fusion caller 301, the deletion caller 302 and/or the annotation module 303 to generate an HRD score (e.g., a metric of measure of HRD). The HRD scoring module 304 may be configured to analyze data from some or all somatic variant outputs from the sequence analysis pipeline 112 and/or the variant detection pipeline 130 to calculate a max somatic allele fraction (msaf).

The HRD scoring module 304 may be configured to generate an HRD score, at least in part, by utilizing the number and/or nature of rearrangements and/or sequence context surrounding the breakpoints of the rearrangements, as determined by the fusion caller 301.

The HRD scoring module 304 may be configured to generate an HRD score, at least in part, by summarizing the number of breakpoints and/or segments with deletion per sample, as determined by the deletion caller 302. The segments may indicate different copy number states in the genome, the more copy number states, the more genome instability, and potentially indicative of an underlying HRR deficiency. Generally, the HRD scoring module 304 may be configured for:

smoothing segments less than 3 MB long between segments that are within 1.5 standard deviations of the segment mean
removing segments that are 90% of the length of the chromosome
filtering out segments below a configurable length threshold (10 Mb) to exclude segments that may be products of non HRD mechanisms
counting the number of breakpoints between adjacent segments
filtering segments from the deletion caller for recurrent segments found in normals or tumor not detected samples (that may be uninformative)
counting the number segments with deletion (loh, homdel, or coverage based deletion).
adding the number of breakpoints and deletion segments In an embodiment, the determination of the HRD score may be based on one or more metrics that are correlated with HRD status. For example, the one or more metrics may comprise one or more of, Loss of Heterozygosity (LOH), Telomere Allele Imbalance (TAI), Large Scale Transitions (LST), combinations thereof, and the like.

LST may refer to breakpoints between adjacent regions of at least 10 Mb, after filtering 3 MB regions. The number of LSTs correlates with the number of adjacent breakpoints and gene mutation status. A 3 MB cut-off may be used to remove small scale variation, unrelated to HRD, from large scale variation, which represent mostly interchromosomal translocations.

Figure 8:
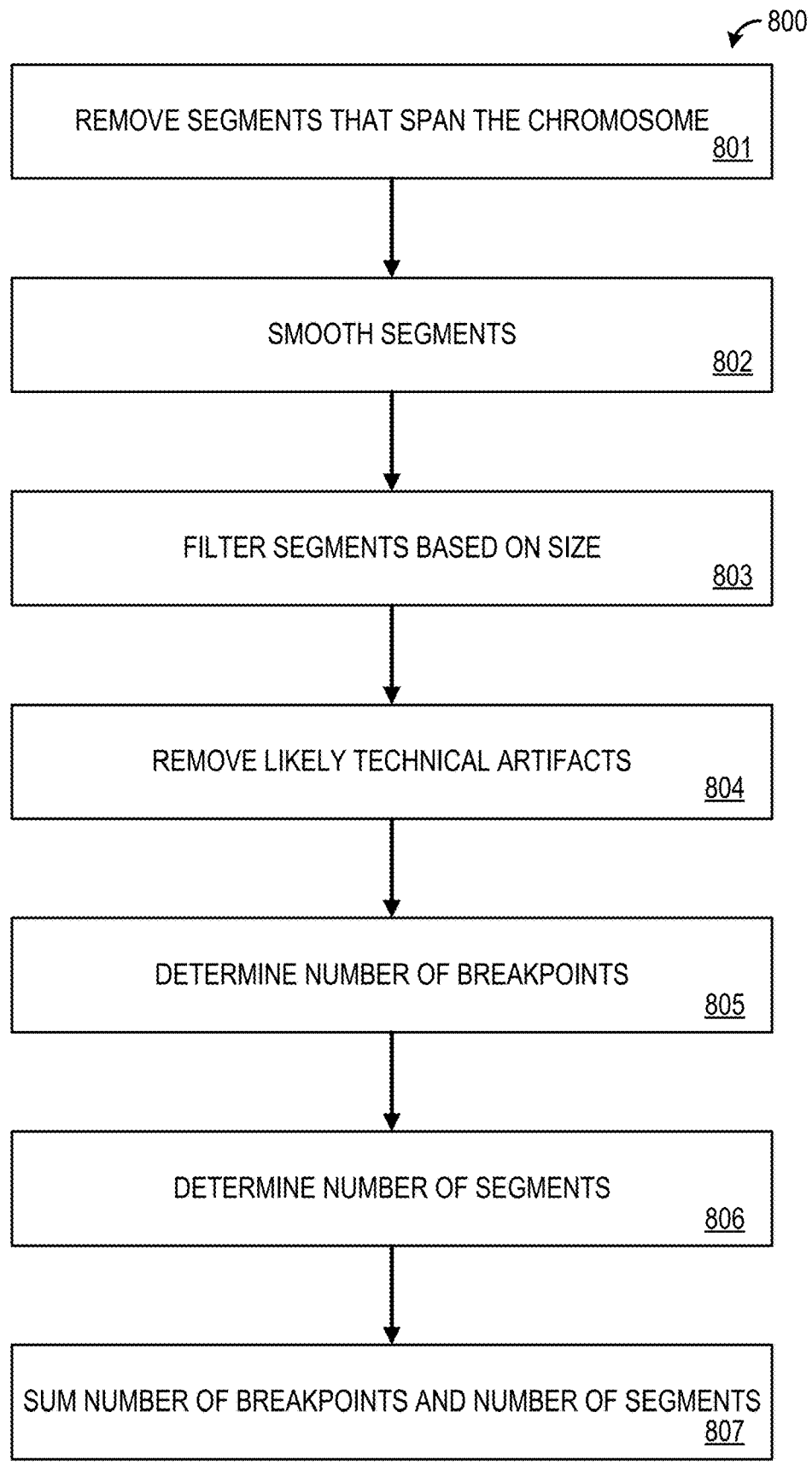
FIG. 8 illustrates a schematic diagram of a method for HRD scoring according to an embodiment of the present disclosure.

In an embodiment, HRD scoring module 304 may be configured to determine an HRD score according to a method 800 as shown in FIG. 8. The HRD scoring module 304 may access deletion call data comprising segments used for deletion calling. Segments that span the length of the chromosome (>90%) may be removed at 801. These segments are likely to arise from non-disjunction and not HRD. Segments with lengths less than 3 MB may be smoothed at 802. Smoothing segments may comprise combining segments that are less than 3 MB apart and in which the second segment has a segment mean (e.g., normalized coverage in the segment) within 1.5 standard deviations of the prior segment. Segments may be filtered based on size at 803. For example, segments that are less than 10 Mb may be removed. Small scale variation segments typically correspond to intrachromosomal rearrangements, unrelated to HRD, vs LSTs represent mostly interchromosomal translocations. Segments in bins that are recurrent (e.g., >10 times) in a large cohort of samples (including patient samples, tumor not detected samples and healthy normal samples) and are likely to represent technical artifacts may be removed at 804. Bin size may be, for example, 500 bp from either start/end of a segment. A number of breakpoints between segments that are adjacent within a certain bp distance may be determined at 805. A number of segments that have LOH, Homdel, and/or Deletion labels may be determined at 806. The number of breakpoints and the number of segments may be summed to determine an HRD score at 807.

The HRD scoring module 304 may be configured to determine the tumor fraction from the sample, using for example the max somatic allele fraction (MSAF). MSAF may comprise the maximum percentage of variants in a sample comprising any somatic variant that is not annotated as clonal hematopoiesis origin and is a fusion or non-synonymous SNV or Indel, expressed as a fraction. If there are no somatic variants in the SNV, Indel, Fusion, or de novo fusion outputs, the MSAF may be 0. For variants occurring on an amplified gene on chromosome X in male samples, the percentage may be adjusted to account for a haploid chromosome as follows:

adjusted percentage=variant percentage/log 2(gene $CN*2$), where gender may be predicted by the sequence analysis pipeline 112. For all other variants occurring on an amplified gene, the percentage may be adjusted as follows:

adjusted percentage=variant percentage/log 2(gene CN). The tumor fraction may be used in the HRD scoring module 304 to obtain an adjusted estimate of HRD score in the context of samples with low tumor shedding.

Figure 9:
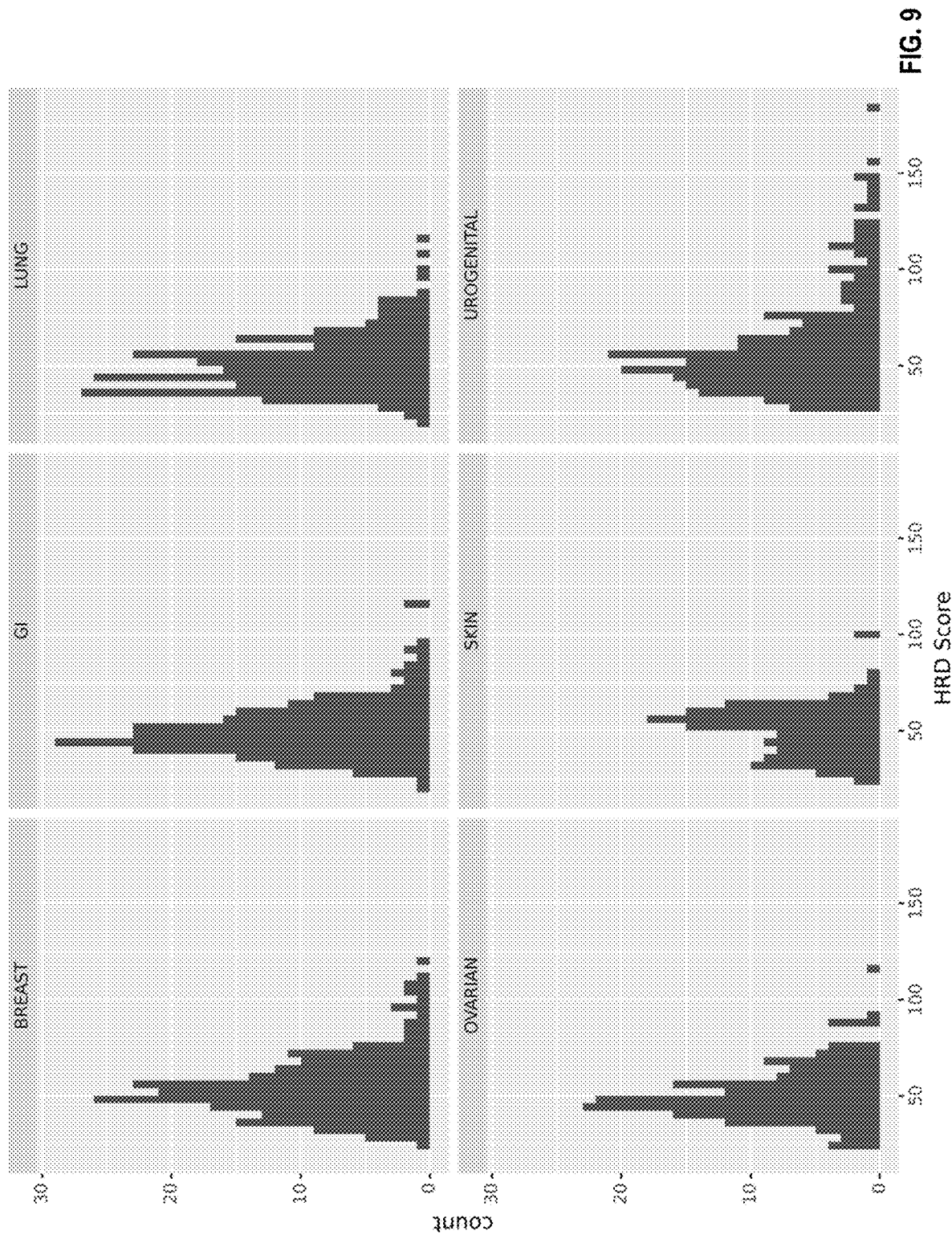
FIG. 9 shows a histogram of example HRD Scores across cancer types.

FIG. 9 shows a histogram of example HRD Scores across cancer types. Clinical patient samples from the OMNI 2.12 panel were evaluated for HRD Score (n=200 for all cancer types except Ovarian and Skin, where n=139 and n=113, respectively). Longer tails in HRD Scores (>100) were observed in Breast and Urogenital cancer types.

The HRD score module 305 may be configured to output HRD score data. The HRD score data may comprise, for example, an HRD score and/or a MSAF. In an embodiment, the MSAF may inform the score (e.g., a low tumor fraction and low score, may pass a threshold under certain conditions, whereas a high tumor fraction and a low score may not).

The HRD score may be compared to a threshold. If the HRD score for a sample exceeds the threshold, the sample may be determined as HRD positive. A threshold may be empirically determined through analysis of populations per tumor type deemed HRD +ve and HRD −ve by the presence of specific loss of function genomic biomarkers (e.g. BRCA½ biallelic inactivation), or based on populations per tumor type who did or did not clinically respond to PARP inhibitors. (Responders should likely have a high HRD score).

Returning to FIG. 3, the aggregator 305 may be configured to provide a sample-level summary from the other HRD modules (the fusion caller 301, the deletion caller 302, the annotation 303, and/or the HRD scoring module 304) and/or determine HRR genes with biallelic inactivation in a sample. The aggregator 305 may be configured to analyze data from the fusion caller 301, the deletion caller 302 (e.g., the deletion call data), the annotation module 303 (e.g., the annotation data), and/or the HRD scoring module 304 (e.g., the HRD score data).

In an embodiment, the aggregator 305 can receive/retrieve annotation data comprising de novo fusion calls with functional impact and somatic calls; SNV calls comprising some or all SNV results from the copy number module 115 with clinical significance annotation, deleterious annotations, and/or reversion annotations; and/or data comprising SNV/Indel calls with clinical significance annotation, molecular consequence, and functional impact. In an embodiment, the aggregator 305 can receive/retrieve deletion call data comprising some or all reportable genes with one of the following conditions: Homozygous Deletion, LOH, coverage-based deletion, copy number neutral LOH, or no call; and/or genomewide LOH call data comprising calls of genomewide LOH based on segments. In an embodiment, the aggregator 305 can receive/retrieve HRD score data comprising HRD scores and/or max somatic allele fractions. In an embodiment, the aggregator 305 can receive/retrieve fusion data comprising some or all fusions as detected by the fusion caller 301, as well as ancillary data for in depth analysis of fusion events.

In one embodiment, the aggregator 305 may determine the total number of rearrangements in a sample, or a subset of these rearrangements with features/signatures characteristic of HRD, such as tandem duplications or deletions, clustered and non-clustered deletions (>100 kb), inversions and interchromosomal translocations frequently attributed to loss of BRCA½ function, as example. In another embodiment, the aggregator 305 may determine the total number of Indels in a sample, or a subset of these indels with flanking sequence context with microhomology that is indicative of underlying HRD, also previously attributed to loss of BRCA½ function.

Biallelic inactivation occurs when both copies of a gene exhibit loss-of-function; this can occur through the presence of a pathogenic variant, a deletion, or a rearrangement in both alleles of the gene. Patients with biallelic inactivation have been shown to have a stronger HRD phenotype compared to patients with only one allele inactivated and may show improved clinical benefit when treated with PARP compared to monoallelic inactivation. The aggregator 305 may be configured to determine if a gene in a sample is associated with biallelic inactivation if the gene is an HRR gene and at least one of the following is true:

Gene has at least two different deleterious SNVs or indels
  Gene is in at least one fusion/rearrangement and has at least one deleterious SNV or indel
  Gene has at least one deleterious SNV or indel and has LOH or a coverage-based deletion
  Gene is in at least one fusion/rearrangement and has LOH or a coverage-based deletion
  Gene is in two different fusions/rearrangements (not including reciprocal fusions or the same fusion gene pair with different breakpoints)
  Gene has a homozygous deletion The aggregator 305 may be configured to determine/retrieve/receive an HRR gene list. The aggregator 305 may be configured to flag samples that have a homozygous deletion and fusion detected in the same HRR gene.

The aggregator 305 may be configured to generate data summarizing sample-level HRD information, including (but not limited to) the number of bi-allelic mutations, HRD score and the max somatic allele fraction (MSAF).

The output module 306 may be configured to output a user-friendly summary of some or all the variants called by the copy number module 115 and the HRD module 300 for manual review purposes. The output module 306 may be configured to generate a sample-level data that comprises metrics from both the copy number module 115 and the HRD module 300 outputs. The output module 306 may be configured to generate a report that summarizes manual review flags raised from the HRD module 300. The report may indicate the samples and variants requiring manual review. The output module 306 may be configured to generate a report comprising sample level and variant level QC metrics. The output module 306 may be configured to obtain sample and variant level QC metrics to generate the report. The output module 306 may be configured to generate a report that summarizes variant calls and manual review comments from both the copy number module 115 and the HRD module 300. The output module 306 may be configured to generate a table of deletion calls, and corresponding cut-off thresholds.

Figure 10:
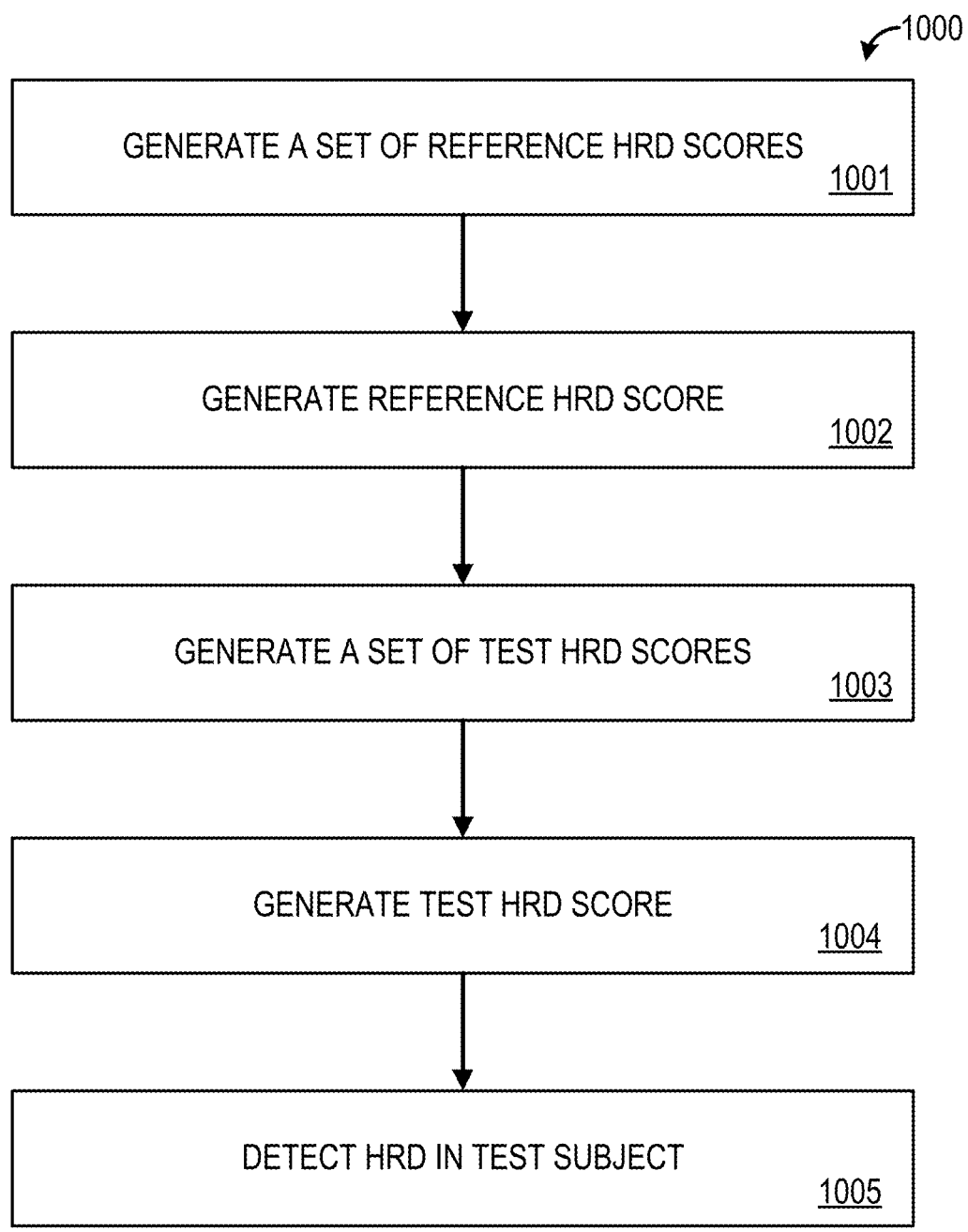
FIG. 10 is a flow chart that schematically depicts exemplary method steps of generating a homologous recombination DNA repair deficiency (HRD) score and detecting a HRD in a test subject according to some embodiments.

FIG. 10 is a flow chart that schematically depicts exemplary method steps of generating one or more HRD scores (e.g., using the HRD module 300 of system 100) and detecting a HRD in a test subject according to some embodiments. As shown, method 1000 includes generating a reference HRD score for the genes in a set of HRR genes (e.g., homologous recombination repair (HRR) genes) from sequence information derived from cell-free nucleic acids (cfDNAs) obtained from reference subjects that have a given cancer type to produce a set of reference HRD scores (step 1001). In some embodiments, the set of HRR genes is selected from those listed in Table 1. A given reference HRD score typically includes a prevalence of a given HRD nucleic acid variant. A reference HRD score may be generated based on the set of reference HRD scores (step 1002). The reference HRD score may then be used to detect HRD in test subjects. As shown in method 1000, this generally includes generating a test HRD score for genes in the set of HRR genes from sequence information derived from cfDNAs obtained from a test subject having the given cancer type to produce a set of test HRD scores (step 1003). A given test HRD score typically includes a prevalence of the given HRD nucleic acid variant. In some embodiments, a given HRD nucleic acid variant produces monoallelic inactivation or biallelic inactivation of the corresponding HRR gene. To detect HRD in test subjects, method 1000 also includes generating a test HRD score from the set of test HRD scores (step 1004) and detecting a HRD in the test subject when the test HRD score exceeds the reference HRD score.

FIG. 11 is a flow chart that schematically depicts exemplary method steps of determining a HRD status of a test subject having a given cancer type (e.g., using the HRD module 300 of system 100) according to some embodiments. As shown, method 1100 includes generating a test HRD score for genes in a set of HRR genes (e.g., homologous recombination repair (HRR) genes) from sequence information derived from cell-free nucleic acids (cfDNA) obtained from the test subject to produce a set of test HRD scores (step 1101). A given test HRD score generally includes a prevalence of the given HRD nucleic acid variant. In some embodiments, the set of HRR genes is selected from those listed in Table 1. Method 1100 also includes generating a test HRD score from the set of test HRD scores (step 1102). In addition, method 1100 also includes comparing the test HRD score to the reference HRD score in which test HRD scores that are above the reference HRD score indicate that those test HRD scores are from test subjects having a HRD and in which test HRD scores that are at or below the reference HRD score indicate that those test HRD scores are from test subjects lacking HRD to thereby determine the HRD status of the test subject having the given cancer type (step 1103).

The method 1100 may further comprise generating a reference HRD score for one or more genes in a set of homologous recombination repair (HRR) genes from sequence information derived from cell-free nucleic acids (cfDNA) obtained from one or more reference subjects that have one or more cancer types to produce a set of reference HRD scores, wherein a given reference HRD score comprises a prevalence of a given HRD nucleic acid variant and generating the reference HRD score from the set of reference HRD scores.

To further illustrate, FIG. 12 is a flow chart that schematically depicts exemplary method steps of detecting a HRD in a subject (e.g., using the HRD module 300 of system 100) according to some embodiments. As shown, method 1200 includes determining a presence or absence of at least one HRD nucleic acid variant in sequence information derived from cell-free nucleic acids (cfDNA) obtained from the subject using (i) a first probability that the sequence information comprises a first state and a second probability that the sequence information comprises a second state in which the first or second state comprises at least a first HRD nucleic acid variant (e.g., using a CNV caller described herein) and/or (ii) one or more aligned contiguous sequences (contigs) generated from the sequence information in which the aligned contigs comprise at least a second HRD nucleic acid variant (e.g., using a de novo fusion caller described herein), to thereby detect the HRD in the subject (step 1201). Some embodiments of method 1200 include using only one of steps (i)-(ii), whereas other embodiments include using each of steps (i)-(ii).

FIG. 13 is a flow chart that schematically depicts exemplary method steps of treating a disease in a subject according to some embodiments. As shown, method 1300 includes administering one or more therapies (e.g., a PARP inhibitor, a BER inhibitor, etc.) to a subject having the disease (e.g., a given cancer type) and a DNA damage repair deficiency (DDRD) (e.g., a HRD) associated with the disease, which DDRD is detected by determining a presence of at least one HRD nucleic acid variant in sequence information derived from cell-free nucleic acids (cfDNA) obtained from the subject using (i) a first probability that the sequence information comprises a first state and a second probability that the sequence information comprises a second state in which the first or second state comprises at least a first HRD nucleic acid variant (e.g., using a CNV caller described herein) and/or (ii) one or more aligned contiguous sequences (contigs) generated from the sequence information in which the aligned contigs comprise at least a second HRD nucleic acid variant (e.g., using a de novo fusion caller described herein), to thereby detect the HRD in the subject (step 1301). Some embodiments of method 1300 include using only one of steps (i)-(ii), whereas other embodiments include using each of steps (i)-(ii).

In some embodiments, the first HRD nucleic acid variant includes a homozygous deletion, a loss-of-heterozygosity (LOH) variant (e.g., a gene-specific LOH variant, a copy number neutral LOH variant, and/or a genome-wide LOH variant), a copy number variation (CNV), and/or the like. In certain embodiments, the second HRD nucleic acid variant includes a structural rearrangement (e.g., a truncating rearrangement, a multi-exon deletion, and/or the like). In some embodiments, the first and/or second HRD nucleic acid variant includes a single nucleotide variation (SNV), an indel, and/or the like.

The technique of steps (i) and/or (ii) in the methods may comprise aligning at least segments of the sequence information to at least one reference sequence. The methods may comprise using only one of steps (i)-(ii). The methods may comprise using each of steps (i)-(ii).

At least one homologous recombination repair (HRR) gene in the methods may comprise the HRD nucleic acid variant. The HRR gene in the methods may be selected from the group consisting of: ATM, ATR, BARD1, BRCA1, BRCA2, BRIP1, CDK12, CHEK1, CHEK2, FANCA, FANCL, NBN, PALB2, RAD51, RAD51B, RAD51C, RAD51D, RAD54L, HDAC2, MRE11, PPP2R2A, XRCC5, WRN, MLH1, FANCC, BAP1, XRCC2, XRCC3, and RAD50. The set of HRR genes may comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, or more genes.

One or more of the HRD nucleic variants in the methods may produce biallelic inactivation of a given HRR gene. One or more of the HRD nucleic variants in the methods may produce monoallelic inactivation of a given HRR gene. The HRD nucleic acid variant in the methods may correlate with the subject having a disease. It may be unknown whether the subject has a disease. It may be known that the subject has a disease. The disease may be cancer.

The methods may comprise administering one or more therapies to the subject to treat the disease. The therapies may comprise at least one poly ADP ribose polymerase (PARP) inhibitor. The therapies may comprise at least one base excision repair (BER) inhibitor.

Step (i) of the methods may comprise generating the first probability that the sequence information includes the first state, generating the second probability that the sequence information includes the second state, comparing the first probability and the second probability, and generating a prediction of whether the sequence information includes the first state or the second state based on the comparing.

Step (i) of the methods may comprise generating via a first probabilistic distribution, a first model of allelic counts based on one or more germline single nucleotide polymorphism (SNP) positions associated with at least one genetic locus in the sequence information, the first model representing at least one somatic homozygous deletion, generating via a second probabilistic distribution, a second model of allelic counts based on the one or more germline SNP positions associated with the genetic locus in the sequence information, the second model representing at least one somatic heterozygous deletion, comparing a first output of the first model and a second output of the second model, and generating a prediction that the somatic homozygous deletion for the genetic locus exists in the sequence information based on the comparison.

Step (i) of the methods may comprise generating the first probability that the sequence information includes a somatic homozygous deletion, generating the second probability that the sequence information includes a somatic heterozygous deletion, comparing the first probability and the second probability, and generating a prediction of whether the sequence information includes the somatic homozygous deletion or the somatic heterozygous deletion based on the comparing.

Step (ii) of the methods may comprise aligning a plurality of sequence reads to a reference sequence, determining one or more breakpoints in an alignment of at least one sequence read of the plurality of sequence reads to the reference sequence, identifying any sequence reads associated with the one or more breakpoints in the alignment as candidate fusion sequence reads, determining candidate fusion sequence reads associated with common breakpoints of one or more breakpoints, grouping the candidate fusion sequence reads based on one or more common breakpoints, assembling the candidate fusion sequence reads in each group into one or more contigs, aligning the contigs from each group to the reference sequence, determining, based on the alignments of the contigs from each group, one or more candidate fusion events, applying one or more criteria to the one or more candidate fusion events, and determining, based on applying the one or more criteria to the one or more candidate fusion events, one or more fusion events that comprise the second HRD nucleic acid variant.

The methods may comprise using a CNV and/or de novo fusion caller to detect the HRD or the HRD in the subject. The gene may comprise the HRD nucleic acid variant.

Figure 14:
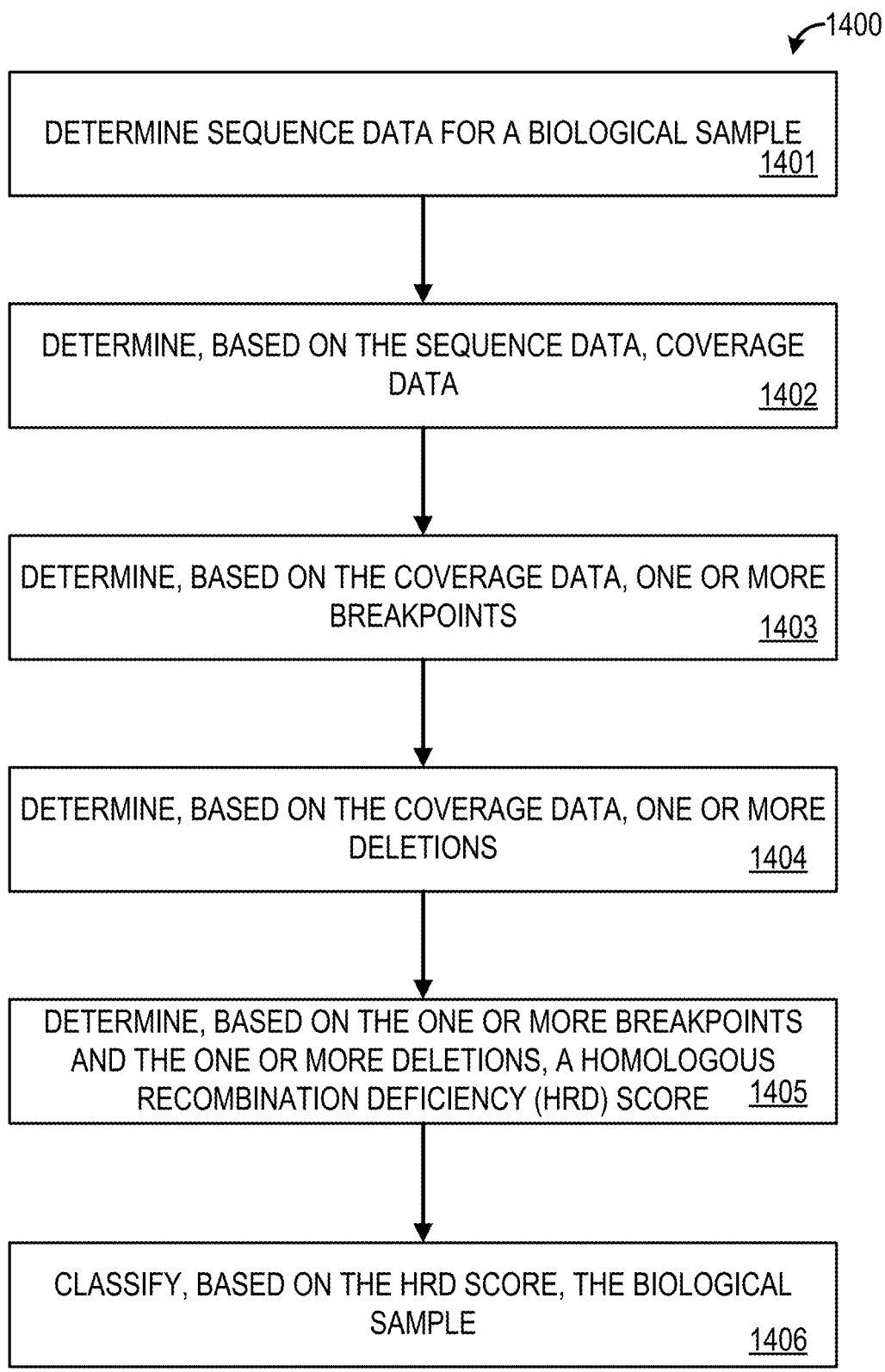
FIG. 14 is a flow chart that schematically depicts exemplary method steps of detecting a DNA damage repair deficiency (DDRD) in a subject according to some embodiments.

In an embodiment, shown in FIG. 14, a method 1400 for determining HRD status is disclosed. In an embodiment, the sequence QC component 113, the copy number module 115, and/or the HRD module 300, alone and/or in a combination thereof may be configured to access the sequence read datastore 150 and/or the analysis datastore 117 and perform the method 1400 in whole and/or in part. The method 1400 may be performed in whole or in part by a single computing device, a plurality of computing devices, and the like. The method 1400 may comprise determining sequence data for a biological sample at step 1401. The biological sample may comprise cell free DNA (cfDNA). The method 1400 may comprise determining, based on the sequence data, coverage data at step 1402. The method 1400 may comprise determining, based on the coverage data, one or more breakpoints associated with one or more fusion events at step 1403. The method 1400 may comprise determining, based on the coverage data, one or more deletions associated with one or more genes at step 1404. The method 1400 may comprise determining, based on the one or more breakpoints and the one or more deletions, a homologous recombination deficiency (HRD) score at step 1405. The method 1400 may comprise classifying, based on the HRD score, the biological sample at step 1406. The method 1400 may comprise classifying, based on the HRD score, the biological sample as HRD positive at step 1406. The method 1400 may comprise classifying, based on the HRD score, the biological sample as HRD negative at step 1406.

Determining sequence data for the biological sample may comprise sequencing a panel of one or more HRR genes. The one or more HRR genes may be selected from the group consisting of: ATM, ATR, BARD1, BRCA1, BRCA2, BRIP1, CDK12, CHEK1, CHEK2, FANCA, FANCL, NBN, PALB2, RAD51, RAD51B, RAD51C, RAD51D, RAD54L, HDAC2, MRE11, PPP2R2A, XRCC5, WRN, MLH1, FANCC, BAP1, XRCC2, XRCC3, and RAD50.

The biological sample may be associated with a subject having a disease. The disease may be cancer. The coverage data may be associated with a plurality of bins. The plurality of bins may represent regions of a chromosome.

Determining, based on the coverage data, one or more breakpoints associated with one or more fusion events may comprise aligning a plurality of sequence reads from the sequence data to a reference sequence, determining one or more breakpoints in an alignment of a plurality of sequence reads of the plurality of sequence reads to the reference sequence, identifying any sequence reads associated with the one or more breakpoints in the alignment as candidate fusion sequence reads, determining candidate fusion sequence reads associated with common breakpoints of one or more breakpoints, grouping the candidate fusion sequence reads based on one or more common breakpoints, assembling the candidate fusion sequence reads in the groups into one or more contigs, aligning the contigs from the groups of the plurality of groups to the reference sequence, determining, based on the alignments of the contigs from the groups, one or more candidate fusion events, applying one or more criteria to the one or more candidate fusion events, and determining, based on applying the one or more criteria to the one or more candidate fusion events, one or more fusion events.

Determining, based on the coverage data, the one or more deletions associated with one or more genes may comprise determining, based on the coverage data, a plurality of segments, where the plurality of segments are separated by a change point. Determining the plurality of segments may comprise applying a segmentation algorithm. The segmentation algorithm may comprise a circular binary segmentation algorithm. The change points may correspond to positions where the coverage data indicates an underlying DNA copy number has changed. The one or more deletions may comprise one or more of a homozygous deletion or a loss-of-heterozygosity (LOH) deletion.

The method 1400 may further comprise comparing the plurality of segments to a reference sequence to identify a subset of the plurality of segments comprising at least one deletion, removing, from the subset of the plurality of segments, any segment that spans a length of a chromosome, combining, in the subset of the plurality of segments, any segments that are less than a threshold distance apart, removing, from the subset of the plurality of segments, any segment with a length less than a threshold length, and removing, from the subset of the plurality of segments, any segment associated with a technical artifact. The method 1400 may further comprise determining, based on one or more remaining segments in the subset of the plurality of segments and based on the one or more breakpoints associated with the one or more fusion events, a number of breakpoints between segments that are adjacent within a threshold.

The method 1400 may further comprise determining, based on one or more remaining segments in the subset of the plurality of segments, a number of segments associated with a single copy of a region of interest or associated with both copies of the region of interest being deleted.

Determining, based on the one or more breakpoints and the one or more deletions, the HRD score may comprise summing a number of breakpoints and a number of segments.

The method 1400 may further comprise determining, based on the sequencing data, a presence of one or more genomic rearrangements. Determining the HRD score may be further based on the one or more genomic rearrangements. Determining the HRD score may comprise summing a number of breakpoints, a number of segments, and a number of genomic rearrangements.

The method 1400 may further comprise determining a max somatic allele fraction (MSAF). Determining the MSAF may comprise determining, based on the sequence data, a maximum percentage of variants in the biological sample comprising any somatic variant that is not annotated as clonal hematopoiesis origin and is a fusion or non-synonymous SNV or Indel.

The method 1400 may further comprise annotating one or more variants contained in the sequence data. Annotating one or more variants contained in the sequence data may comprise determining a clinical significance annotation associated with the one or more variants impact to human health.

The method 1400 may further comprise aggregating the sequence data, the coverage data, the one or more breakpoints, the one or more deletions, and the HRD score. The method 1400 may further comprise outputting the aggregated sequence data, coverage data, one or more breakpoints, one or more deletions, and HRD score.

Classifying, based on the HRD score, the biological sample as HRD positive may comprise determining that the HRD score exceeds a threshold. Classifying, based on the HRD score, the biological sample as HRD negative may comprise determining that the HRD score does not exceed a threshold. The method 1400 may further comprise determining the threshold based on one or more reference HRD scores. The threshold may comprise a reference HRD score. Sequence information derived from cell-free nucleic acids (cfDNA) obtained from one or more reference subjects may be used to produce a set of reference HRD scores. The reference subjects may have the same condition as the subject from whom the biological sample was taken. For example, the reference subjects and the subject from whom the biological sample was taken may have the same disease (e.g., cancer and/or cancer type). The reference HRD score may be generated from the set of reference HRD scores. For example, by taking an average (or other statistical analysis) of the set of reference HRD scores.

The method 1400 may further comprise administering, based on classifying the biological sample as HRD positive, a therapy. The therapy may be a poly ADP ribose polymerase (PARP) inhibitor or a base excision repair (BER) inhibitor. The PARP inhibitor may be at least one of: VELIPARIB, OLAPARIB, TALAZOPARIB, RUCAPARIB, NIRAPARIB, PAMIPARIB, CEP 9722, E7016, E7449, or 3-Aminobenzamide. The therapy may be a combination of a PARP inhibitor and radiotherapy.

The various processing operations and/or methods depicted in the Figures may be accomplished using some or all of the system components described in detail herein and, in some implementations, various operations may be performed in different sequences and various operations may be omitted. Additional operations may be performed along with some or all of the operations shown in the depicted flow diagrams. One or more operations may be performed simultaneously. Accordingly, the operations as illustrated (and described in greater detail herein) are provided as example and, as such, should not be viewed as limiting.

Computer Implementation

The present methods can be computer-implemented, such that any or all of the operations described in the specification or appended claims other than wet chemistry steps can be performed in a suitable programmed computer. The computer can be a mainframe, personal computer, tablet, smart phone, cloud, online data storage, remote data storage, or the like. The computer can be operated in one or more locations.

Various operations of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like.

The present disclosure also includes an article of manufacture for analyzing a nucleic acid population that includes a machine-readable medium containing one or more programs which when executed implement the steps of the present methods.

The disclosure can be implemented in hardware and/or software. For example, different aspects of the disclosure can be implemented in either client-side logic or server-side logic. The disclosure or components thereof can be embodied in a fixed media program component containing logic instructions and/or data that when loaded into an appropriately configured computing device cause that device to perform according to the disclosure. A fixed media containing logic instructions can be delivered to a viewer on a fixed media for physically loading into a viewer's computer or a fixed media containing logic instructions may reside on a remote server that a viewer accesses through a communication medium to download a program component.

The present disclosure provides computer control systems that are programmed to implement methods of the disclosure. Returning to FIG. 1, the processor 120 may include a single core or multi core processor, or a plurality of processors for parallel processing. The storage device 122 may include random-access memory, read-only memory, flash memory, a hard disk, and/or other type of storage. The computer system 110 may include a communication interface (e.g., network adapter) for communicating with one or more other systems, and peripheral devices, such as cache, other memory, data storage and/or electronic display adapters. The components of the computer system 110 may communicate with one another through an internal communication bus, such as a motherboard. The storage device 122 may be a data storage unit (or data repository) for storing data. The computer system 110 may be operatively coupled to a computer network ("network") with the aid of the communication interface. The network may be the Internet, an internet and/or extranet, or an intranet and/or extranet that is in communication with the Internet. The network in some cases is a telecommunication and/or data network. The network may include a local area network. The network may include one or more computer servers, which can enable distributed computing, such as cloud computing. The network, in some cases with the aid of the computer system 110, may implement a peer-to-peer network, which may enable devices coupled to the computer system 120 to behave as a client or a server.

The processor 120 may execute a sequence of machine-readable instructions, which can be embodied in a program or software. The instructions may be stored in a memory location, such as the storage device 122. The instructions can be directed to the processor 120, which can subsequently program or otherwise configure the processor 120 to implement methods of the present disclosure. Examples of operations performed by the processor 120 may include fetch, decode, execute, and writeback.

The processor 120 may be part of a circuit, such as an integrated circuit. One or more other components of the system 100 may be included in the circuit. In some cases, the circuit may include an application specific integrated circuit (ASIC).

The storage device 122 may store files, such as drivers, libraries and saved programs. The storage device 122 can store user data, e.g., user preferences and user programs. The computer system 110 in some cases may include one or more additional data storage units that are external to the computer system 110, such as located on a remote server that is in communication with the computer system 110 through an intranet or the Internet.

The computer system 110 can communicate with one or more remote computer systems through the network. For instance, the computer system 110 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 110 via the network.

Methods as described herein can be implemented by way of machine (e.g., computer processor) executable code stored on an electronic storage location of the computer system 110, such as, for example, on the storage device 122. The machine executable or machine readable code can be provided in the form of software (e.g., computer readable media). During use, the code can be executed by the processor 120. In some cases, the code can be retrieved from the storage device 122 and stored on the storage device 122 for ready access by the processor 120.

The code may be pre-compiled and configured for use with a machine having a processor adapted to execute the code, or can be compiled during runtime. The code can be supplied in a programming language that can be selected to enable the code to execute in a precompiled or as-compiled fashion.

Aspects of the systems and methods provided herein, such as the computer system 110, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk.

"Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible, storage media, "media" may include other types of (intangible) media.

"Storage" media, terms such as computer or machine "readable medium" refer to any tangible (such as physical), non-transitory, medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 110 can include or be in communication with an electronic display 935 that comprises a user interface (UI) for providing, for example, a report. Examples of UI's include, without limitation, a graphical user interface (GUI) and web-based user interface.

Methods and systems of the present disclosure can be implemented by way of one or more algorithms. An algorithm can be implemented by way of software upon execution by the processor 120.

The present methods can be used to diagnose the presence or absence of conditions, particularly cancer, in a subject, to characterize conditions (e.g., staging cancer or determining heterogeneity of a cancer), select a treatment for a condition, monitor response to treatment of a condition, effect prognosis risk of developing a condition or subsequent course of a condition.

Various cancers may be detected using the present methods. Cancer cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as rare mutations. This phenomenon may be used to detect the presence or absence of cancer in individuals using the methods and systems described herein.

In certain embodiments, the methods and aspects disclosed herein are used to diagnose a given disease, disorder or condition in patients. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinoma, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

Non-limiting examples of other genetic-based diseases, disorders, or conditions that may be evaluated using the methods and systems disclosed herein include DNA damage repair deficiency, achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (scid), sickle cell disease, spinal muscular atrophy, Tay-Sachs, thalassemia, trimethylaminuria, Turner syndrome, velocardiofacial syndrome, WAGR syndrome, Wilson disease, or the like.

Cancers can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers progress, becoming more aggressive and genetically unstable. Other cancers may remain benign, inactive or dormant. The system and methods of this disclosure may be useful in determining disease progression.

The present analysis is also useful in determining the efficacy of a particular treatment option. Successful treatment options may increase the amount of copy number variation or rare mutations detected in a subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the present methods can be used to monitor residual disease or recurrence of disease.

The present methods can also be used for detecting genetic variations in conditions other than cancer. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and rare mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation and rare mutation analyses alone or in combination.

Exemplary Precision Treatments

The precision diagnostics provided by the improved computer system 110 may result in precision treatment plans, which may be identified by the computer system 110 (and/or curated by health professionals). For example, one type of precision diagnostic and treatment may relate to genes in the homologous recombination repair (HRR) pathway.

Homologous recombination is a type of genetic recombination in which nucleotide sequences are exchanged between two similar or identical molecules of DNA. It is most widely used by cells to accurately repair harmful breaks that occur on both strands of DNA, known as double-strand breaks (DSB). HRR provides a mechanism for the error-free removal of damage present in DNA that has replicated (S and G2 phases), to eliminate chromosomal breaks before the cell division occurs. The primary model for how homologous recombination repairs double-strand breaks in DNA is homologous recombination repair pathway which mediates the double-strand break repair (DSBR) pathway and the synthesis-dependent strand annealing (SDSA) pathway. Germline and somatic deficiencies in homologous recombination genes have been strongly linked to breast, ovarian and prostate cancers.

The number and types of variant nucleotides in a sample can provide an indication of the amenability of the subject providing the sample to treatment, i.e., therapeutic intervention. For example, various poly ADP ribose polymerase (PARP) inhibitors have been shown to stop the growth of tumors from breast, ovarian and prostate cancers caused by hereditary mutations in the BRCA1 or BRCA2 genes. Some of these therapeutic agents may inhibit base excision repair (BER), which may compensate for the deficiency of HRR.

On the other hand, certain BRCA and HRR wildtype patients may not achieve clinical benefit from treatment with a PARP inhibitor. Furthermore, not all ovarian cancer patients with a BRCA mutation will respond to a PARP inhibitor. Moreover, different types of mutations may indicate different therapies. For example, somatic heterozygous deletions in HRR genes may indicate a different therapy than somatic homozygous deletions. Thus, the state of genetic material may influence therapy. In one example, a PARP inhibitor may be administered to an individual harboring a somatic homozygous deletion in a HRR gene, but not to an individual harboring a wildtype allele or somatic heterozygous deletions in the HRR gene.

Nucleotide variations in sequenced nucleic acids can be determined by comparing sequenced nucleic acids with a reference sequence. The reference sequence is often a known sequence, e.g., a known whole or partial genome sequence from an object, whole genome sequence of a human object. The reference sequence can be hG19. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeds a threshold, then a variant nucleotide can be called at the designated position. The threshold can be a simple number, such as at least 1, 2, 3, 4, 5, 6, 7, 8, 9, or 10 sequenced nucleic acid within the subset including the nucleotide variant or it can be a ratio, such as a least 0.5, 1, 2, 3, 4, 5, 10, 15, or 20 of sequenced nucleic acids within the subset include the nucleotide variant, among other possibilities. The comparison can be repeated for any designated position of interest in the reference sequence. Sometimes a comparison can be performed for designated positions occupying at least 20, 100, 200, or 300 contiguous positions on a reference sequence, e.g., 20-500, or 50-300 contiguous positions.

EXAMPLES

Example 1: Landscape of Homologous Recombination Repair (HRR) Mutations in Prostate Cancer Profiled by ctDNA Next-Generation Sequencing

BACKGROUND

PARP inhibition can cause synthetic lethality and increased therapeutic sensitivity in patients with HRR deficiency (HRD), which can be detected through the molecular profiling of HRR genes. For example, the FDA recently approved the use of PARP inhibitors olaparib (de Bono et al., "Olaparib for Metastatic Castration-Resistant Prostate Cancer," *N Engl J Med.*, 382(22):2091-2102 (2020)) and rucaparib (Abida et al., "Non-BRCA DNA Damage Repair Gene Alterations and Response to the PARP Inhibitor Rucaparib in Metastatic Castration-Resistant Prostate Cancer: Analysis From the Phase II TRITON2 Study," *Clin Cancer Res.*, 10.1158/1078-0432.CCR-20-0394 (2020)) in metastatic castration-resistant prostate cancer (mCRPC) patients with mutations in HRR genes. Prostate cancer is the most common malignancy in men (Siegel et al., "Cancer statistics, 2020," *CA Cancer J Clin*, 70(1):7-30 (2020)) and has a high prevalence of HRD (20-30%, Athie et al., "Targeting DNA Repair Defects for Precision Medicine in Prostate Cancer" *Curr Oncol Rep*, 21(5):42 (2019); Mateo et al., "Olaparib in patients with metastatic castration-resistant prostate cancer with DNA repair gene aberrations (TOPARP-B): a multicentre, open-label, randomised, phase 2 trial," *Lancet Oncol.*, 21(1):162-174 (2020); Robinson et al., "Integrative clinical genomics of advanced prostate cancer" [published correction appears in Cell. 2015 Jul. 16; 162(2):454]. *Cell*, 161(5):1215-1228 (2015)) in men with advanced prostate cancer. High failure rates for tissue biopsy in metastatic prostate cancer patients (25-75% or even higher (e.g., ≥90%)) (Ross et al., "Predictors of prostate cancer tissue acquisition by an undirected core bone marrow biopsy in metastatic castration-resistant prostate cancer—a Cancer and Leukemia Group B study," Clin Cancer Res, 11(22): 8109-13 (2005); Spritzer et al., "Bone marrow biopsy: RNA isolation with expression profiling in men with metastatic castration-resistant prostate cancer—factors affecting diagnostic success," *Radiology*, 269(3):816-23 (2013); Sailer et al., "Bone biopsy protocol for advanced prostate cancer in the era of precision medicine," *Cancer*, 124(5):1008-1015 (2018)) pose challenges for HRD profiling, underscoring the need for a non-invasive, ctDNA alternative. In ctDNA, detection of copy number loss, a frequent cause of HRD, is further difficult to call due to signal dilution by cell-free leukocytic DNA (Barbacioru et al., "Abstract 435: Cell-free circulating tumor DNA (ctDNA) detects somatic copy number loss in homologous recombination repair genes," *Proceedings: AACR Annual Meeting* 2019; Mar. 29-Apr. 3, 2019; Atlanta, GA). Accordingly, a pipeline was developed that detects loss-of-function SNV/Indels, structural rearrangements, and gene deletions to identify HRD on GuardantOMNI, a 500-gene liquid biopsy panel. This example presents its performance across >650 prostate cancer GuardantOMNI samples.

Methods

Samples from 687 prostate cancer patients were processed on GuardantOMNI RUO (Table 3 presents some of the product features), with median unique coverage of approximately 4600 molecules sequenced to 20,000× read depth. Somatic and germline SNVs and small indels were called using the Guardant bioinformatics pipeline (Heiman et al., "Cell-Free DNA Next-Generation Sequencing Prediction of Response and Resistance to Third-Generation EGFR Inhibitor," *Clin Lung Cancer*, 19(6):518-530 (2018)). A novel HRD module was developed to annotate pathogenic SNV/Indels and identify structural rearrangements, gene-level homozygous deletions, loss-of-heterozygosity (LOH) and genome-wide LOH, comprising of a novel CNV (Barbacioru et al., "Abstract 435: Cell-free circulating tumor DNA (ctDNA) detects somatic copy number loss in homologous recombination repair genes," *Proceedings: AACR Annual Meeting* 2019; Mar. 29-Apr. 3, 2019; Atlanta, GA) and de-novo fusion caller (Yablonovitch et al., "Identification of FGFR⅔ fusions from clinical cfDNA NGS using a de novo fusion caller," 2020 May. ASCO Poster). LOH deletions were determined based on expected allele frequencies given loss of wild-type allele Barbacioru et al., "Abstract 435: Cell-free circulating tumor DNA (ctDNA) detects somatic copy number loss in homologous recombination repair genes," *Proceedings: AACR Annual Meeting* 2019; Mar. 29-Apr. 3, 2019; Atlanta, GA). Loss-of-function variants were analyzed in 24 HRR genes: ATM, ATR, BAP1, BARD1, BRCA1, BRCA2, BRIP1, CDK12, CHEK1, CHEK2, FANCA, FANCL, HDAC2, MRE11, NBN, PALB2, RAD51, RAD50, RAD51B, RAD51C, RAD51D, RAD54L, XRCC2, XRCC3.

TABLE 3

| Product Features | GuardantOMNI ® |
|---|---|
| Number of genes | 500 genes |
| Total size | 2.145 Mb |
| Optimal input material | 5-30 ng cfDNA from ≥2mL plasma |
| Somatic variant detection | Small Nucleotide Variants (SNVs, 496 genes) |
| | Short insertions/deletions (Indels, 496 genes) |
| | Copy Number Amplifications (CNAs, 106 genes) |
| | Fusions (21 genes) |
| Tumor Mutational Burden (TMB) | TMB score (mut/Mb) |
| Microsatellite Instability (MSI) | MSI-High status |
| Homologous Recombination Repair Deficiency (HRD) | 24 HRR genes |
| | SNV/Indel Deleterious and Reversion Annotation |
| | Copy number deletions (homozygous, loh, and undetermined) |
| | Fusions and long (multi-exon) deletions |
| | Biallelic mutation annotation |

Results

Pathogenic alterations in HRR genes were called in 300/687 (43.6%) prostate cancer samples with ctDNA detected: 23% of all samples had a pathogenic somatic or germline SNV/Indel, 7.8% had a homozygous deletion, 3.0% had a rearrangement involving a HRR gene. The majority of SNV/Indels occurred in BRCA2 (32% of all 159 deleterious SNV/Indels) and ATM (35%), similar to tissue (Dhawan et al., "DNA Repair Deficiency Is Common in Advanced Prostate Cancer: New Therapeutic Opportunities," Oncologist, 21(8):940-5 (2016)), but mutations also occurred across an additional 21 genes, including CDK12 (13%), CHEK2 (8%) and NBN (6%). Of prostate patients with a germline BRCA½ SNV/Indel and sufficient tumor shedding for LOH detection (max MAF>20%), 6/12 (50%) also had LOH, compared to 86% in tissue (Jonsson et al., "Tumour lineage shapes BRCA-mediated phenotypes," *Nature*, 571(7766):576-579 (2019)). Homozygous deletions were enriched in BRCA2 (12% of all samples), ATM (6%) and FANCA (5%). Rearrangements, including fusions and multi-exonic deletions, accounted for 6.5% of inactivating HRD mutations detected. In total, 6.8% of prostate samples had a biallelic inactivation involving an SNV, Indel or deletion.

Table 4 further summarizes the GuardantOMNIRUO performance metrics. In particular, the range listed (as noted with *) for 95% LoD includes clinically actionable and non-clinically actionable variants, respectively. The range listed (as noted by **) for 95% LoD is for homozygous and heterozygous deletions, respectively. All metrics were based on 30 ng input using cfDNA clinical samples except for HRR deletions, which were based on in-silico simulations as discussed further below. Specificity is based on false negative variant detection across a large cohort of normal samples.

TABLE 4

| Alteration Type | Reportable Range | 95% Limit of Detection (LoD) | Specificity |
|---|---|---|---|
| SNVs (496 genes) | ≥0.04% | 0.15-0.6%* | >99% |
| Indels (496 genes) | ≥0.1% | 0.4-0.8%* | >99% |
| Activating Fusions (21 genes) | ≥3 molecules | 0.1-0.2% | >99% |
| Amplifications (106 genes) | ≥2.18 copies | 2.18-2.9 copies for 90% of genes | >99% |
| HRR Deletions (24 genes | ≤1.82 | 10-25% tumor fraction** | >99% |
| HRR LoF Fusions (24 genes) | ≥3 molecules | 0.1-0.2% | >99% |

FIG. 15 (panels A-C) are plots of data showing the GuardantOMNIRUO limit of detection (LoD) for HRR deletions and fusions. More specifically, in-silico simulations demonstrated 95% sensitivity in detecting BRCA2 deletions for samples showing a tumor fraction (TF) of 12.5% for homozygous deletions (panel A), 25% for LOH (panel B). LoD for deletions is indicated where zygosity is determinate (DET) and indeterminate (INDET). Experimental using clinical cfDNA containing known fusions and long deletions were assessed using a probit model to determine a 95% LoD of MAF 0.15% (panel C).

Table 5 shows a comparison of HRR gene mutation prevalence in tissue with GuardantOMNI RUO plasma. As shown, a greater proportion of samples had a reportable result in GuardantOMNI RUO compared to FFPE tissue (PROFOUND—FoundationOne (de Bono et al., "Olaparib for Metastatic Castration-Resistant Prostate Cancer," *N Engl J Med.*, 382(22):2091-2102 (2020)), TOPARP—Institute of Cancer Research (Mateo et al., "Olaparib in patients with metastatic castration-resistant prostate cancer with DNA repair gene aberrations (TOPARP-B): a multicenter, open-label, randomized, phase 2 trial," *Lancet Oncol.*, 21(1):162-174 (2020))). *Note that input to GuardantOMNI RUO assay was plasma with varying input volumes (mean=2.78 mL). Higher success rate was expected for Laboratory Diagnostic Test (LDT) given requirements of 10 mL whole blood. Highlighted genes indicate genes not currently on the GuardantOMNI RUO HRR gene list (no deletion and fusion output) but are covered on the OMNI panel, except for FACF and RANCM (**). The MSKCC comparator study is described in Jonsson et al., "Tumour lineage shapes BRCA-mediated phenotypes," *Nature*, 571(7766):576-579 (2019).

TABLE 5

| Comparator study | Inclusion criteria | Tissue % (Samples/Total) | GuardantOMNI % (Samples/Total) |
|---|---|---|---|
| PROFOUND, TOPARP | Samples passed QC | 69% (2792/4425), 84% (592/711) | 95.2% (654/687)* |
| MSKCC | Deleterious SNV/Indel, homozygous deletions in the following genes: BRCA1, BRCA2 | 9.4% (98/1042) | 12.4% (81/654) |
| PROFOUND | Deleterious SNV/Indel, homozygous deletions, re-arrangements in the following genes: BRCA1, BRCA2, ATM, BARD1, BRIP1, CDK12, CHEK1, CHEK2, FANCL, PALB2, RAD51B, RAD51C, RAD51D, RAD54L, PPP2R2A | 28% (778/2792) | 29.4% (192/654) |
| TOPARP | Deleterious SNV/Indel, homozygous deletions In the following genes: BRCA1, BRCA2, ATM, PALB2, ATR, ATRX, CHEK1, CHEK2, FANCA, FANCL, RANCM, MSH2, NBN, RAD50, XRCC3, FANCC, FANCD2, FANCE, FACF**, RANCM**, MSH6, WRN, FANCI, FANCG, BLM, ARID1A | 22.6%, (161/711) | 24.0% (157/654) |

Figure 16:
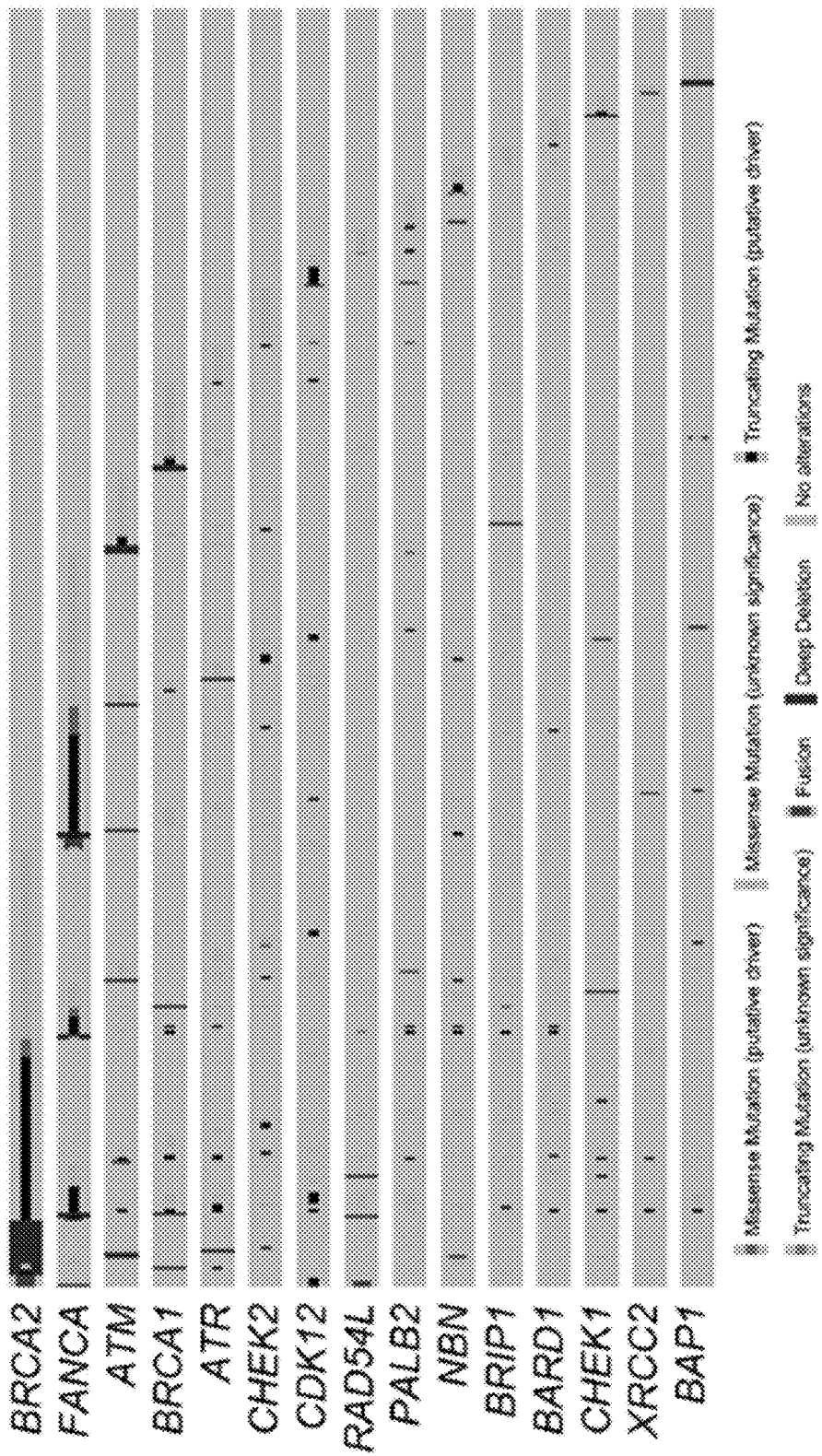
FIG. 16 is an oncoprint of HRR mutations in a prostate cancer cohort.

FIG. 16 is an oncoprint of HRR mutations in the prostate cancer cohort. Only homozygous gene copy number deletions are shown.

FIG. 17 (panels A-C) are plots of the prevalence of HRR mutations by variant classes detected in the prostate cohort. Panel A shows HRR mutations by variant type, where 'deletions' indicate deletions with insufficient allele information to determine zygosity. Panel B Left shows deleterious SNV/Indels by gene and somatic status. No reversions were detected in this cohort, consistent with low prevalence (3/1000 samples) in clinical prostate cohort (data not shown). Right shows fusions and long deletions by gene. HRR fusions and long deletions were found in 3.2% (21/654) of samples, none of which had a deleterious HRR SNV/Indel. Panel C shows an example of a BRCA2 deletion of exons 24-26. Black center line indicates discontinuous axis and the Bottom shows a distance view of multi-exons deleted.

CONCLUSION

This example demonstrates in a prostate cancer cohort that GuardantOMNI ctDNA profiling calls all classes of mutations contributing to HRD, with relative prevalence of alterations consistent with those in tissue. CfDNA presents an alternative for identifying patients who may benefit from PARP or cisplatin/platinum therapies, expanding the prevalence from 28% using small variants to 42% with the complete HRD biomarker set.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. A method for treating a subject having cancer with an immunological therapeutic agent, the method comprising:
    (a) determining homologous recombination deficiency (HRD) positive status for a biological sample from a subject, indicating that the subject has a cancer characterized by responsiveness to the immunological therapeutic agent, by:
  i) obtaining the biological sample from the subject, wherein the biological sample comprises cell-free DNA (cfDNA);
  ii) performing a diagnostic assay on the biological sample to determine a HRD score, wherein the diagnostic assay comprises:
    A) determining sequence data for the biological sample;
    B) determining, based on the sequence data, coverage data;
    C) determining, based on the coverage data, one or more breakpoints associated with one or more fusion events;
    D) determining, based on the coverage data, one or more deletions associated with one or more genes;
    E) determining, based on the one or more breakpoints and the one or more deletions, the HRD score; and
    F) classifying, based on the HRD score, the biological sample as HRD positive when the HRD score exceeds a threshold; and
(b) determining the subject has HRD positive status based on the HRD score exceeding the threshold and administering the immunological therapeutic agent to treat the subject determined to have the HRD positive status.

2. The method of claim 1, wherein determining sequence data for the biological sample comprises sequencing a panel of one or more homologous recombination repair (HRR) genes.

3. The method of claim 2, wherein the one or more HRR genes is selected from the group consisting of: ATM, ATR, BARD1, BRCA1, BRCA2, BRIP1, CDK12, CHEK1, CHEK2, FANCA, FANCL, NBN, PALB2, RAD51, RAD51B, RAD51C, RAD51D, RAD54L, HDAC2, MRE11, PPP2R2A, XRCC5, WRN, MLH1, FANCC, BAP1, XRCC2, XRCC3, and RAD50.

4. The method of claim 1, wherein the coverage data is associated with a plurality of bins, wherein the plurality of bins represents regions of a chromosome.

5. The method of claim 1, wherein determining, based on the coverage data, one or more breakpoints associated with one or more fusion events comprises:
  aligning a plurality of sequence reads from the sequence data to a reference sequence;
  determining one or more breakpoints in an alignment of a plurality of sequence reads of the plurality of sequence reads to the reference sequence;
  identifying any sequence reads associated with the one or more breakpoints in the alignment as candidate fusion sequence reads;
  determining candidate fusion sequence reads associated with common breakpoints of one or more breakpoints;
  grouping the candidate fusion sequence reads based on one or more common breakpoints;
  assembling the candidate fusion sequence reads in the groups into one or more contigs;
  aligning the contigs from the groups of the plurality of groups to the reference sequence;
  determining, based on the alignments of the contigs from the groups, one or more candidate fusion events;
  applying one or more criteria to the one or more candidate fusion events; and
  determining, based on applying the one or more criteria to the one or more candidate fusion events, one or more fusion events.

6. The method of claim 1, wherein determining, based on the coverage data, the one or more deletions associated with one or more genes comprises determining, based on the coverage data, a plurality of segments, where the plurality of segments are separated by a change point.

7. The method of claim 6, wherein determining the plurality of segments comprises applying a segmentation algorithm.

8. The method of claim 7, wherein the segmentation algorithm comprises a circular binary segmentation algorithm.

9. The method of claim 6, wherein the change point corresponds to positions where the coverage data indicates an underlying DNA copy number has changed.

10. The method of claim 6, further comprising:
  comparing the plurality of segments to a reference sequence to identify a subset of the plurality of segments comprising at least one deletion;
  removing, from the subset of the plurality of segments, any segment that spans a length of a chromosome;
  combining, in the subset of the plurality of segments, any segments that are less than a threshold distance apart;
  removing, from the subset of the plurality of segments, any segment with a length less than a threshold length; and
  removing, from the subset of the plurality of segments, any segment associated with a technical artifact.

11. The method of claim 10, further comprising determining, based on one or more remaining segments in the subset of the plurality of segments and based on the one or more breakpoints associated with the one or more fusion events, a number of breakpoints between segments that are adjacent within a threshold.

12. The method of claim 10, further comprising determining, based on one or more remaining segments in the subset of the plurality of segments, a number of segments associated with a single copy of a region of interest or associated with both copies of the region of interest being deleted.

13. The method of claim 6, wherein determining, based on the one or more breakpoints and the one or more deletions, the HRD score comprises summing a number of breakpoints and a number of segments.

14. The method of claim 1, wherein the one or more deletions comprise one or more of a homozygous deletion or a loss-of-heterozygosity (LOH) deletion.

15. The method of claim 1, further comprising annotating one or more variants contained in the sequence data, wherein the annotating comprises determining a clinical significance annotation associated with the one or more variants impact to human health.

16. The method of claim 1, further comprising determining a maximum somatic allele fraction (MSAF).

17. The method of claim 16, wherein determining the MSAF comprises determining, based on the sequence data, a maximum percentage of variants in the biological sample comprising any somatic variant that is not annotated as clonal hematopoiesis origin and is a fusion or nonsynonymous single nucleotide variant (SNV) or insertion or deletion (indel).

18. The method of claim 1, wherein the threshold is determined based on one or more reference HRD scores.

19. The method of claim 1, wherein the immunological therapeutic agent is combined with a poly (ADP-ribose) polymerase (PARP) inhibitor (PARPi).

20. The method of claim 19, wherein the PARPi is selected from at least one of VELIPARIB, OLAPARIB, TALAZOPARIB, RUCAPARIB, NIRAPARIB, PAMIPARIB, CEP 9722, E7016, E7449, and 3-Aminobenzamide.

* * * * *